(12) United States Patent
Mehta et al.

(10) Patent No.: US 8,765,797 B2
(45) Date of Patent: Jul. 1, 2014

(54) TG2 INHIBITORS AND USES THEREOF

(75) Inventors: Kapil Mehta, Bellaire, TX (US);
Anupam Kumar, Houston, TX (US);
Jansina Fok, Houston, TX (US);
Shuxing Zhang, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/806,257

(22) PCT Filed: Jun. 21, 2011

(86) PCT No.: PCT/US2011/041208
§ 371 (c)(1),
(2), (4) Date: Dec. 21, 2012

(87) PCT Pub. No.: WO2011/163198
PCT Pub. Date: Dec. 29, 2011

(65) Prior Publication Data
US 2013/0158087 A1    Jun. 20, 2013

Related U.S. Application Data

(60) Provisional application No. 61/356,961, filed on Jun. 21, 2010.

(51) Int. Cl.
| C07D 333/34 | (2006.01) |
| C07D 259/00 | (2006.01) |
| C07D 333/24 | (2006.01) |
| C07D 333/04 | (2006.01) |
| A61K 31/381 | (2006.01) |
| A61K 31/41 | (2006.01) |

(52) U.S. Cl.
CPC .......... *C07D 333/04* (2013.01); *C07D 275/023* (2013.01); *A61K 31/381* (2013.01); *A61K 31/41* (2013.01)
USPC ........... 514/381; 514/445; 514/448; 548/251; 549/65; 549/72

(58) Field of Classification Search
None
See application file for complete search history.

(56) References Cited

U.S. PATENT DOCUMENTS

| 2003/0187001 A1 | 10/2003 | Calderwood et al. | |
| 2004/0167128 A1* | 8/2004 | Comess et al. | 514/227.8 |
| 2007/0167628 A1* | 7/2007 | Gellibert et al. | 546/122 |
| 2008/0279844 A1 | 11/2008 | Mehta et al. | |

FOREIGN PATENT DOCUMENTS

| CN | 102670590 | 9/2012 |
| WO | WO 2006/081389 | 8/2006 |
| WO | WO 2008/057775 | 5/2008 |
| WO | WO 2008/063760 | 5/2008 |

OTHER PUBLICATIONS

Shvedov et al. disclose in Khimiko-Farmatsvetticheskii Zhurnal (1978), 12(11), 53-56 (English Abstract).*
Han et al. In J Cancer Res Clin Oncol (1999) 125:89-95.*
Ai et al. In Carcinogenesis 29(3) 510-518, 2008.*
Yuan et al. In Mol Cancer Ther 4(9), 1293-1302 (2005).*
Verma et al. In Clin Cancer Res 14(8) 2476-2483 (2008).*
Hwang et al. In Cancer Res. 68(14), 5849-5858 (2008).*
Database Chemcats Chemical Abstract Service, Accession No. 0067452627, retrieved from STN order No. HTS04162, Apr. 23, 2013.
Database Chemcats Chemical Abstract Service, Accession No. 0073562501, retrieved from STN order No. HTS04162, Aug. 21, 2013.
Database Chemcats Chemical Abstract Service, Accession No. 0088443594, retrieved from STN order No. Amb2741321, Jan. 1, 2013.
Colak et al., "Cytosolic guanine nucleodotide binding deficient form of transglutaminase 2 (R580a) potentiates cell death in oxygen glucose deprivation", *PLoS One*, 6(1):e16665, 2011.
Kumar et al., "Evidence that aberrant expression of tissue transglutaminase promotes stem cell characteristics in mammary epithelial cells", *PLos One*, 6(6):e20701, 2011.
Kumar et al., "Tissue transglutaminase protmotes drug resistance and invasion by inducing mesenchymal transition in mammary epithelial cells", *PLoS One*, 5(10):e13390, 2010.
PCT International Preliminary Report on Patentability issued in International Application No. PCT/US2011/041208, issued Dec. 28, 2012.
PCT International Searching Report and Written Opinion issued in International Application No. PCT/US2011/041208, mailed Feb. 10, 2012.
Verma et al., "Therapeutic significance of elevated tissue transglutaminase expression in pancreatic cancer", *Clin Cancer Res.*, 14(8):2476-83, 2008.
Yuan et al., "Tissue transglutaminase 2 inhibition promotes cell death and chemosensitivity in glioblastomas", *Mol Cancer Ther.*, 4(9):1293-302, 2005.

* cited by examiner

*Primary Examiner* — Dennis Heyer

(74) *Attorney, Agent, or Firm* — Parker Highlander PLLC

(57) ABSTRACT

Methods and compounds for treating cancer, dmg resistance and/or metastasis are described herein. These methods and compounds can inhibit the expression of aberrant TG2 expression and/or inhibit the binding of GTP to TG2, and thereby prevent the induction of epithelial to mesenchymal transition of cancer cells, and a stem cell-like phenotype.

9 Claims, 45 Drawing Sheets

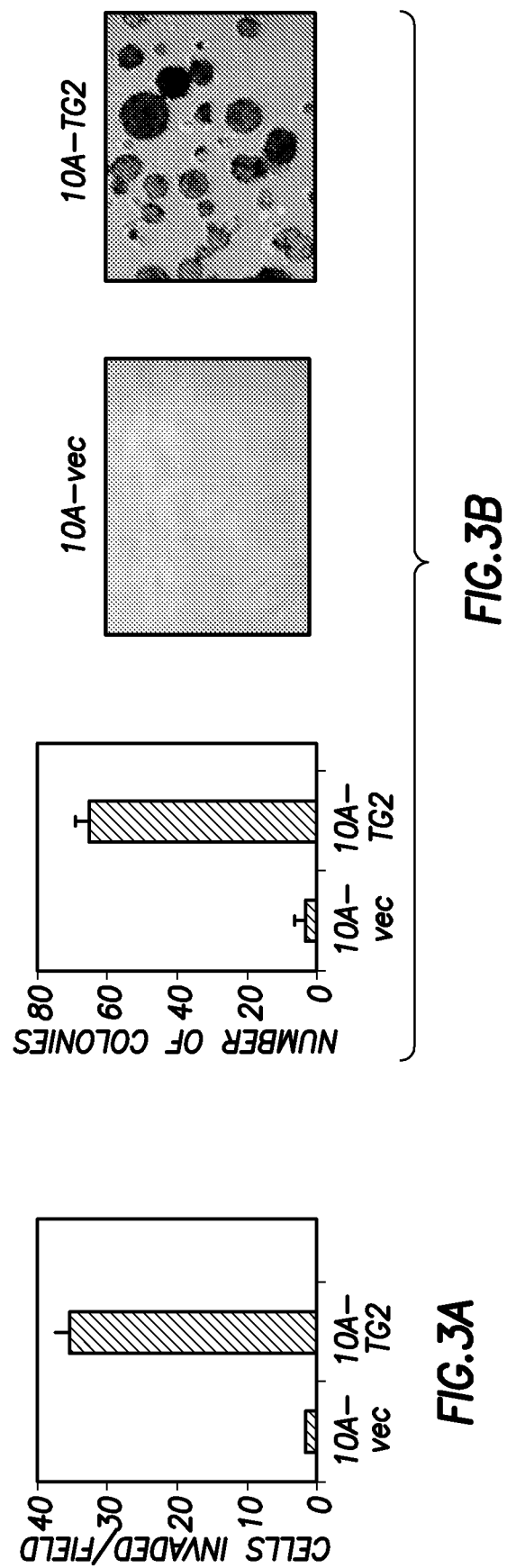

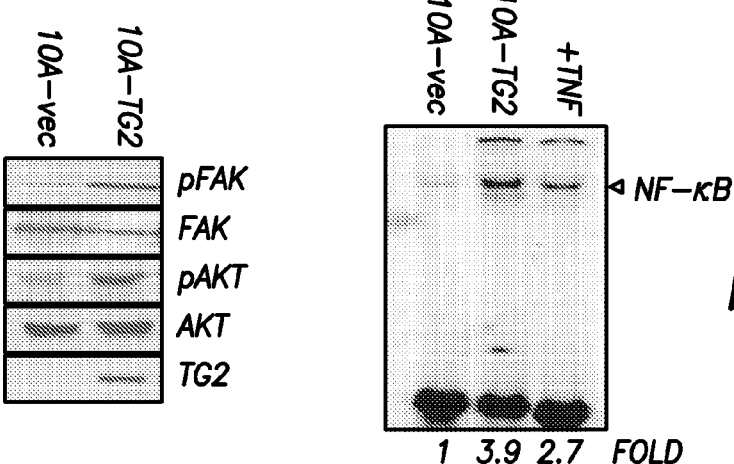
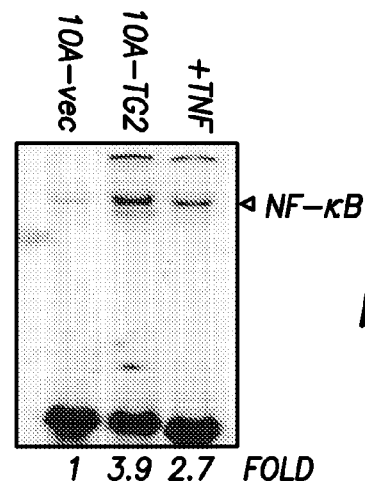
FIG.4A
FIG.4B
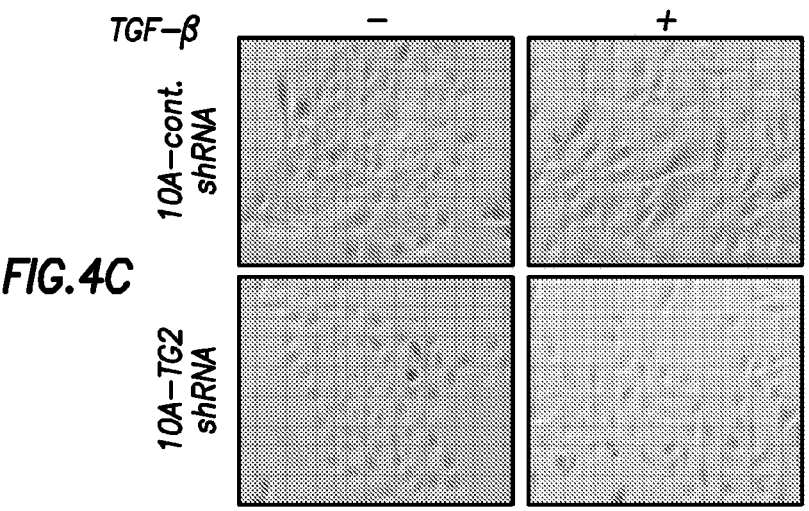
FIG.4C
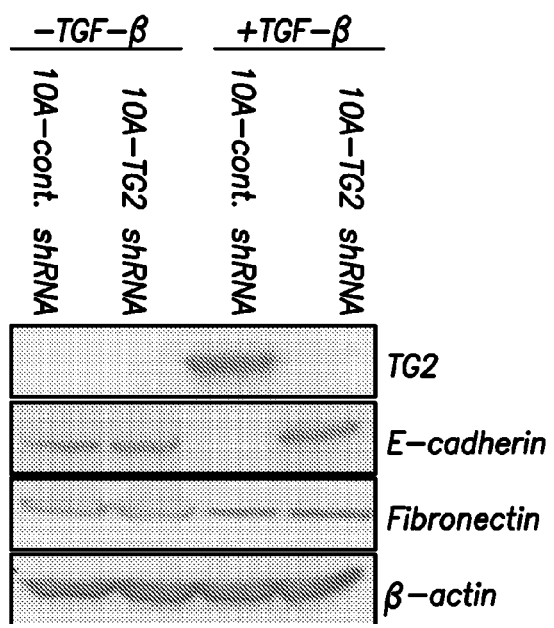
FIG.4D

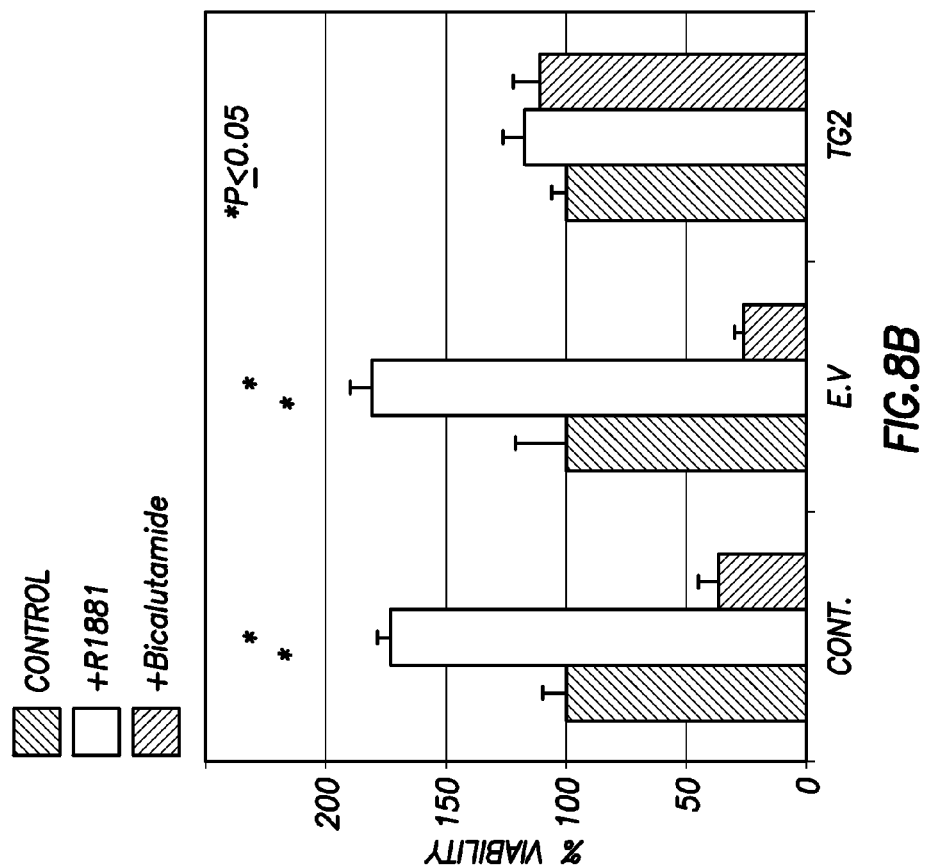
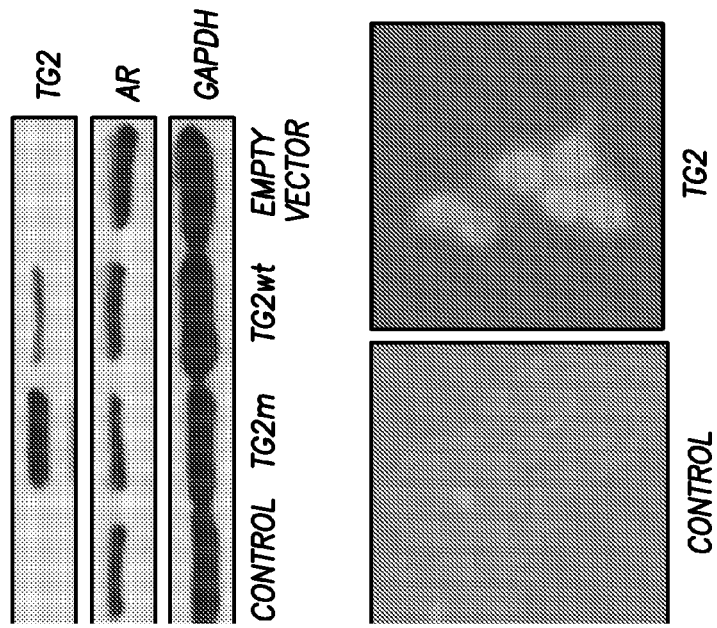

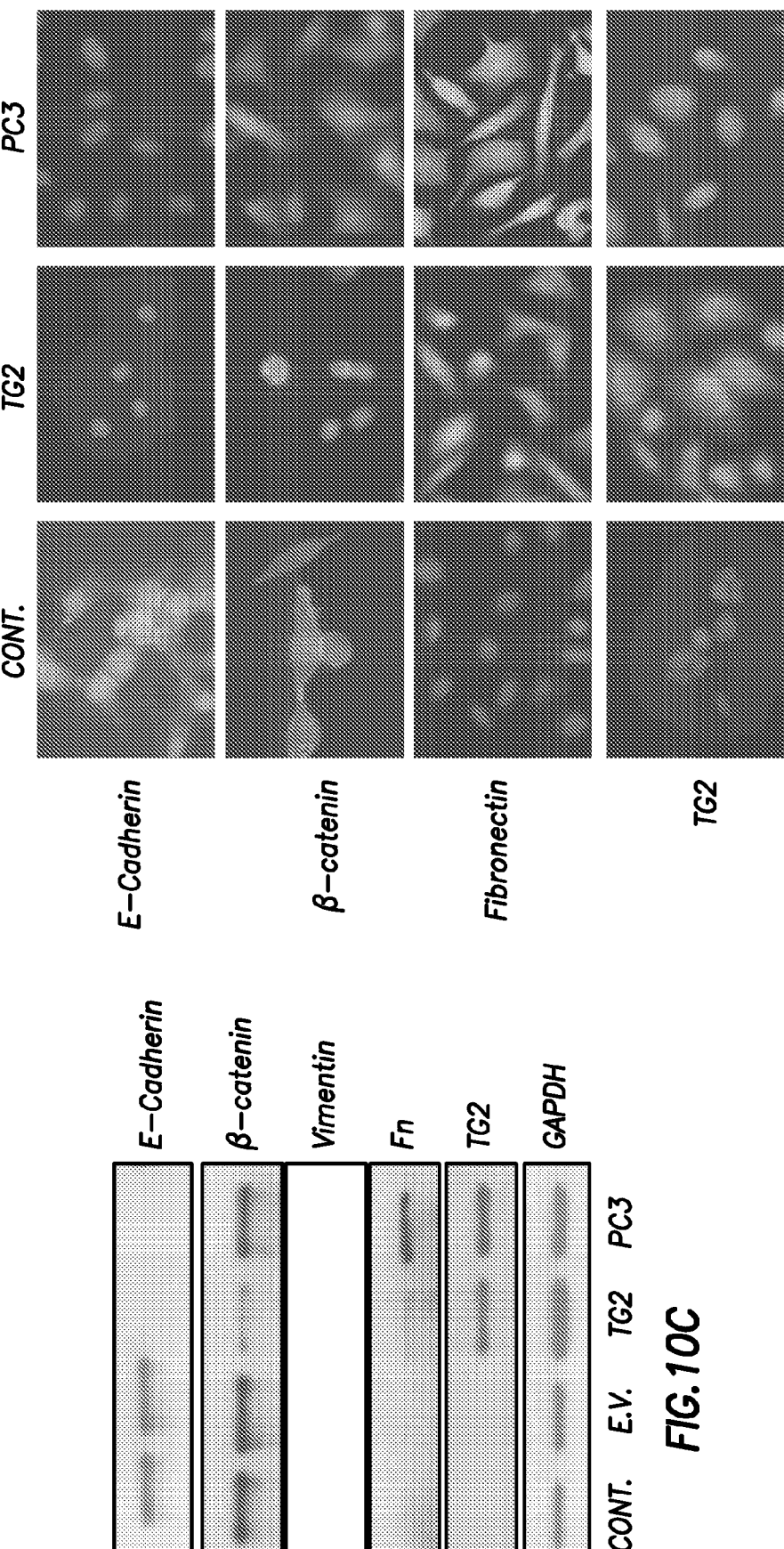

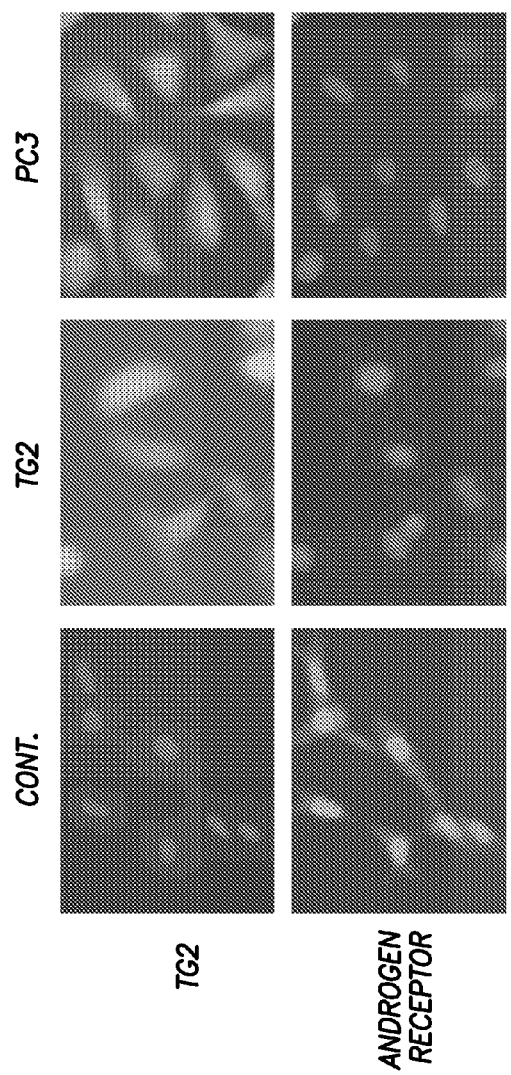
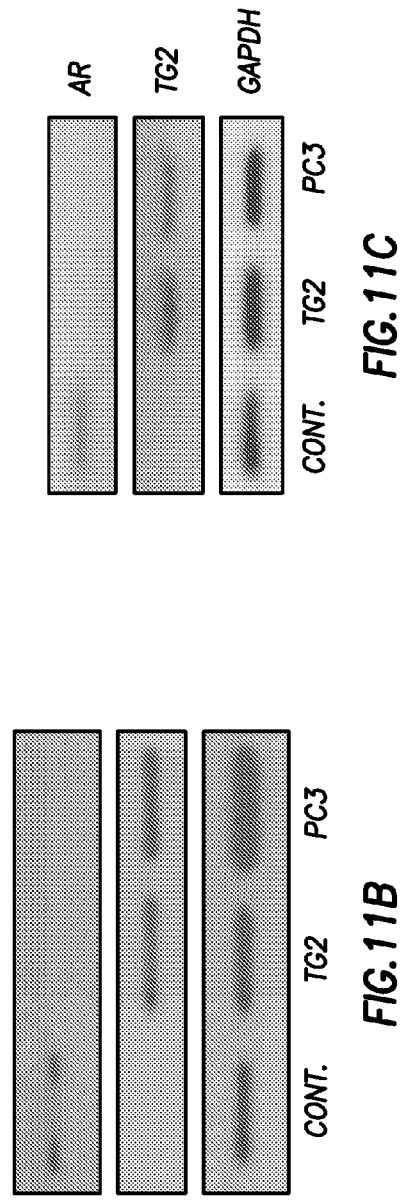
FIG. 11A
FIG. 11B
FIG. 11C

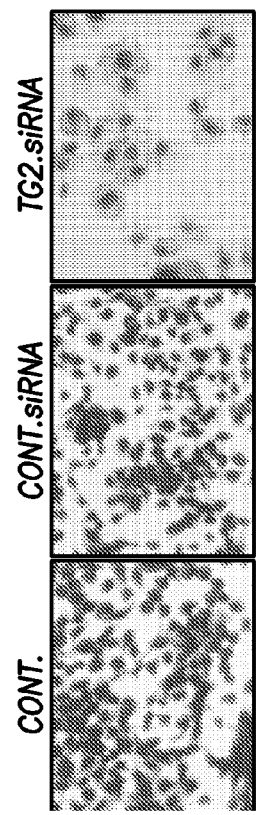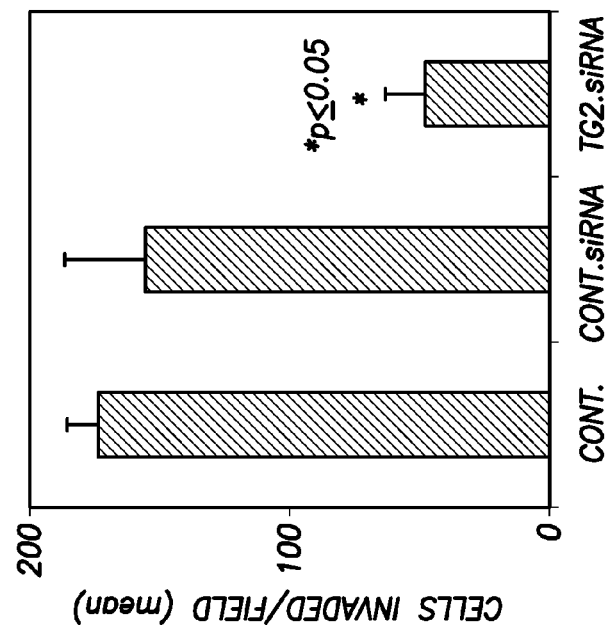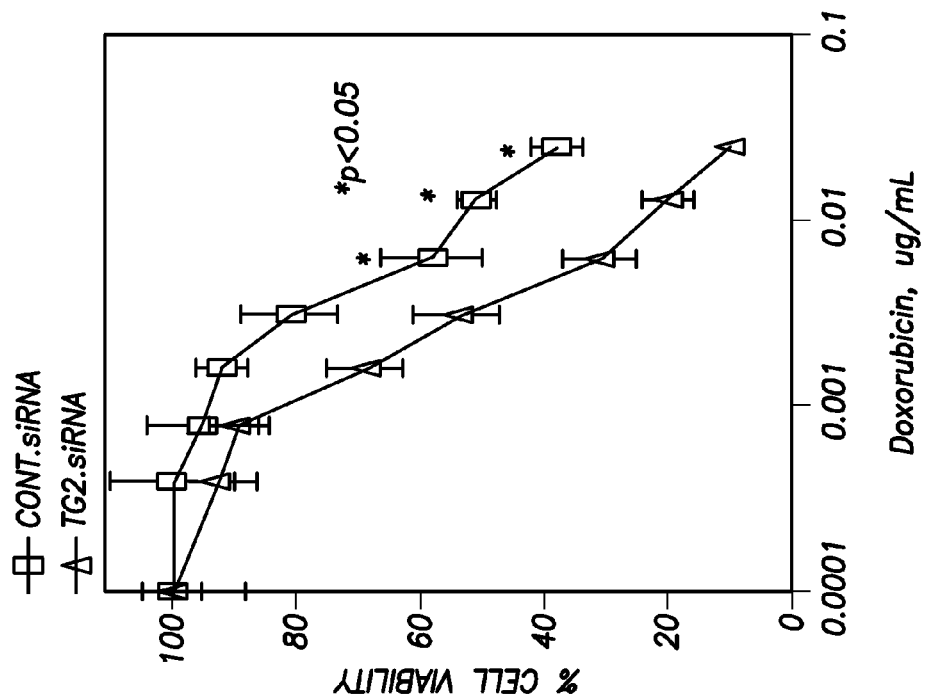
FIG. 12A
FIG. 12B

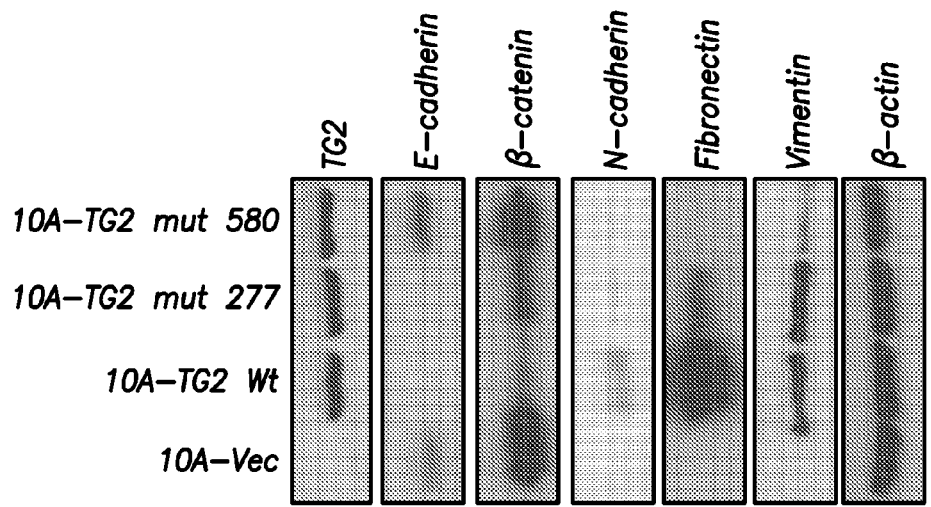
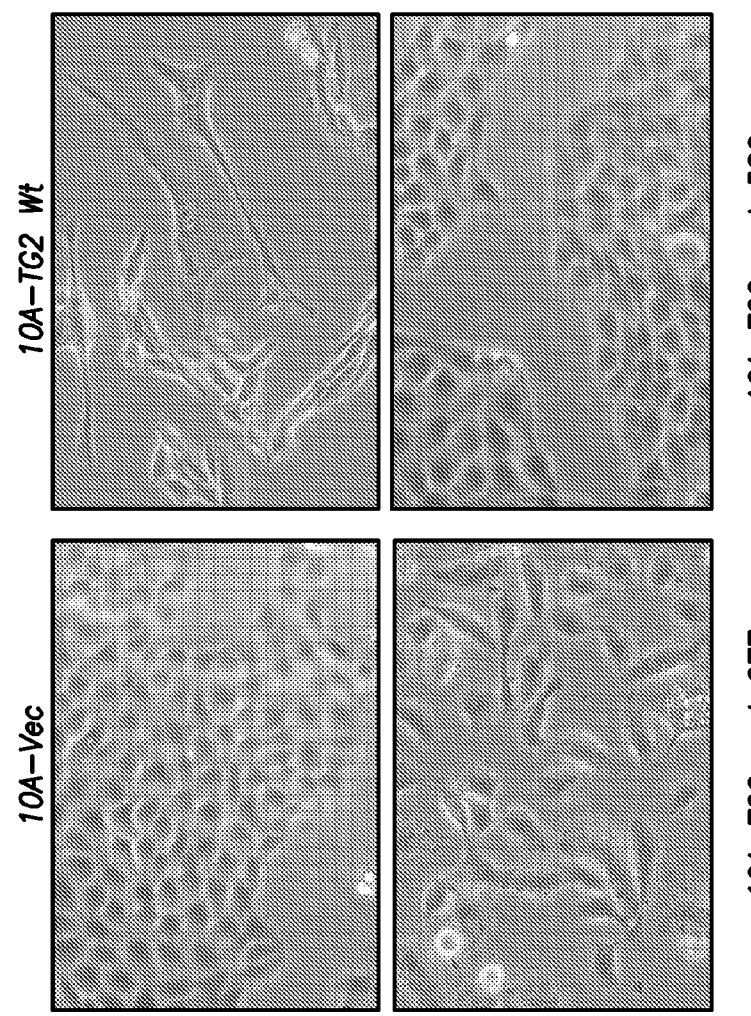
FIG. 13B
FIG. 13A

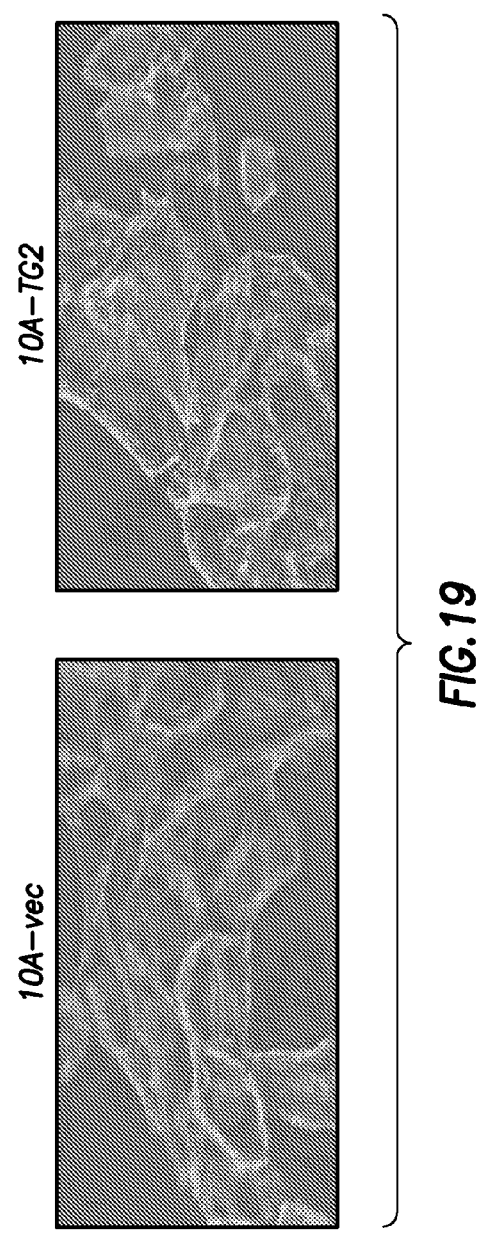
FIG.19
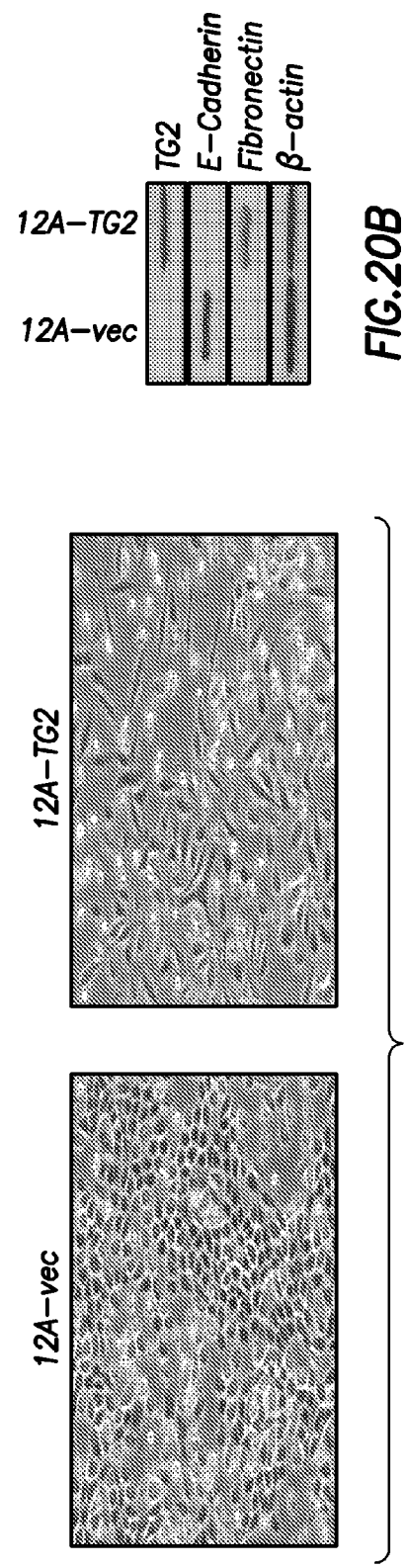
FIG.20A
FIG.20B

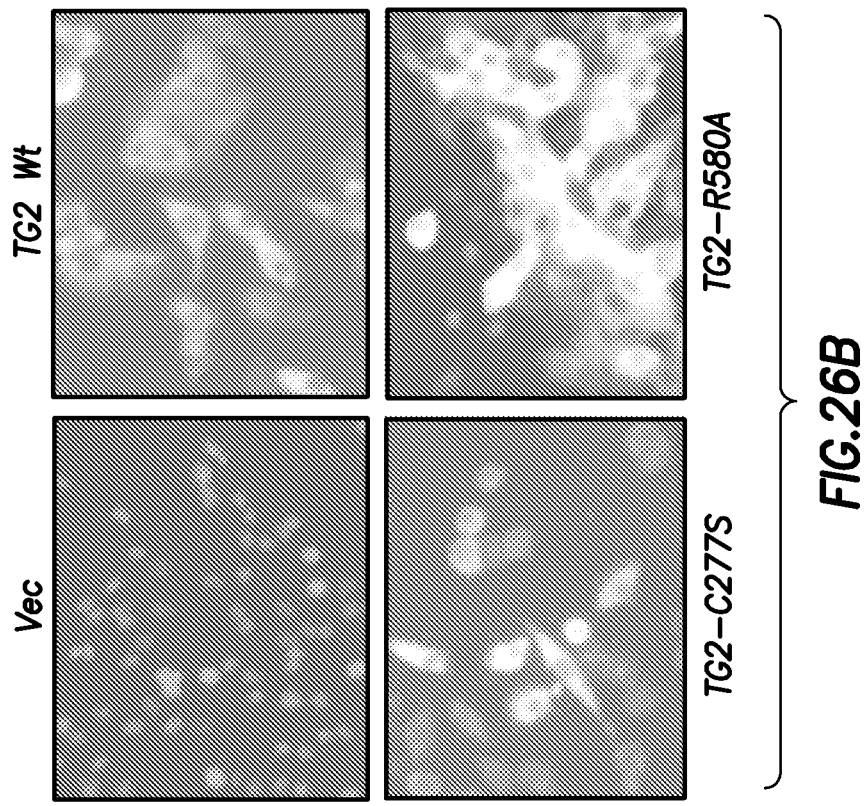
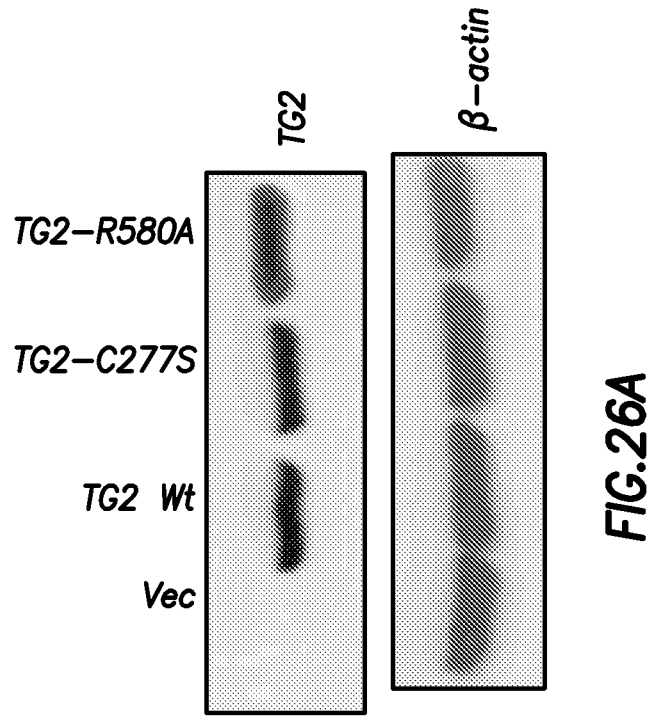
FIG. 26B
FIG. 26A

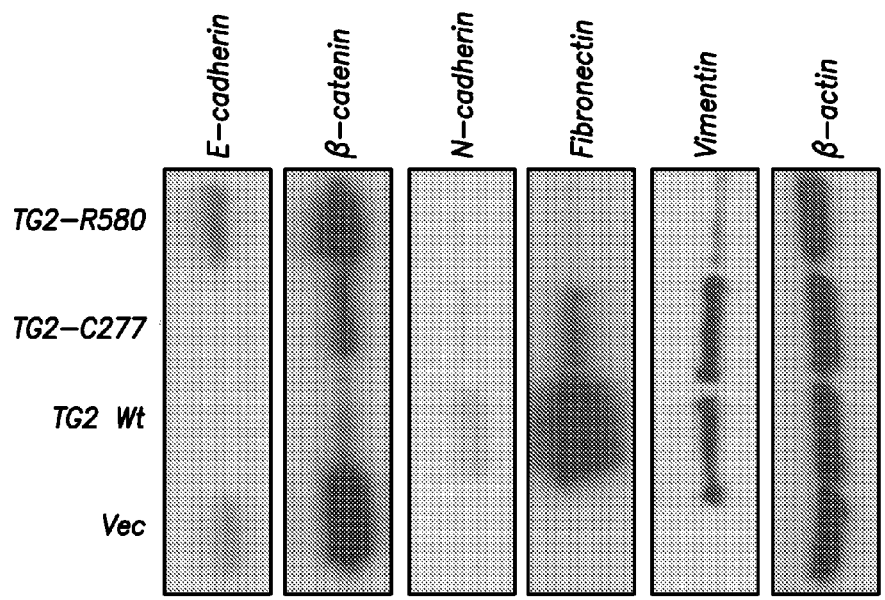
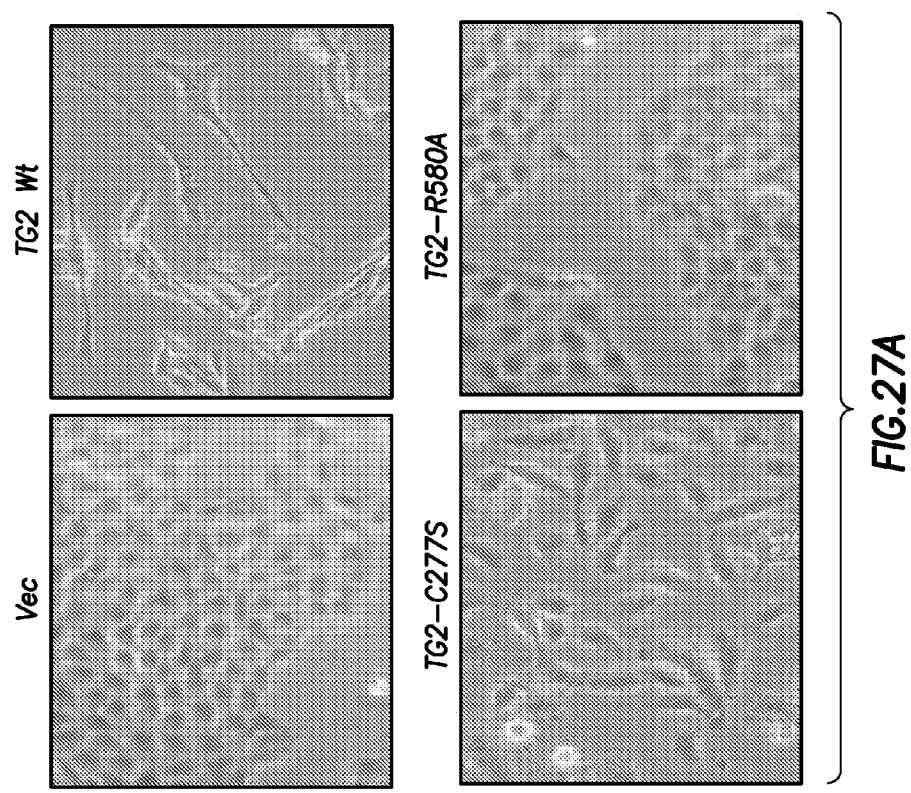
FIG. 27B
FIG. 27A

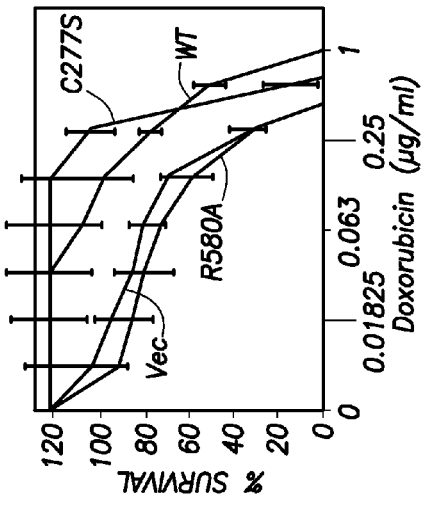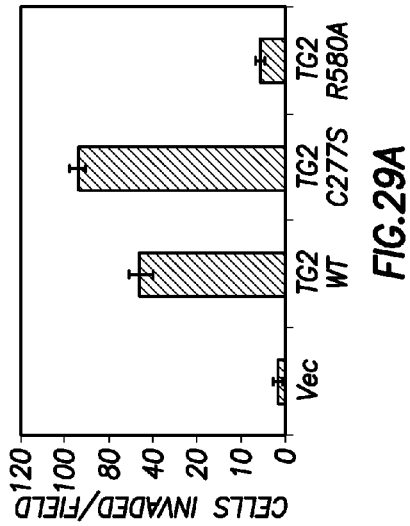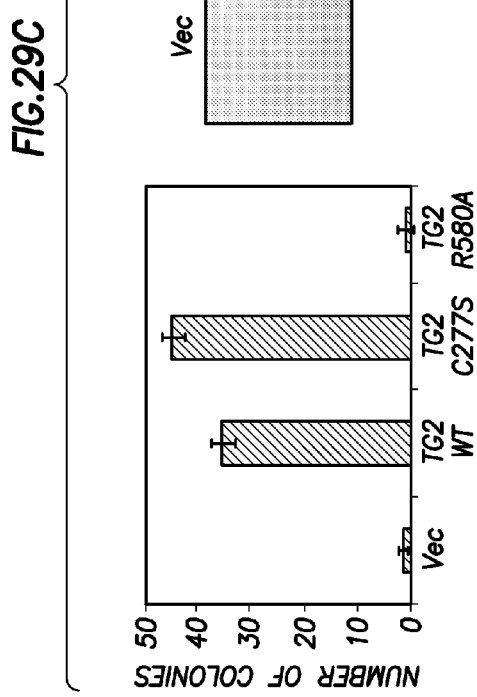

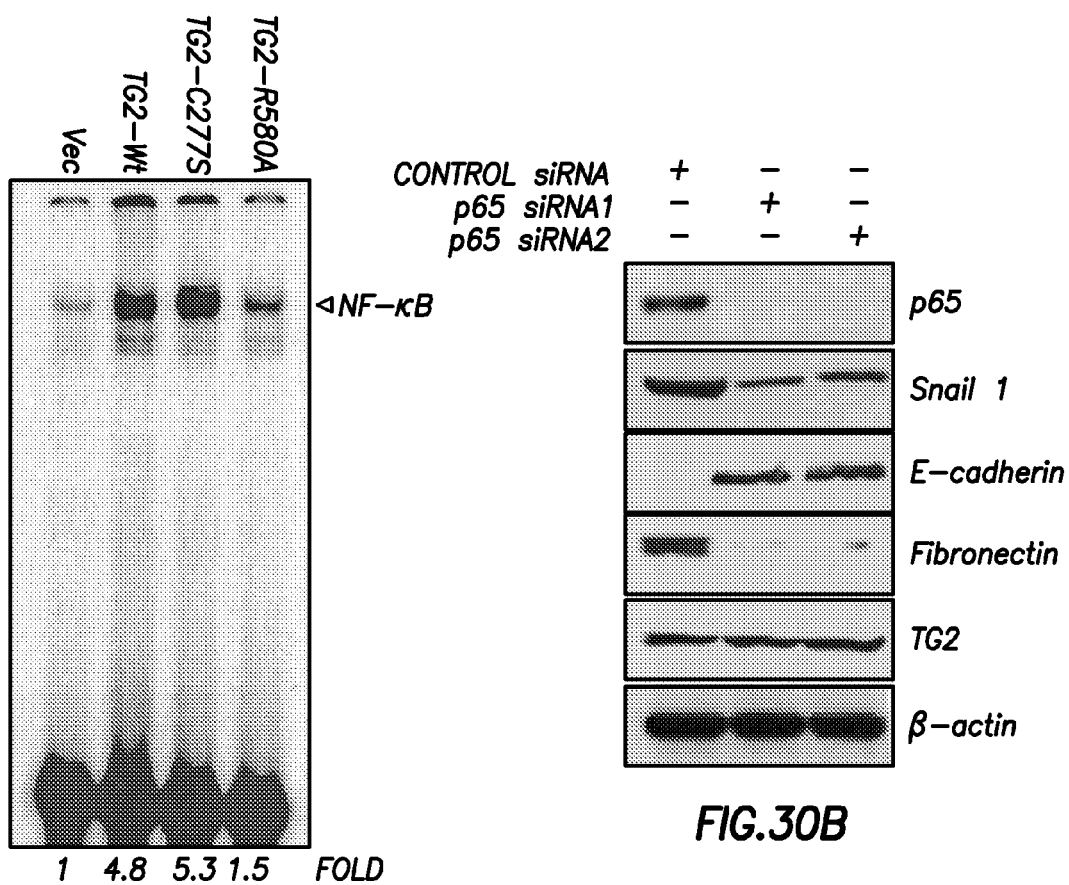
FIG.30A
FIG.30B
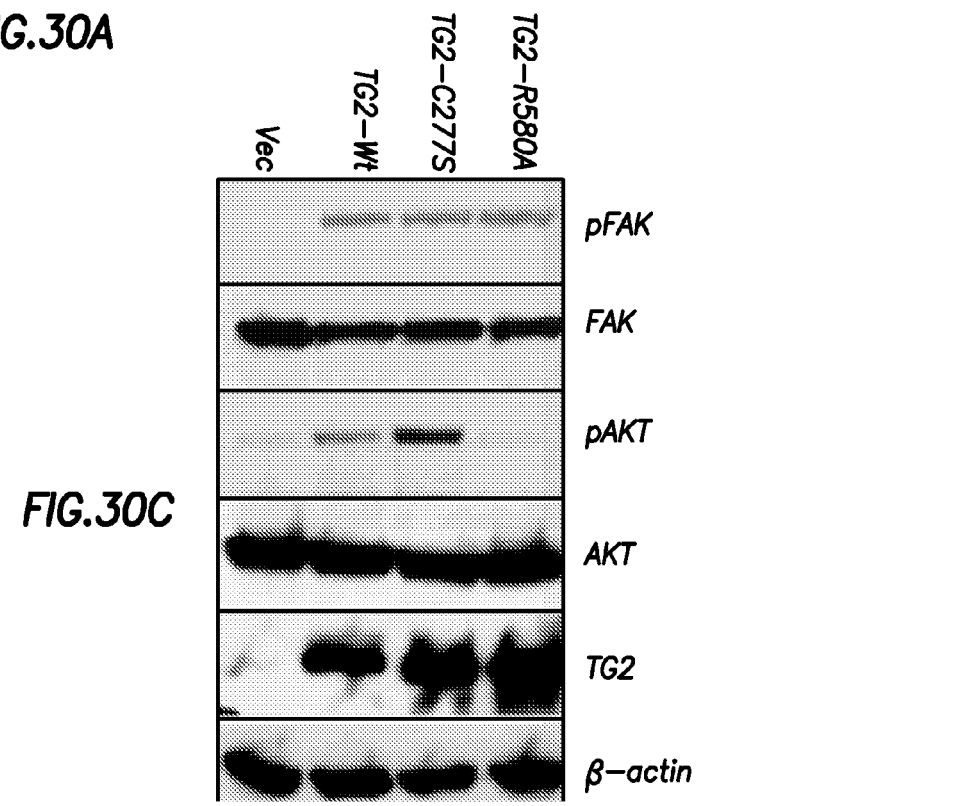
FIG.30C

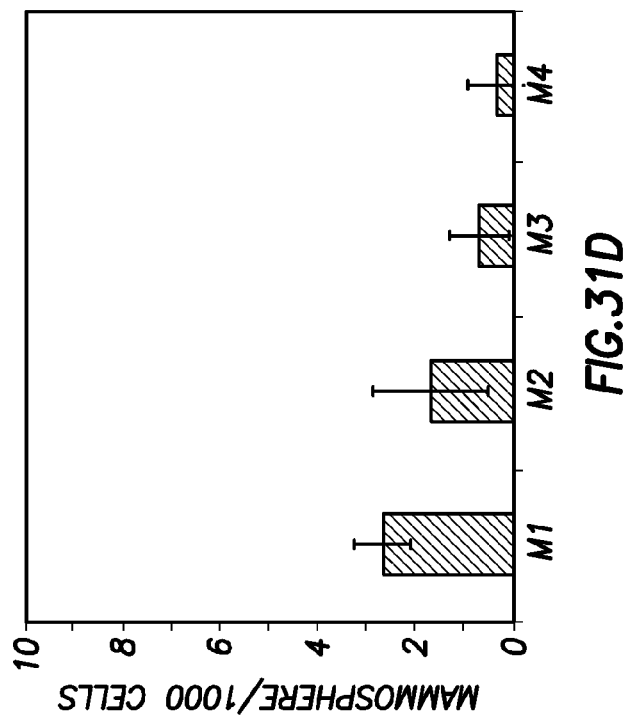
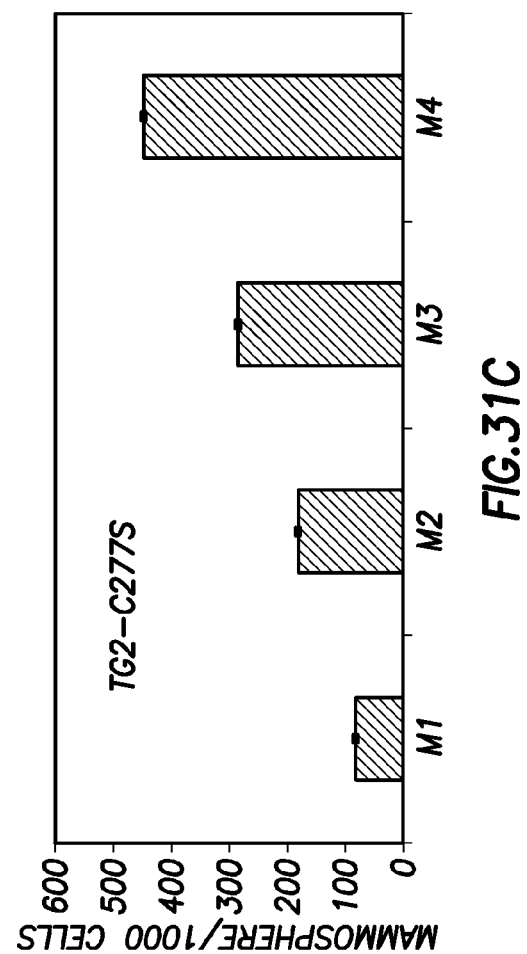

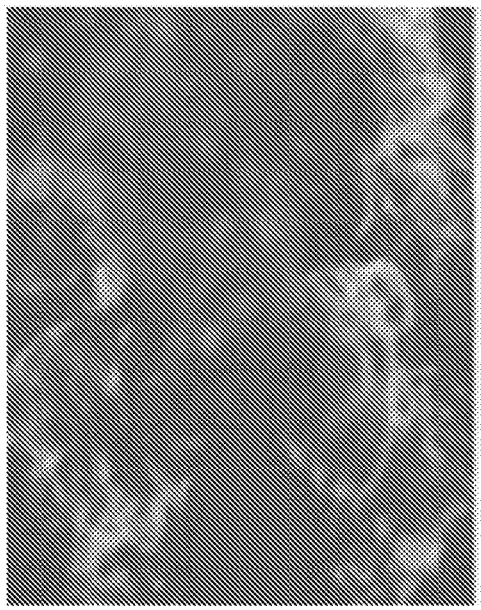
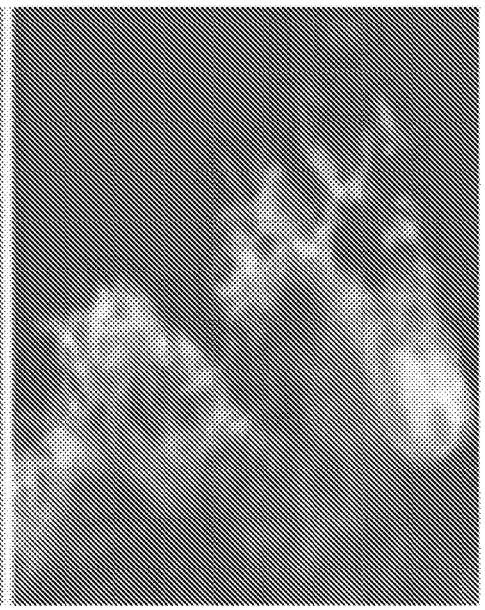
FIG.31F Muc1/integrin a6
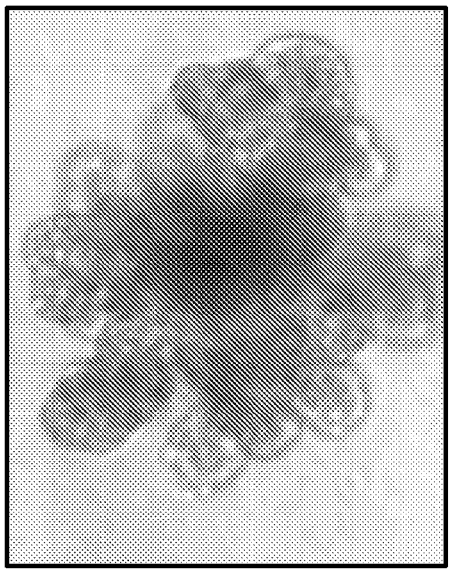
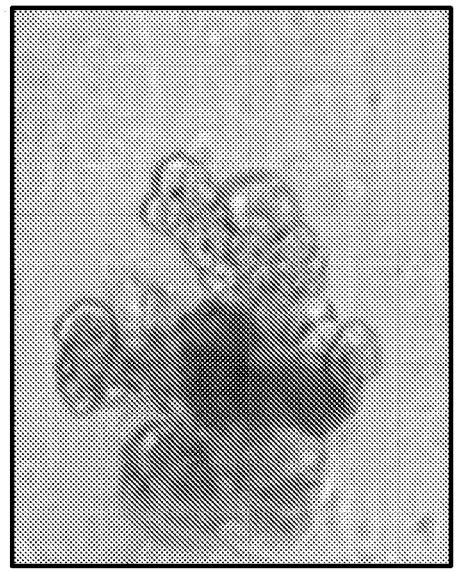
FIG.31E

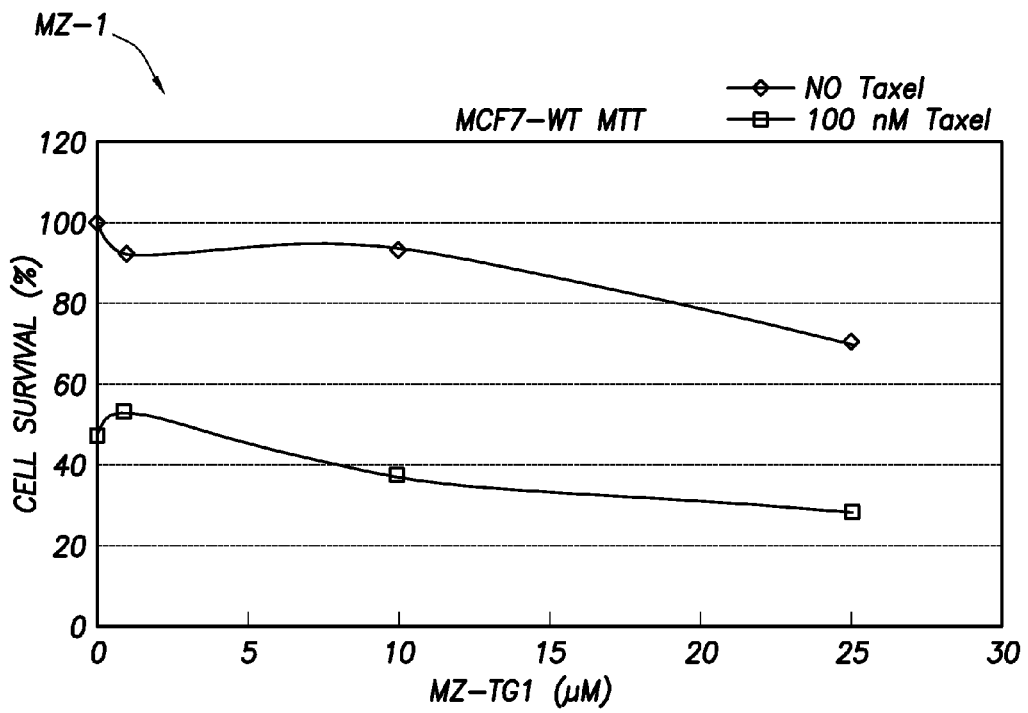
FIG.32A1
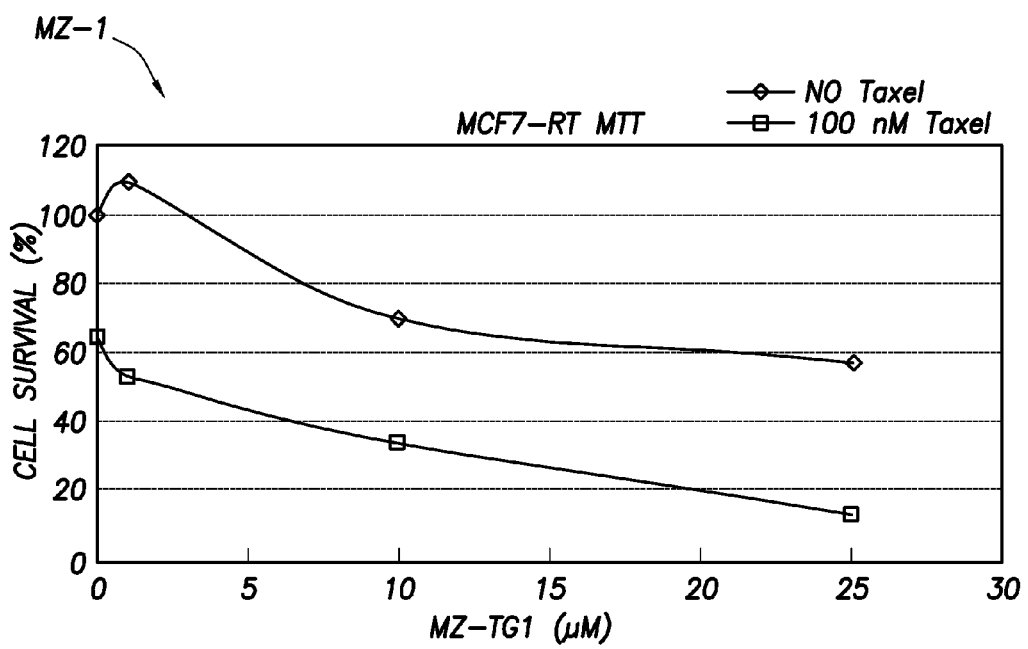
FIG.32A2

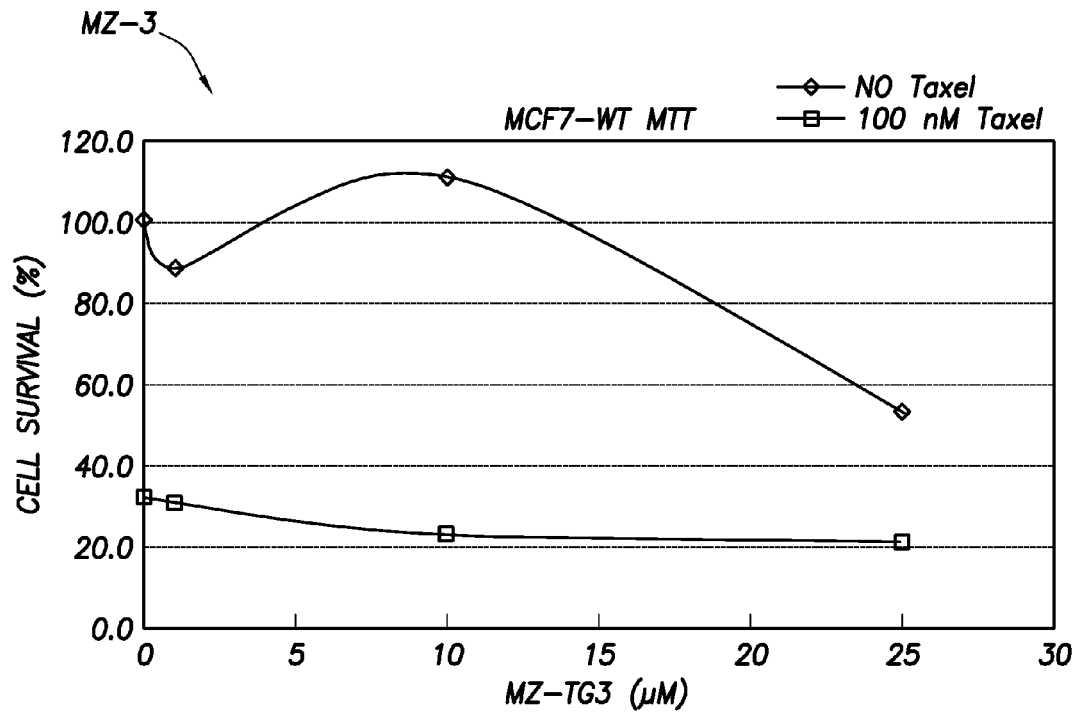
FIG.32B1
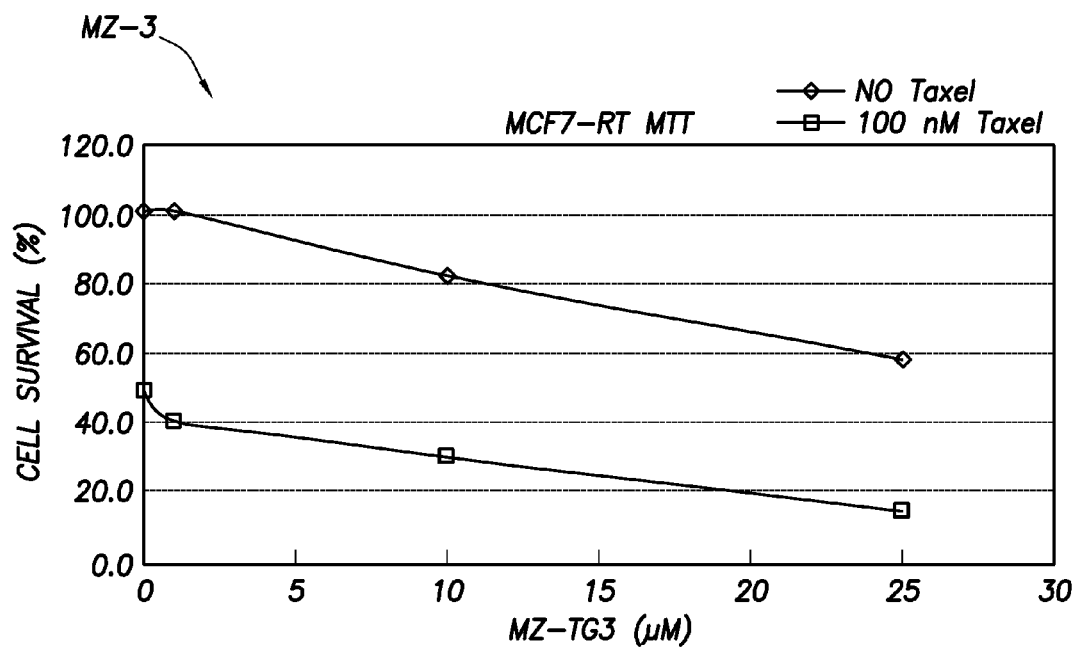
FIG.32B2

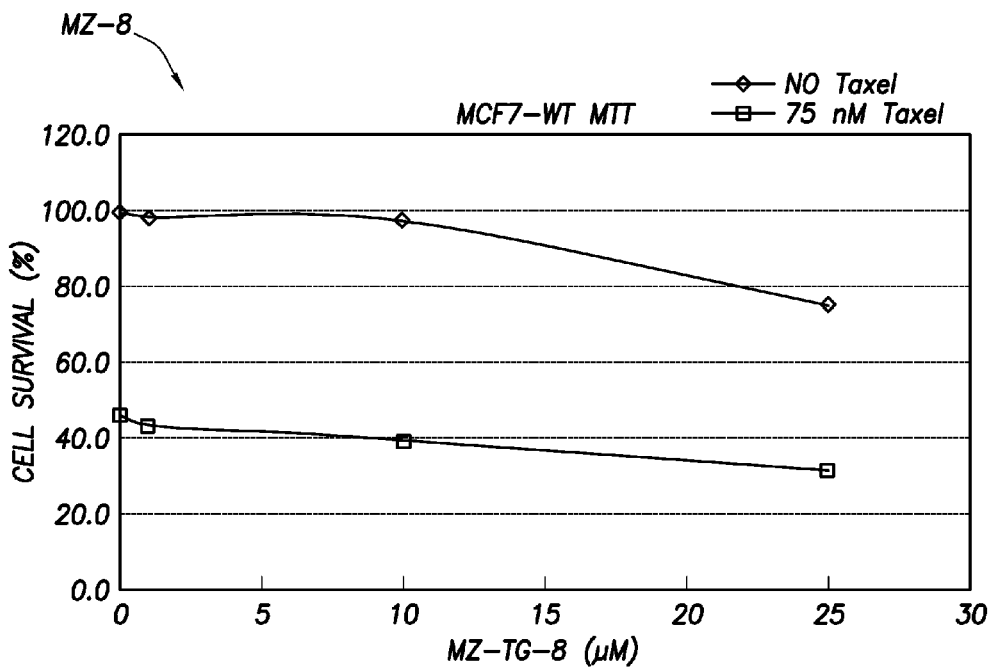
FIG.32C1
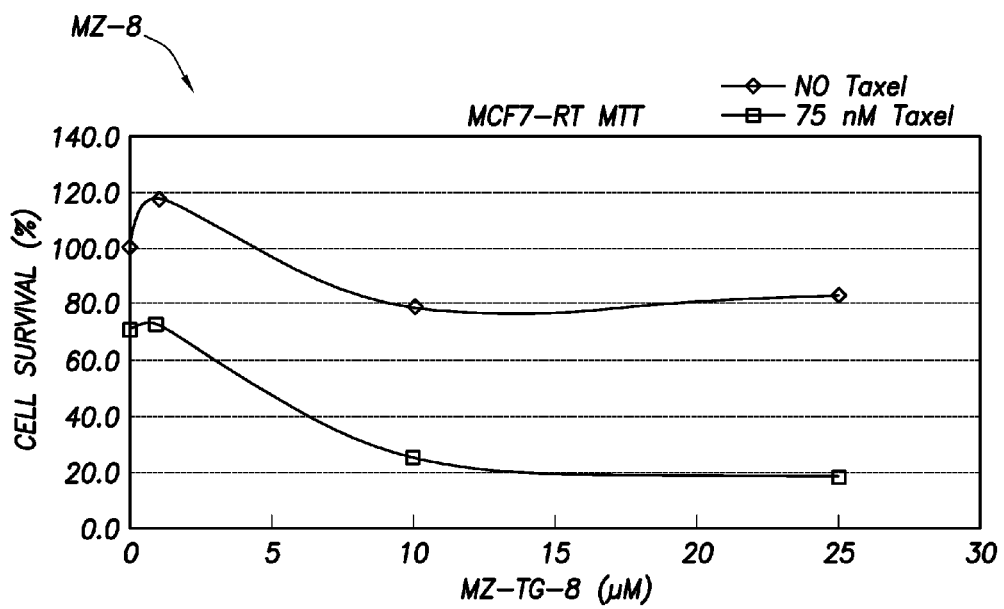
FIG.32C2

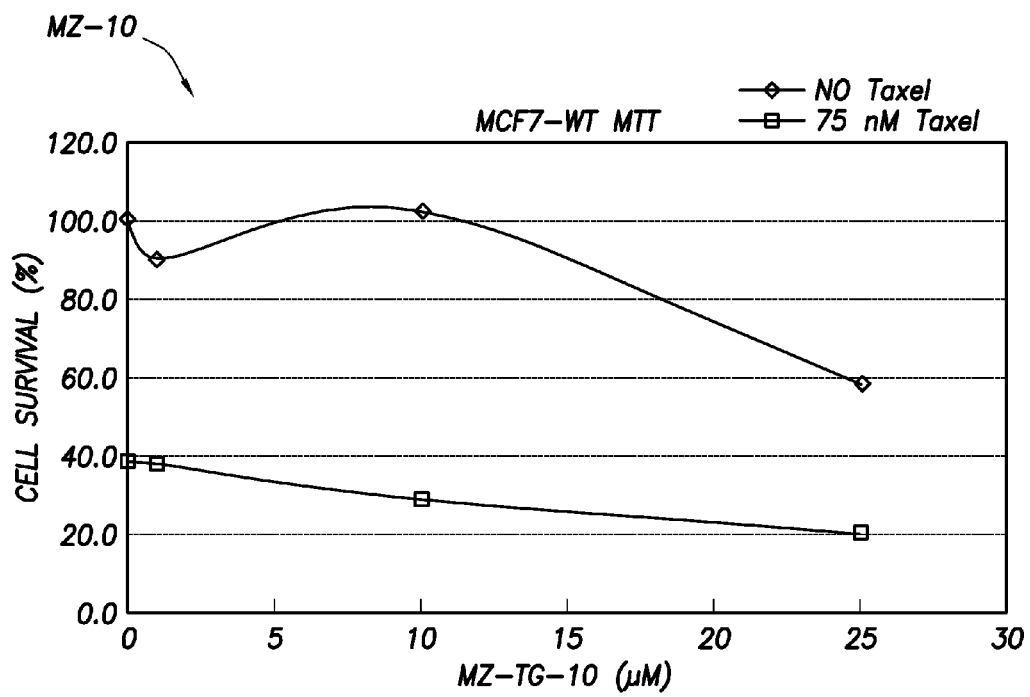
FIG.32D1
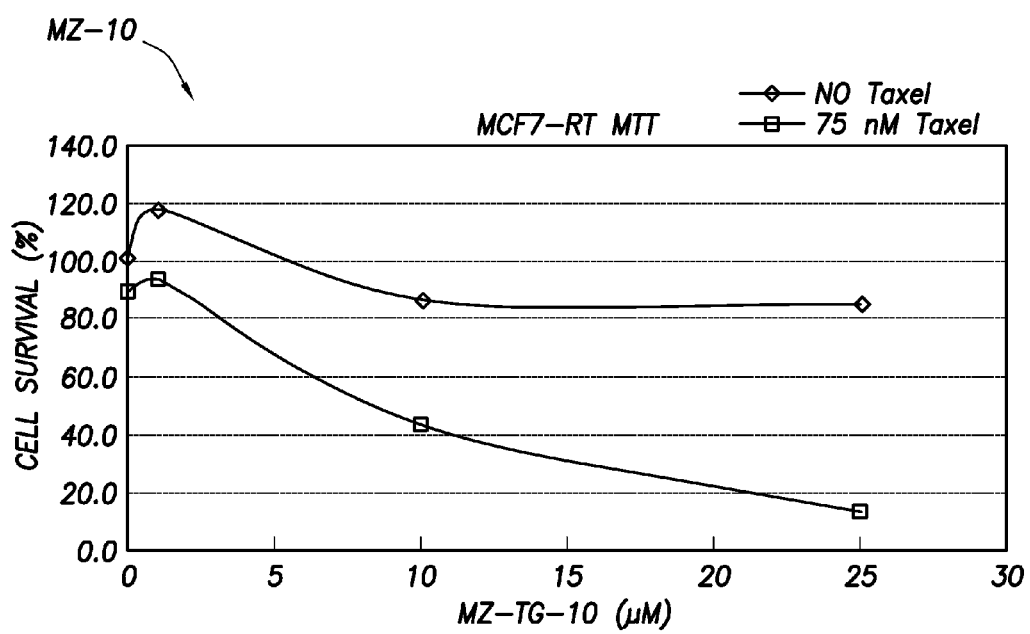
FIG.32D2

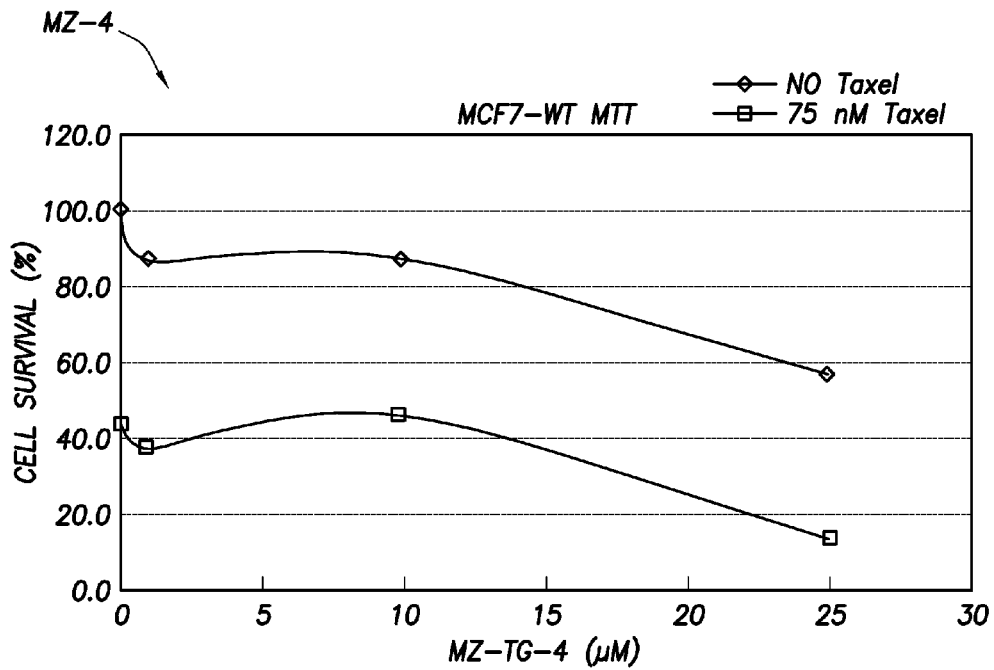
FIG.33A1
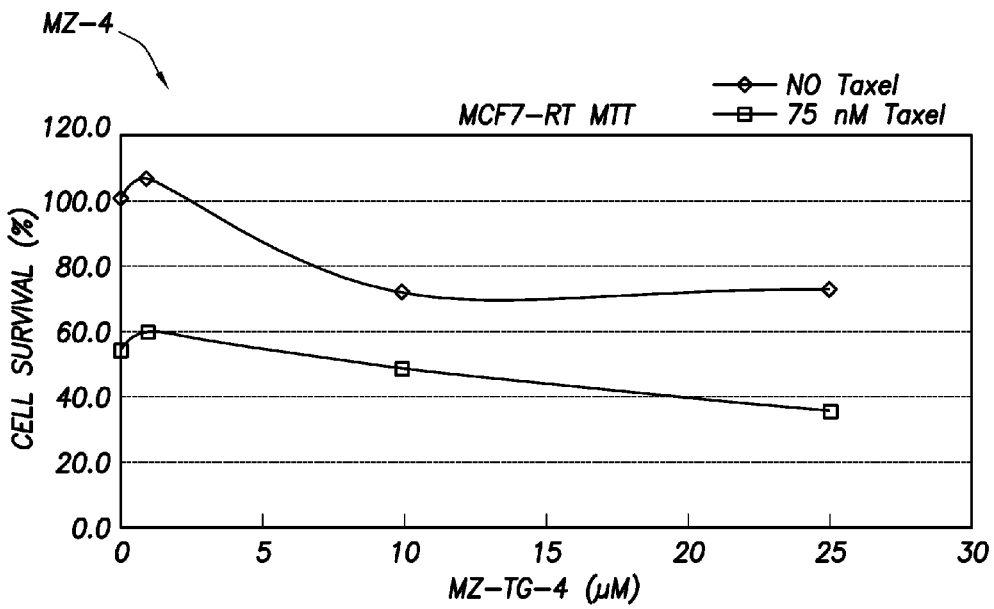
FIG.33A2

TG2 INHIBITORS AND USES THEREOF

CROSS-REFERENCE TO RELATED APPLICATIONS

This application is a national phase application under 35 U.S.C. §371 of International Application No. PCT/US2011/041208, filed Jun. 21, 2011, which claims priority to U.S. Provisional Application No. 61/356,961, filed Jun. 21, 2010. The entire content of each of the above-referenced disclosures is specifically incorporated herein by reference.

FIELD OF THE INVENTION

This invention is related to modulation of aberrant expression of TG2 and/or inhibition of GTP binding to TG2 to treat cancer, metastasis, drug resistance and other oncogenic properties.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

This disclosure includes a sequence listing submitted as a text file pursuant to 37 C.F.R. §1.52(e)(v) named UTSCP1191US.txt, created on Dec. 21, 2012, with a size of 22 KB (as measured in Microsoft Windows®), which is incorporated herein by reference. The attached sequence descriptions and Sequence Listing comply with the rules governing nucleotide and/or amino acid sequence disclosures in patent applications as set forth in 37 CFR. §§1.821-1.825.

BACKGROUND OF THE INVENTION

Epithelial-to-mesenchymal transition ("EMT") is a complex dynamic process that occurs during embryonic development for reprogramming of epithelial cells. Downregulation of E-cadherin, which occurs during EMT, results in the loss of homotypic adhesion. Reactivation of EMT during adult life has been associated with various pathological conditions. For example, EMT promotes the detachment of cancer cells from the primary tumor and facilitates migration through the acquisition of stem cell like properties, including loss of cellular polarity and adhesion. Metastasis and resistance to systemic therapies pose major clinical challenges to the treatment of breast and other cancers. Identification of tumor-coded genes and determining how these genes contribute to progression of the disease is important for developing new therapeutic strategies.

Although the significance of EMT in development of drug resistance, metastasis and stem cell-like characteristics of cancer cells has become evident, the mechanisms/pathways that lead to the induction of EMT/stem cell phenotype remain elusive. Delineation of these pathways could offer novel and promising therapeutic targets for treating drug resistant and metastatic tumors, which account for more than 90% cancer related death. To date, however, the specific inducers of EMT/stem cells are not known. Targets for inhibiting the expression of these phenotypes could produce cancer therapies that alone or in combination with existing drugs combat drug resistance.

BRIEF SUMMARY OF THE INVENTION

Transglutaminase 2 (TG2) is a pro-inflammatory gene whose aberrant expression promotes the invasive phenotype in normal and transformed epithelial cells by inducing epithelial-to-mesenchymal transition (EMT). Overexpression of TG2 results in induction of Snail1, Zeb1, Zeb2 and Twist1 transcription factors, supports anchorage-independent growth in soft-agar and promotes stem cell like phenotype in immortalized mammary (MCF10A, MCF12A) and transformed prostate (LnCaP) cells. Moreover, TG2 expression is associated with constitutive activation of focal adhesion kinase, Akt and nuclear factor-κB, all known mediators of EMT. Furthermore, we found TG2 expression disrupts the apical-basal polarity and resulted in disorganized acini structures when grown in 3D-culture. Tumor growth factor-beta (TGF-β) failed to induce EMT in cells lacking TG2 expression. Hence, TG2 is a downstream effector of TGF-β-induced EMT.

We have also discovered that TG2 expression is sufficient to induce DAT and a stem cell phenotype in normal and transformed cells. Aberrant expression of TG2 induces EMT and stein cell-like phenotype in epithelial cells, a process that is closely linked with drug resistance and metastasis in cancer cells, and development of degenerative fibrotic diseases. As disclosed herein, our findings now provide the link between progression of metastatic disease and TG2 expression, and prove that TG2 represents a potentially valuable therapeutic target.

Furthermore, we have discovered that transamidation activity of TG2 is not essential for promoting TG2 associated oncogenic functions. Moreover, TG2-dependent activation of the proinflammatory transcription factor, NF-κB, is essential for promoting the EMT/CSC phenotype in mammary epithelial cells.

As such, presented herein are small molecule inhibitors that block GTP-binding pocket of TG2. The small molecule inhibitors include compounds of the following structural formulas:

Formula I:

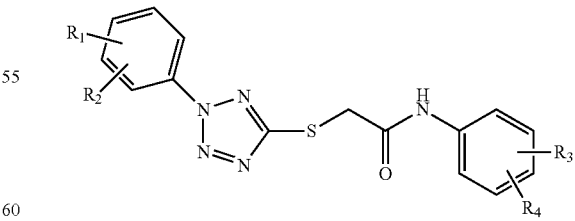

wherein $R_1$, $R_2$, $R_3$ and $R_4$ are each independently hydrido, halo, alkyl, alkoxy, amino, alkylamino, alkylcarbonylamino, dialkylamino, carbamoyl, nitro, cyano, perfluoroalkyl, trifluoromethylalkyl, hydroxyl, thiol, hydroxycarbonyl, or alkylcarbonyl;

Formula II:

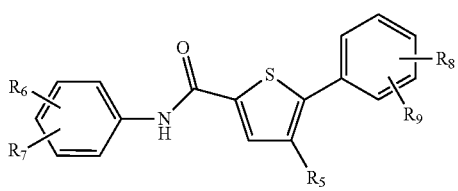

wherein $R_5$ is H or methyl, and $R_7$, $R_7$, $R_8$ and $R_9$ are independently selected from hydrido, halo, alkyl, alkoxy, amino, alkylamino, alkylcarbonylamino, dialkylamino, carbamoyl, nitro, cyano, perfluoroalkyl, trifluoromethylalkyl, hydroxyl, thiol, hydroxycarbonyl, alkylcarbonyl, or may constitute a 5- or 6-membered heterocyclic ring containing one or two oxygen atoms; and Formula III:

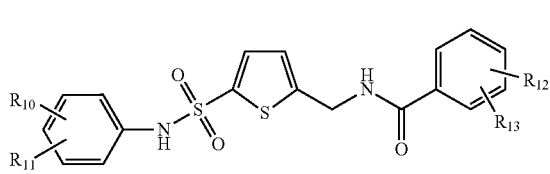

wherein $R_{10}$, $R_{11}$, $R_{12}$ and $R_{13}$ are independently selected from hydrido, halo, alkyl, alkoxy, amino, alkylamino, alkylcarbonylamino, dialkylamino, carbamoyl, nitro, cyano, perfluoroalkyl, trifluoromethylalkyl, hydroxyl, thiol, hydroxycarbonyl, alkylcarbonyl.

Such molecules inhibit the TG2-regulated pathways, reverse drug resistance and/or inhibit metastasis of cancer cells and are generally useful to treat cancer including, but not limited to, breast, brain, ovarian, prostate, pancreatic, lung, colorectal or esophageal cancer, and/or melanoma, or neuroblastoma.

As such, further provided herein are methods of treating drug resistance and/or metastasis of cancer cells comprising the step of administrating to a patient in need thereof a compound of Formula I, Formula II or Formula III, as described herein, or even more specifically a compound shown in Table 1 below. Also provided are methods of inhibiting TG2 expression and/or induction of EMT by administrating to a patient in need thereof a compound of Formula Formula II or Formula III as described herein, or more specifically a compound shown in Table 1 below.

BRIEF DESCRIPTION OF THE SEVERAL VIEWS OF THE DRAWINGS

FIG. 1A are phase-contrast images of MCF10A-vec and MCF10A-TG2 cells after 48 hr culture in medium. Magnification 10×. FIG. 1B is an immunoblot showing relative expression of TG2 in MCF10A-vec (10A-vec) and MCF10A-TG2 (10A-TG2) cells. FIG. 1C shows immunofluorescence due to TG2 and EMT markers in MCF10A-vec (top panel) and MCF10A-TG2 (bottom panel) cells. Green fluorescence shows the expression and localization of indicated proteins and DAN (blue) staining shows the nuclei. FIG. 1D provides an immunoblot analysis of the indicated EMT markers in MCF10A-vec and MCF10A-TG2 cells. Expression of epithelial cell markers (E-cadherin, β-catenin) and mesenchymal cell marker (N-cadherin, fibronectin, and vimentin) was examined by immunoblotting. Multiple stable polyclones were established from MCF10A cells and most experiments were repeated with different polyclones.

FIG. 2A shows a real time RT-PCR array showing the changes in relative expression of EMT associated genes in MCF10A-TG2 cells in comparison to MCF10A-vec cells. Y-axis denotes the fold-expression and x-axis denotes the genes. The expression of GAPDH, β-actin and 18S ribosomal RNA was used to normalize variable template loading. FIG. 2B shows RT-PCR analysis for EMT-related transcripts was used to validate their expression in MCF10A-vec and MCF10A-TG2 cells. FIG. 2C-D is the RT-PCR (FIG. 2C) and immunoblot (FIG. 2D) analysis was used to validate the expression of transcription factors Snail1, Zeb1 and Twist1 in MCF10A-vec and MCF10A-TG2 cells.

FIGS. 3A, 3B, 3C and 3D show TG2-induced EMT confers invasive and tumorigenic phenotype. FIG. 3A shows the results of a Transwell-Matrigel invasion assay performed with MCF10A-vec and MCF10A-TG2 cells. Cells that invaded though the Matrigel after 72 hr incubation were counted in five random microscopic fields under 20× magnification. Experiments were done three times in triplicate. Results shown are the number of invading cells per field±SEM. FIG. 3B is a graph represents average number of colonies formed from three independent experiments±SEM after 3 weeks' incubation of cells in soft agar. Images of colonies formed from a representative experiment after 3 weeks culture in soft agar are shown in right panel. Magnification 10×, FIG. 3C provides phase-contrast images of acinar structures (4 and 12 days) formed as a result of MCF10A-vec and MCF10A-TG2 cell culture in Matrigel-coated glass-slide chambers for indicated time periods. Inset, amplified view of individual MCF10A-TG2 cells invading the surrounding Matrigel (indicated by the arrow), FIG. 3D shows a loss of basement membrane integrity in MCF10A-TG2 acini. MCF10A cells were cultured in Matrigel-coated chambers for 4 and 12 days and immunostained for laminin V (green) and DAPI (blue). Representative images from two independent experiments with similar results are shown. Magnification 20×.

FIGS. 4A, 4B, 4C and 4D show TG2 induces the activation of TGF-β non-canonical signaling pathway. FIG. 4A show supershift assay data for NIT-KB activity using EMSA with the nuclear extracts prepared from indicated cells. Nuclear extracts were incubated with an anti-p65 antibody and anti-p50 antibody, or nonradioactive (cold) or mutant NF-κB oligonucleotides and examined for DNA binding. Nuclear extract of KMB cells treated with TNF-β (+TNF) were used in parallel as positive control. FIG. 4B is an immunoblot analysis showing the level for pAKT(S473) and pFAK(Y397) in MCF10A-vec and MCF10A-TG2 cells. FIG. 4C are phase-contrast images of MCF10A cells transfected with control-shRNA or TG2-shRNA and incubated in medium alone (−) or medium containing 2.5 ng/ml recombinant TGF-β (+). After 12 days incubation, TGF-β-treated MCF10A-control-shRNA cells showed induction of EMT but not TG2-shRNA transfected cells. FIG. 4D is an immunoblot analysis for expression of TG2, the epithelial marker E-cadherin and the mesenchymal marker fibronectin in MCF10A-control-shRNA and MCF10A-TG2-shRNA cells in response to TGF-β treatment for 12 days.

FIGS. 8A and 8B show neoexpression of TG2 renders LnCap cells independent of androgen for growth and survival.

FIGS. 10A, 10B, 10C and 10D show TG2 expression promotes EMT in LNCaP cells.

FIGS. 11A, 11B and 11C show TG2 expression downregulates androgen receptor expression in LNCaP cells.

FIGS. 12A and 12B provide data that show the inhibition of TG2 in AR negative prostate cancer cells (DU145) attenuate their invasiveness and renders them sensitive to chemotherapy.

FIG. 13 shows that R580K mutant of TG7 is incompetent of inducing EMT functions in MCF10A cells.

FIGS. 18A and 1813 show that TG2 expression but not the R580 mutant promotes mammosphere formation in mammosphere growth medium.

FIG. 19 shows the mesenchymal nature of the cells confirmed by evidence of accumulation of stress fiber in the MCF10A-TG2 cells.

FIG. 20 shows TG2-induced alterations are not unique to the MCF10A cells, as similar changes in the morphology, E-cadherin, and Fibronectin expression became evident in another human mammary epithelial cell line (MCF-12A) in response to TG2 expression.

FIGS. 26A, 26B, 26C and 26D show expression and characterization data of 162 constructs in MCF10A cells. Specifically, FIG. 26A is a representative immunoblot of cell lysates showing TG2 expression in MCF10A sublines stably transfected with vector alone (Vec), wild-type (TG2-WT), transamidase-inactive (TG2-C277S) and GTP-binding inactive (TG2-R580A) TG2 construct. Membrane was stripped and reprobed with anti-actin antibody to ensure even protein loading. FIG. 26B shows immuniofloresence staining for TG2 and DAFT staining for the nuclei in indicated MCF10A sublines. Magnification 10×. FIG. 26C shows in situ transamidation activity of TG2 constructs was studied by preincubating indicated MCF10A cells with 1 mM BPA overnight, followed by 8 hr incubation in medium alone (−) or medium containing 8 μM. (+) calcium ionophore, A23187. Cells were harvested and BPA-conjugated cellular proteins detected by immunoblotting type assay, using HRP-conjugated streptavidin as a probe. Membrane were reprobed with anti-TG2 and β-actin antibody to ensure even loading and levels of TG2 expression. FIG. 26D is an immunoblot showing GTP-binding ability of different TG2 constructs. Pull-down experiments were performed with GTP-agarose beads incubated for either 30 min (30') or overnight (o/n) to evaluate GTP-binding affinities for indicated TG2 forms. Input shows the level of TG2 expression in MCF10A cell lines expressing different TG2 constructs FIGS. 27A, 27B and 27C show GTP-binding activity is critical for TG2-induced epithelial-to-mesenchymal transition. Specifically, FIG. 27 A shows phase-contrast images of MCF-10A cells expressing the lentiviral vector alone (Vec) or vector containing WT or mutant TG2 constructs (TG2-C277S and TG2-R580A) were taken after 48 hr culture in puromysine selection medium. Magnifications 10×. FIG. 27B shows the immunoblot analysis of control (Vec) and TG2 expressing MCF10A cells. Expression of epithelial cell markers (E-cadherin, β-catenin) and mesenchymal cell marker (N-cadherin, fibronectin, and vimentin) were examined by immunoblotting. FIG. 27C shows immunofluorescence due to expression of EMI markers in MCF10A sublines. Cells were counterstained with DAFT for nuclear staining FIG. 28B provides the RT-PCR analysis and FIG. 28C provides an immunoblot analysis which were both performed to validate the expression of transcription factors Snail1, Zeb1 and Twist1 in Different MCF10A sublines FIGS. 29A through 29E show GTP-binding defective TG2 fails to promote survival, invasion and drug resistance. Specifically, FIG. 29A shows the Transwell-Matrigel invasion assay that was performed with indicated MCF10A sublines. Cells that invaded though the Matrigel after 72 hr incubation were counted in five random microscopic fields under 20× magnification. Experiments were done three times in triplicates. Results shown are the average number of invading cells per field±SEM. FIG. 29 B shows sensitivity of indicated MCF10A sublines to doxorubicin. Quadruplicate wells in 96-well plates, containing 2,000 cells per well in 0.2 ml of the complete medium (10% FCS) were either left untreated or treated with indicated concentrations of doxorubicin. Two days after the treatment, viable cells remaining in wells were determined by MTS reduction test, and percent cell viability was calculated. Experiments were repeated at least three times with similar results. Bars, mean of quadruplicate values from a representative experiment lines, SD. FIG. 29C shows the average number of colonies formed from three independent experiments±SEM after 3 weeks' incubation of cells in soft agar. Images of colonies formed from a representative experiment after 3 weeks culture in soft agar are shown in right panel. Magnification 10×. FIG. 29D are phase-contrast images of acinar structures (4 and 12 days) formed as a result of indicated MCF10A cells cultured in Matrigel-coated glass-slide chambers for indicated time periods. FIG. 29E shows the loss of basement membrane in MCF10A sublimes expressing W1 or C277S TG2 after 12 days culture in Matrigel-coated chambers. Structures thus obtained were immunostained for laminin V (green) and DAPI (blue). Representative images from two independent experiments with similar results are shown. Magnifications 20×.

FIGS. 30A. 30B and 30C show TG2 requires functional GTP-binding domain to activate NF-κB and Akt signaling. Specifically, FIG. 30A shows the results of the electrophoretic mobility shift assay for NF-κB activity in the nuclear extracts prepared from indicated MCF-10A cells. FIG. 30B shows the results of the immunoblot analysis for different epithelial and mesenchymal marker proteins in TG2-WT cells before and after transfection with either control or p65-specific siRNA. FIG. 30C show an immunoblot analysis showing the levels of total and pAKT(S473) and pFAK (Y397) in control and TG2-transfected MCF10A sublines.

FIG. 31A through 31F show GTP-binding function of 162 is essential for promoting the stern cell phenotype. Specifically FIG. 31A shows the FACS analysis for the mammary stem cell antigenic markers CD44 and CD24 in MCF10A cells expressing catalytically inactive (C277S) and GTP-binding defective (R580A) forms of TG2. FIG. 31B provides the phase-contrast images of mammospheres formed by indicated MCF10A cells (upper panel). In vitro quantification of mammospheres formed by TG2-C2775 and TG2-R580A transfected MCF-10A cells (lower panel). The data shown are the number of mammospheres formed/1000 seeded cells ±SEM. FIG. 31C shows in vitro quantification of mammospheres formed by TG2-C277S expressing MCF10A cells after different passages (M1 to M4). FIG. 31D provides in vitro quantification of mammospheres formed by TG-2-R580A transfected MCF10A cells after different serial passages (M1 to M4). The data shown are average number of mammospheres formed/1000 seeded cells±SEM from triplicate values from a representative experiment. FIG. 31E provides the phase-contrast images of the differentiated mammospheres following, their 12-days culture in Matrigel. FIG. 31F provides the differentiated structures were immunostained for luminal marker Muc1 (red), basal marker CD49f/ integrin α6 (green) and for nuclei with DAPI (blue).

FIGS. 32A1, 32A2, 32B1, 32B2, 32C1, 32C2, and 32D1, 32D2 represent activity data of compounds MZ-1, MZ-3, MZ-8 and MZ-10 as presented herein.

FIGS. 33A1 and 33A2 represent activity data of compound, MZ-4 as presented herein.

DETAIL DESCRIPTION OF THE INVENTION

Figure 1B:
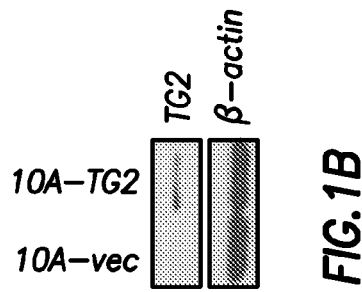
FIGS. 1A, 1B, 1C and 1D show TG2 induces EMT in normal mammary epithelial cells. MCF10A cells were stably transfected with vector alone (MCF10A-vec) or lentiviral-TG2 construct (MCF10A-TG2).

Over expression of TG2 in normal and cancer epithelial cells is associated with loss of E-cadherin, cellular polarity, upregulation of mesenchymal molecular markers, such as fibronectin, vimentin, N-cadherin and transcriptional repressors of E-cadherin, such as Snail1, Zeb1, Zeb2 and Twist1. Furthermore, TG2 is a downstream mediator of tumor growth factor-β (TGF-β)-induced EMT. Aberrant TG2 expression signals the onset of EMT in epithelial cells, contributes to their increased survival and metastatic potential and hence represents a promising therapeutic target for metastatic cancer.

Tissue transglutaminase (TG2, EC 2.3.2.13) is a unique member of the transglutaminase family of enzymes. In addition to catalyzing $Ca_{2+}$-dependent post-translational modification of proteins by inserting irreversible ϵ(γ-glutamyl) lysine crosslinks between substrate proteins, it can catalyze calcium-independent hydrolysis of guanosine 5'-triphosphate (GTP), the protein disulfide isomerase reaction, and serine/ threonine kinase activity. TG2's ability to hydrolyze GTP enables it to serve as a signaling molecule and activates a downstream target, phospholipase C. Although predominantly a cytosolic protein. TG2 can also be secreted outside the cell where it regulates cell-matrix interactions; can translocate to the nucleus where it associates with pRb, p53, and histones to regulate certain cellular functions, TG2 can be expressed on the cell membrane in association with β integrins where it serves as a co-receptor for integrin-mediated binding to fibronectin (Fri). Cell surface TG2 can affect important cell functions such as attachment, spreading, motility, and survival. US 2008/0279844 A1 at [0003], incorporated herein by reference.

Involvement of TG2 in apoptosis has been well established. Overexpression of TG2 results in either spontaneous apoptosis of cells or rendering cells highly sensitive to apoptosis-inducing agents. By contrast, evidence now indicates that increased expression of TG2 may prolong cell survival by preventing apoptosis. Several reports have documented elevated expression of TG2 in various cancer types. We and others have reported that the basal expression of TG2 in several tumor cells and tumor cell lines is elevated when they become resistant to chemotherapeutic drugs. An increased TG2 expression was associated with an increased resistance to chemotherapeutic drugs and other apoptosis-inducing stimuli. Inhibition of TG2 by small interfering RNA (siRNA) can reverse the sensitivity of drug-resistant MCF-7 breast cancer cells to doxorubicin and rendered them sensitive to serum-withdrawal-induced apoptosis. Tumor cells from metastatic sites and cell lines with metastatic potential express high basal levels of TG2. Elevated expression of TG2 in pancreatic cancer cells has been detected. As such, TG2 expression plays a role in the development of drug resistance and metastatic phenotypes in cancer cells. US 2008/0279844 A1 at [0004], incorporated herein by reference.

Different cancer cell types including breast, melanoma, pancreatic, ovarian, oesophageal, colorectal, lung, and brain have linked TG2 expression with drug resistance and metastatic phenotypes. We showed that ectopic expression of TG2 results in increased invasion of cancer cells through the Matrigel, strong attachment to ECM-coated surfaces, increased resistance to apoptosis, and activation of cell survival signaling pathways. Conversely, downregulation of TG2 by siRNA or its inhibition by pharmacologic agents inhibited the invasion of cancer cells through the matrigel, reversal of drug resistance, increased sensitivity to stressors and spontaneous death of cells via autophagy. These observations have been confirmed in patients' tumor samples. For example, Kaplan-Meier curve has a strong correlation between patient survival and TG2 expression. Similarly, knock down of TG2 in a PDAC cells caused strong retardation in xenograft growth in nude mouse model. US 2008/0279844 A1 at [0007], incorporated herein by reference.

TG2 expression promotes cell survival and invasive functions in cancer cells by associating and constitutively activating several key regulatory proteins. For example, TG2 by associating with beta-1, -3, -4, and -5 members of the integrin family of proteins could promote stable interaction of cells with the extracellular matrix ligands resulting in activation of cell survival pathways. Similarly, TG2 expression leads to constitutive activation of the nuclear transcription factor, NF-κB as a result of its binding to the p65 subunit of NF-κB. Thirdly, TG2 expression results in constitutive activation of the focal adhesion kinase (FAK) and its downstream PI3K/Akt cell survival signaling pathways by associating with FAK protein. Also, TG2 expression in cancer cells effectively downregulate the expression and function of the tumor suppressor PTEN protein. Inhibition of TG2 expression, therefore, inhibits/blocks simultaneously various pathways (integrin-mediated, FAK, NF-κB, and PTEN-dependent) that are critical for the successful survival of cancer cells. US 2008/0279844 A1 at [0008], incorporated herein by reference; See also, US 2008/0279844 A1 at [0214] to [0220], incorporated herein by reference.

We have further discovered that aberrant expression of TG2 serves as an oncogenic signal in mammary and prostate epithelial cells and promotes EMT and stem cell-like phenotype. Thus, over expression of TG2 in MCF10A, MCF12A, and LnCaP cells is associated with increased invasiveness, loss of cell polarity, increased cell survival, and anchorage-independent growth. EMT marks the conversion of polarized and immotile epithelial cells to highly motile cells during embryogenesis and wound healing. It is characterized by the loss of cell-cell adhesion, apical basal cell polarity, and increased cell motility.

As noted above, in tumors, the EMT plays an important role during tumor progression and development of metastasis. In addition, TG2-induced. EMT can promote anchorage-independent growth and tumorigenic potential of epithelial cells. Our in vitro data clearly support that over expression of TG2 in mammary and prostate epithelial cells is sufficient to induce aggressive phenotype. Hence, TG2 modulators provide a therapeutic target for treating drug resistant and metastatic tumors that account for greater 90% cancer related deaths. Similarly, inhibition of TG2 can be used to inhibit the pathogenesis of inflammatory degenerative fibrotic disorders (lung fibrosis, renal fibrosis, liver fibrosis, pancreatitis, etc.).

In the case of the TG2 intracellular protein, aberrant TG2 expression signals the onset of EMT and stem cell like characteristics in epithelial cells, contributing to cell survival and metastatic potential. When TG2, an intracellular protein, is mutated at position 580 (an arginine), GTP binding activity is absent. The arginine at position 580 (R580) of TG2 is essential for binding to GTP as well as for its hydrolysis. The ability of TG2 to bind and hydrolyze GTP has been implicated in downstream signaling induced in response to certain agonists after binding to their cognate receptors (oxytocin, adrenergic receptor, etc. . . . ).

Knowing the importance of GTP binding site of TG2 in promoting EMT, different drug products are provided herein to block GTP-binding and the associated effects. First, synthetic peptides, permeable through the cell membrane, which compete with GTP-binding site of TG2 to inhibit its EMT/stemness promoting ability are provided herein. The peptides may be as large as a 30+ mer (the binding sequence) peptide or as small as a 5-mer peptide length, capable of competing with TG2 for the GTP binding site of TG2. Such peptide sequences useful in inhibiting TG2 include the sequences, SEQ ID NO. 1 to 33 as shown and provided in the attached sequence listing filed herewith. Generally, amino acids that flank on each side of the R580 residue may be useful including longer sequences.

A palmitate or other fatty-acid residue such as can be conjugated or otherwise attached to the N-terminal amino acid of the synthetic peptide to enhance its cellular uptake. One example of such conjugation is Palmitate-NSYLLAE-R (580)-DLYLENPEIK. The residues of other fatty acids may be useful in enhancing the cellular uptake of the peptides of sequences shown in the sequence listing and identified as SEQ ID NOs. 1-33. Such fatty acids include myristoleic acid, myristic acid, palmitic acid, stearic acid, lauric acid, sapienic acid, oleic acid, linoleic acid, archidonic acid, eicosapentaenoic acid, erucic acid, docosahexaeonic acid and the like.

Second, small molecule inhibitors to block GTP-binding site of TG2 critical for inducing EMT and stem cell phenotype in epithelial cells are proposed herein. Molecular designs for new small-molecule inhibitors of TG2 can take advantage of the positively charged residues (Arg) on TG2 found at positions 476, 478 and 580 as shown in the 162 sequence, SEQ ID NO. 34. Interestingly, in all potential low-energy docking poses, the interaction with at least two of the three arginines (including Arg 580) of 162 binding site can be observed. This should, in principle, ensure a certain degree of specificity for TG2, because the presence of three arginines differentiates TG2 binding site from other GTP-binding proteins.

Furthermore, as described herein, we have discovered that transamindation activity of TG2 is not essential for promoting TG2 associated oncogenic functions. For example, expression of catalytically inactive 102 (i.e., TG2-C277S and TG2-W241A mutants) is as effective as the wild-type TG2 in inducing EMT/CSC in mammary epithelial cells. In contrast, overexpression of a GTP-binding-deficient mutant (i.e. TG2-R580A) was completely incompetent in this regard. Furthermore, TG2-dependent activation of the proinflammatory transcription factor, NF-κB, is deemed essential for promoting the EMT/CSC phenotype in mammary epithelial cells.

As such, small molecule inhibitors that block GTP-binding pocket of TG2 include a compound of the structural formula, Formula I:

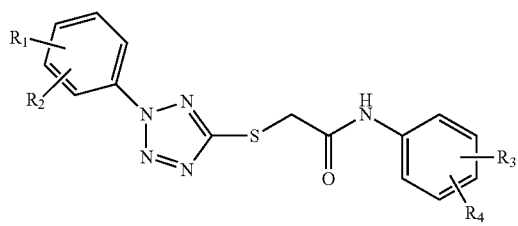

wherein $R_1$, $R_2$, $R_3$ and $R_4$ are each independently hydrido, halo, alkyl, alkoxy, amino, alkylamino, alkylcarbonylamino, dialkylamino, carbamoyl, nitro, cyano, perfluoroalkyl, trifluoromethylalkyl, hydroxyl, thiol, hydroxycarbonyl, or alkyl carbonyl.

Additional small molecule inhibitors that block GTP-binding pocket of TG2 include compound of the structural formula, Formula II:

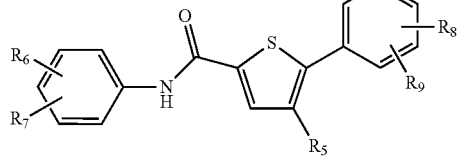

wherein $R_5$ is H or methyl, and $R_7$, $R_7$, $R_8$ and $R_9$ are independently selected from hydrido, halo, alkyl, alkoxy, amino, alkylamino, alkylcarbonylamino, dialkylamino, carbamoyl, nitro, cyano, perfluoroalkyl, trifluoromethylalkyl, hydroxyl, thiol, hydroxycarbonyl, alkylcarbonyl, or may constitute a 5- or 6-membered heterocyclic ring containing one or two oxygen atoms.

Further small molecule inhibitors that block GTP-binding pocket of TG2 include a compound of the structural formula, Formula

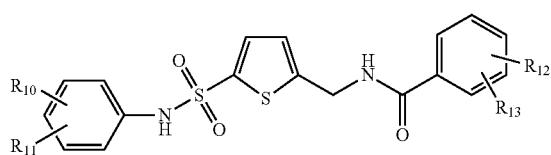

wherein $R_{10}$, $R_{11}$, $R_{12}$ and $R_{13}$ are independently selected from hydrido, halo, alkyl, alkoxy, amino, alkylamino, alkylcarbonylamino, dialkylamino, carbamoyl, nitro, cyano, perfluoroalkyl, trifluoromethylalkyl, hydroxyl, thiol, hydroxycarbonyl, alkylcarbonyl.

These small molecule inhibitors can inhibit the TG2-regulated pathways, reverse drug resistance, inhibit metastasis of cancer cells and/or are useful in treating cancers including ovarian, prostate, melanoma, breast, pancreatic, brain, lung, colorectal, and oesophageal.

The preparation of compounds of Formula I may be accomplished through the synthetic scheme outlined in Scheme I immediately wherein 2-(2H-tetrazol-5-ylthio)-acetic acid is coupled with an appropriate aniline through methodology known to those skilled in the art, either via formation of an acid chloride followed by treatment with the aniline, or through coupling with a carbodiimide reagent such as dicyclohexylcarbodiimide or the water-soluble variant, or by using carbonyldiimidazole as the activating reagent for the acid, or through similar means. The tetrazole is then N-arylated by reaction with the appropriate substituted an halide (as exemplified for the aryl bromide) under Ullman conditions utilizing copper metal, copper iodide, or copper (II) acetate as a catalyst, or via Buchwald-Hartwig conditions employing a palladium catalyst such as Pd(dba)$_2$, Pd$_2$(dba)$_3$, palladium acetate, a base such as potassium carbonate of cesium carbonate, and a ligand such as BINAP, triphenylphosphine, tri-orthotolylphosphine, or tributyl phosphine, in a solvent such as toluene or tetrahydrofuran, affording compounds of Formula I.

Scheme I as shown below:

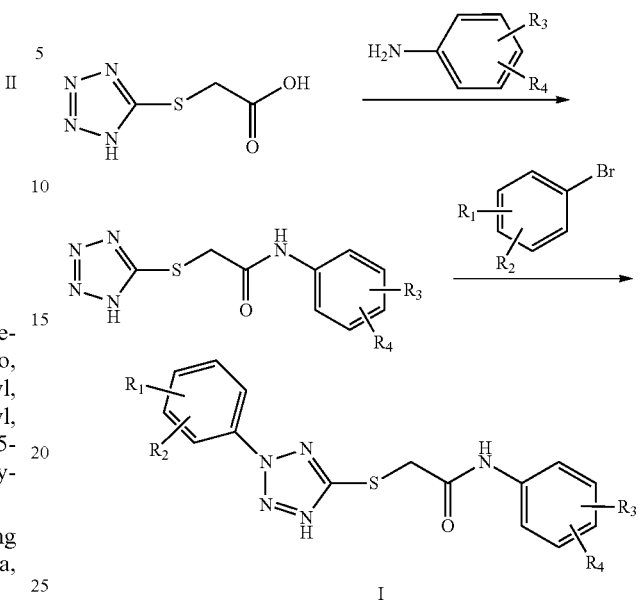

The preparation of compounds of Formula II may be accomplished through the synthetic scheme outlined in Scheme II wherein 5-Bromo-2-thiazolecarboxylic acid ($R_5$=H) or 5-bromo-4-methyl-2-thiazolecarboxylic acid ($R_5$=methyl) acid is coupled with an appropriate aniline through methodology known to those skilled in the art, either via formation of an acid chloride followed by treatment with the aniline, or through coupling with a carbodiimide reagent such as dicyclohexylcarbodiimide or the water-soluble variant, or by using carbonyldiimidazole as the activating reagent for the acid, or through similar means. Thereupon the bromothiophene is subjected to a Suzuki coupling with an appropriate arylboronic acid employing Pd(OAc)$_2$, Pd$_2$(dba)$_3$, Pd(Ph$_3$)$_4$ and a base such as potassium carbonate or cesium carbonate in a solvent such as toluene to afford compounds of Formula II.

Scheme II is shown below:

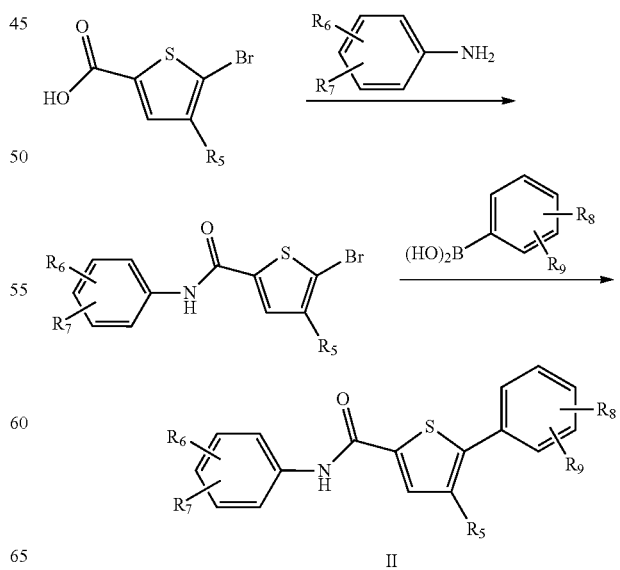

The preparation of compounds of Formula III may be accomplished through the synthetic scheme outlined in Scheme III immediately below wherein carbamic acid, [[5-(chlorosulfonyl)-2-thienyl]methyl]-, phenylmethyl ester is reacted with an appropriate aniline to yield a sulfonamide. Deprotection of the Cbz protecting group with hydrogen and palladium on carbon affords the amine which is coupled with an appropriate carboxylic acid through methodology known to those skilled in the art, either via formation of an acid chloride followed by treatment with the aniline, or through coupling with a carbodiimide reagent such as dicyclohexylcarbodiimide or the water-soluble variant, or by using carbonyldiimidazole as the activating reagent for the acid, or through similar means to yield compounds of Formula III. Scheme III is shown below:

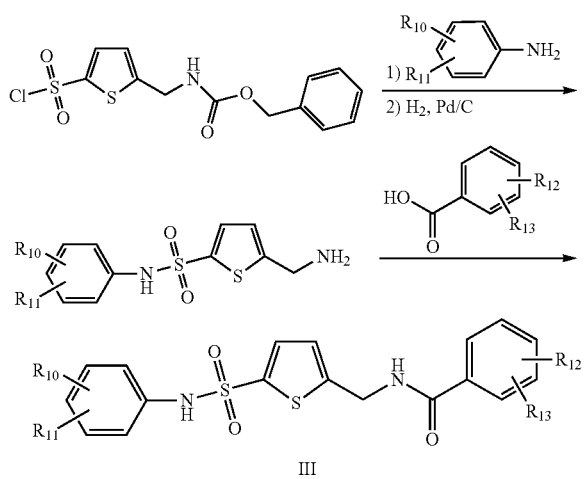

More specifically and as discussed in Example II below, we carried out studies to determine which of the two well-characterized activities of TG2 (the protein cross-linking activity or the GTP-binding activity) is responsible for promoting the oncogenic functions. There is evidence that a small subset of cells within a tumor, termed cancer stem cells ("CSCs") or tumor initiating cells ("TICs") are responsible for sustained tumor growth. Here, we investigated which of the two well-characterized activities of TG2 could impact its ability to induce the EMT and stem cellness in mammary epithelial cells. As described herein, we employed TG2-C277S and TG2-W241A mutant as a transamidation inactive forms and TG2-580A mutant as GTP-binding deficient form.

The GTP-binding and transamidation activities of TG2 are mechanistically mutually exclusive and are regulated by GTP and calcium. The transamidase activity of TG2 is stimulated by $Ca^{2+}$ and inhibited by GTP, while GTPase activity is inhibited by $Ca^{2+}$. Orlowski, R. Z., et al., *NF-kappaB as a Therapeutic Target in Cancer*, Trends Mol. Med. August; 8(81: 385-9 (2002). Under physiological conditions, whether intracellular TG2 acts as a transamidase or GTPase is not well known. The current view that holds the support is that due to high GTP and low $Ca^{2+}$, TG2 exists as an inactive transamidase inside the cell, where it acts mainly as GTP-binding protein and converts GTP into GDP. This view is supported by our current results where TG2-WT expressing MCF10A cells faded to show any significant in situ activity under basal culture conditions.

In contrast, the GTP-binding inactive mutant (TG2-R580A), in contrast, showed some transamidase activity even under basal conditions. (FIG. 26). The transamidating in situ activity increased in response to calcium ionophore (A23187) treatment in TG2-wt and TG2-R580A transfected cells but not in transamidase inactive TG2-C277S expressing cells. Interestingly, the transamdiation activity of TG2 had no relevance to its ability to induce the EMT/CSC in mammary epithelial cells. Thus, catalytically inactive TG2-C277S and TG2-W241A forms of TG2 were as effective as the TG2-WT in inducing the EMT/CSC related changes, except some small subtle quantitative differences in the levels of certain inducible genes (FIG. 27). The GTP-binding inactive R580A mutant, on the other hand, was completely inactive in inducing the EMT/CSC-related changes despite, its high expression and transamidation activity. The expression of each of the three constructs was associated with decreased growth rates in MCF10A cells and was observed to be Vec>C277S>WT>R580A in that order.

TG2 has received considerable attention in recent years for its potential role in cancer cells. There is ample evidence supporting that metastatic and drug-resistant cancer cells express high basal levels of TG2. Mehta, K., et al., *Prognostic Significance of Tissue Transglutaminase in Drug Resistant and Metastatic Breast Cancer*, Clin Cancer Res 10: 8068-8076 (2004); Mangala, L. S., et al., *Tissue Transglutaminase Expression Promotes Cell Attachment, Invasion and Survival in Breast Cancer Cells*, Oncogene 26: 2459-2470 (2007); Kumar, A., et al., *Tissue Transglutaminase Promotes Drug Resistance and Invasion by Inducing Mesenchymal Transition in Mammary Epithelial Cells*, PLoS One 5: e13390 (2010); Kumar, A., et al., *Evidence that Aberrant Expression of Tissue Transglutaminase Promotes Stem Cell Characteristics in Mammary Epithelial Cells*, PLoS One 6: e20701 (2011); Verma, A., et al., *Tissue Transglutaminase-Mediated Chemoresistance in Cancer Cells*, Drug Resist Updat. 10: 144-51 (2007); Verma, A et al., *Therapeutic Significance of Elevated Tissue Transglutaminase Expression in Pancreatic Cancer*, Clin. Cancer Res. 14: 2476-2483 (2008); Hwang, J. Y., et al., *Clinical and Biological Significance of Tissue Transglutaminase in Ovarian Carcinoma*, Cancer Res. 68, 5849-5858 (2008); Yuan, L., et al., *Tissue Transglutaminase 2 Inhibition Promotes Cell Death and Chemosensitivity in Glioblastomas*, Mol Cancer Ther. 4: 1293-1302 (2005).

We found that stable expression of TG2 in normal and transformed mammary epithelial cells is associated with the induction of EMT and CSC, the phenotypes that are closely linked with the development of drug resistance and metastasis in cancer cells. Kumar, A., et al., *Evidence that Aberrant Expression of Tissue Transglutaminase Promotes Stem Cell Characteristics in Mammary Epithelial Cells*, PLoS One 6: e20701 (2011). These observations imply that aberrant expression of TG2 in cancer cells could promote drug resistance and metastasis by inducing EMT/CSC phenotype and hence could serve as a promising therapeutic target for reversing chemoresistance and inhibiting metastasis. Indeed, as a proof-of-concept the observations that inhibition of TG2 by siRNA, small molecule inhibitors or antisense RNA approach could render cancer cells sensitive to chemotherapeutic drugs and inhibit their invasiveness both in vitro and in animal models strongly supported such contention. Therefore, knowledge of TG2 domain/function that is essential for promoting the EMT/CSC is essential for rationale design of small molecule inhibitors for harnessing TG2-regulated events in cancer cells.

We investigated whether either or both of the two well-characterized activities of TG2 are essential for promoting the EMT/CSC in normal and transformed mammary epithelial cells. The data obtained shows that the transamidation activity of 162 is not essential for promoting the EMT/CSC in mammary epithelial cells. However, intervention of GTP-binding function could completely abrogate such oncogenic functions of TG2. Whether the failure of TG2-R580A mutant to support EMT/CSC phenotype is related to its inability to bind and hydrolyze GTP or is a consequence of the conformational change induced as a result of single amino acid substitution in position 580, remains to be determined.

As such, TG2-R580A mutant seems to acquire a more open and extended conformation compared to the TG2-WT form. Liu, S., et al., *Structural Basis for the Guanine Nucleotide-binding Activity of Tissue Transglutaminase and its Regulation of Transamidation Activity*, Proc Natl Acad Sci USA 99: 743-2747 (2002); Begg, G. E., et al., *Mechanism of Allosteric Regulation of Transglutaminase 2 by GTP*, Proc Natl Acad Sci USA 103:19683-19688 (2006). Therefore, the failure of TG2-R580A to promote EMT/CSC relates to its altered interaction with some signaling proteins rather than the inability to bind and hydrolyze GTP. In this context, our recent observation that interaction of TG2 with inhibitory protein IκB results in constitutive activation of NF-κB (Kumar et al., unpublished) is of interest. It is likely that TG2-R580A due to its extended conformation is unable to interact effectively with IκB. Indeed, the TG2-induced activation of NF-κB was significantly compromised in 16-R580A-transfected cells compared to the TG2-WT, TG2-C277S or TG2-W241A cells (FIG. 30). Constitutive activation of NF-κB is frequently associated with advanced stage cancers and is known to confer resistance to chemotherapy and promote metastasis by inducing EMT. Orlowski, R. Z., et al., *NF-kappaB as a Therapeutic Target in Cancer*, Trends Mol. Med. August; 8(8): 385-9 (2002); Karin, M. et al., *NF-kappaB in cancer: From Innocent Bystander to Major Culprit*, Nat Rev Cancer April; 2 (4):301-10 (2002).

Also, our data supports the notation that TG2-induced EMT in MCF10A cells could be reversed (MET) by inhibiting the NF-κB activity. Thus, inhibition of NF-kB by p65-shRNA reversed the mesenchymal phenotype to epithelial phenotype without any noticeable change in TG2 expression (FIG. 30B). Recently, Shao et al. noticed similar involvement of NF-κB activity in TG2-induced EMT, invasiveness and drug resistance in ovarian cancer cells. Shao, M., et al., *Epithelial-to-Mesenchymal Transition and Ovarian Tumor Progression Thawed by Tissue Transglutaminase*, Cancer Res. 69: 9192-201 (2009).

Overall, these observations suggest that open or closed conformation of TG2, which depends on the intracellular environments, is the major determining factor in TG2-induced promotion of cell survival or cell death signaling. Thus, transamidase-inactive closed conformation of 162 (due to GTP binding in presence of low $Ca^{2+}$) promotes cell survival processes by serving as scaffold protein and mediating protein-protein interactions. In this regard it is interesting to note that Protein 4.2 in red blood cells, which is the only catalytically inactive member of the transglutaminase family of proteins, primarily serves as a scaffold protein and promotes interaction with various membrane proteins like, ankryn, spectrin, and CD47. Given the structural similarities between TG2 and Protein 4.2, the primary function of TG2 in cancer cells is likely to serve as a scaffold protein rather than an enzyme. In this capacity, TG2 can promote protein-protein interactions resulting in constitutive activation of cellular events needed for increased cell survival and invasive function during advanced stage cancer.

These results provide the evidence that aberrant expression of TG2 in drug-resistant and metastatic cancer cells facilitates cell survival and invasive functions independent of its transamidation activity. Recently, Colak et al. reached a similar conclusion supporting that conformational state rather than transamidation activity of TG2 is an important determinant in cell survival signaling under glucose-deprived conditions. Colak, G., et al., *Cytosolic Guanine Nucleotide Binding Deficient Form of Transglutaminase 2 (R580a) Potentiates Cell Death in Oxygen Glucose Deprivation*, PLoS One 6:e16665 (2011). The novel oncogenic functions of TG2 create a suitable environment for small molecule inhibitors to intervene TG2-regulated processes and prevent the progression of cancer to more aggressive phenotype.

As such, we provide evidence herein that similar to the wild-type TG2, expression of transamidation inactive (C277S; W241A) mutants is able to induce the EMT/CSC in mammary epithelial cells. In contrast, the expression of GTP-binding deficient (R580A) TG2 mutant, failed to induce the EMT/CSC related changes. Cancer cells appear to utilize GTP-binding/signaling function of TG2 to acquire chemoresistance and metastatic phenotype.

As a result, small molecule inhibitors that inhibit TG2-regulated pathways and reverse EMT and CSC phenotype are provided herein. Specific small molecule inhibitors useful in various methods of treating cancer include those molecules shown in Table I immediately below.

TABLE 1

In Silico Binding to the TG2 Extended Conformation

| ID | Structure | Test Priority | Mol Weight | Docking Score |
|---|---|---|---|---|
| MZ-TG-1 | 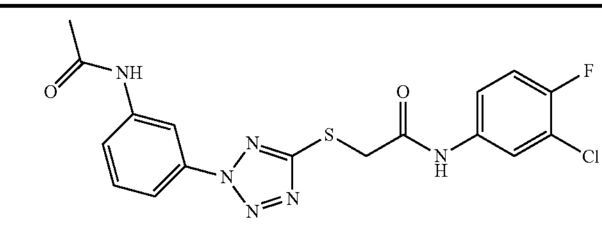 | High | 420.85 | −10.84 |
| MZ-TG-2 | 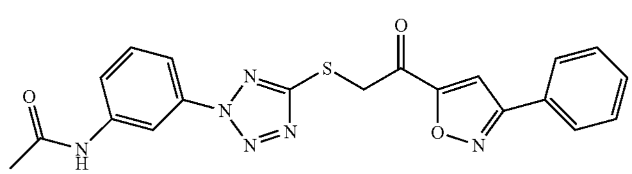 [SMILES: CC(=O)Nc1cccc(-n2nnc(SCC(=O)c3cc(-c4ccccc4)no3)n2)c1] | High | 420.445 | −10.78 |

TABLE 1-continued
In Silico Binding to the TG2 Extended Conformation
| ID | Structure | Test Priority | Mol Weight | Docking Score |
|---|---|---|---|---|
| MZ-TG-3 | 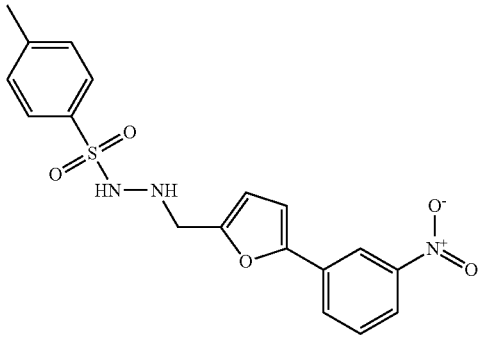 [SMILES: Cc1ccc(S(=O)(=O)NNCc2ccc(-c3cccc([N+](=O)[O-])c3)o2)cc1] | Medium | 387.41 | −10.68 |
| MZ-TG-4 | 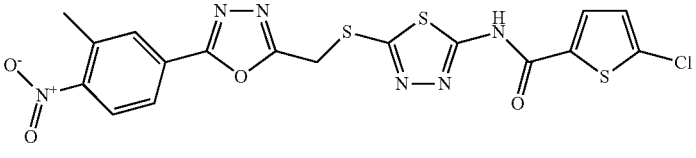 [SMILES: Cc1cc(-c2nnc(CSc3nnc(NC(=O)c4ccc(Cl)s4)s3)o2)ccc1[N+](=O)[O-]] | Medium | 494.96 | −10.25 |
| MZ-TG-5 | 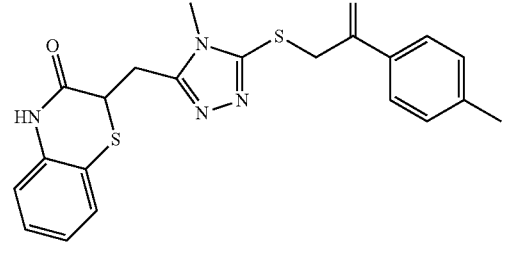 | Medium | 424.535 | −10.16 |
| MZ-TG-6 | 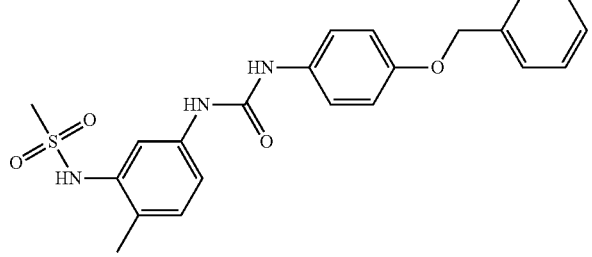 | Medium | 425.501 | −10.16 |
| MZ-TG-7 | 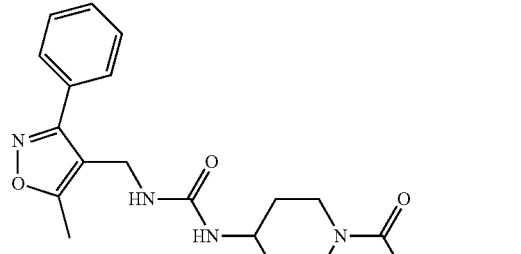 | Low | 448.521 | −10.15 |

TABLE 1-continued

In Silico Binding to the TG2 Extended Conformation

| ID | Structure | Test Priority | Mol Weight | Docking Score |
|---|---|---|---|---|
| MZ-TG-8 | 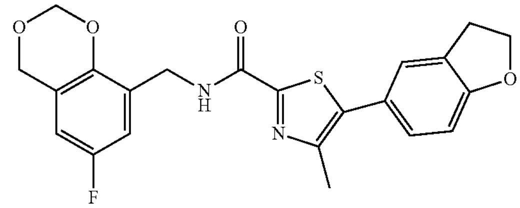 [SMILES: Cc1nc(C(=O)NCc2cc(F)cc3c2OCOC3)sc1-c1ccc2c(c1)CCO2] | Low | 426.46 | −10.11 |
| MZ-TG-9 | 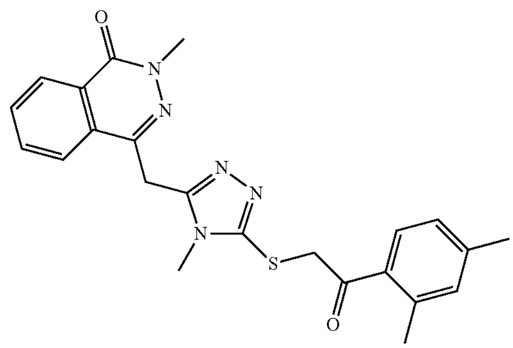 [SMILES: Cc1ccc(C(=O)CSc2nnc(Cc3nn(C)c(=O)c4ccccc34)n2C)c(C)c1] | Low | 433.527 | −9.93 |
| MZ-TG-10 | 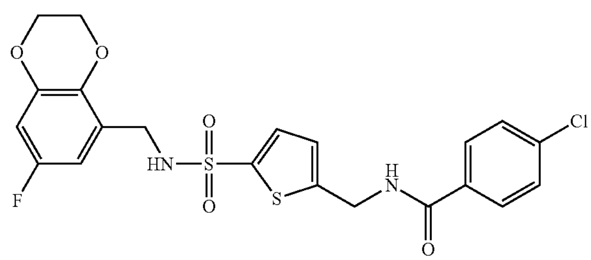 [SMILES: O=C(NCc1ccc(S(=O)(=O)NCc2cc(F)cc3c2OCCO3)s1)c1ccc(Cl)cc1] | Low | 496.96 | −9.85 |
| MZ-TG-11 | 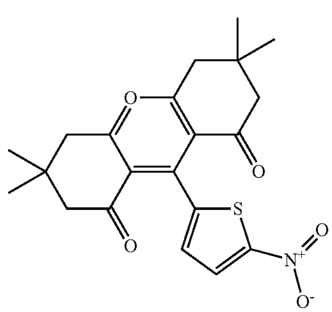 | Medium | 400.469 | −9.7 |
| MZ-TG-12 | 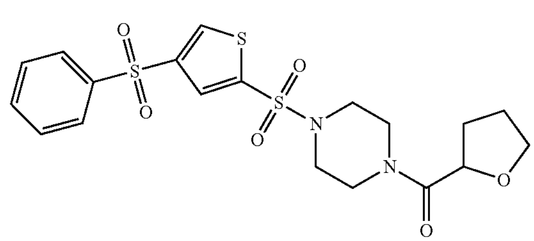 [SMILES: O=C(C1CCCO1)N1CCN(S(=O)(=O)c2cc(S(=O)(=O)c3ccccc3)cs2)CC1] | Low | 470.58 | −9.64 |

TABLE 1-continued

In Silico Binding to the TG2 Extended Conformation

| ID | Structure | Test Priority | Mol Weight | Docking Score |
|---|---|---|---|---|
| MZ-TG-13 | 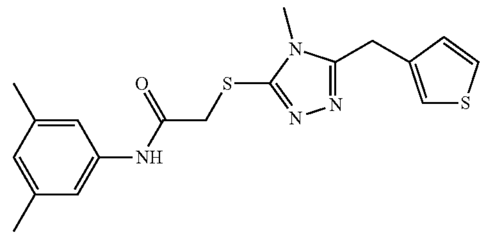 [SMILES: Cc1cc(C)cc(NC(=O)CSc2nnc(Cc3ccsc3)n2C)c1] | Medium | 372.502 | −9.6 |
| MZ-TG-14 | 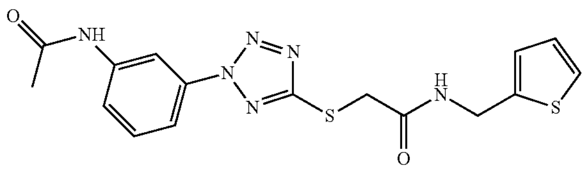 [SMILES: CC(=O)Nc1cccc(-n2nnc(SCC(=O)NCc3cccs3)n2)c1] | Low | 388.461 | −9.54 |
| MZ-TG-15 | 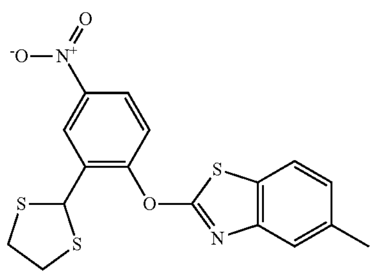 | Low | 390.489 | −9.5 |
| MZ-TG-16 | 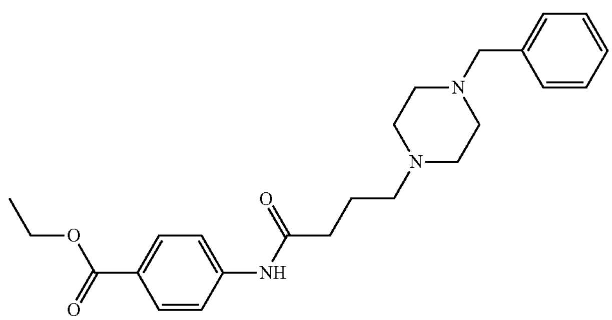 [SMILES: CCOC(=O)c1ccc(NC(=O)CCCN2CCN(Cc3ccccc3)CC2)cc1] | Medium | 409.527 | −9.43 |
| MZ-TG-17 | 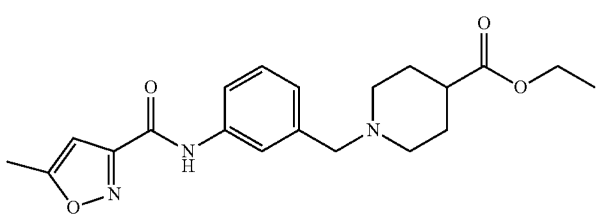 [SMILES: CCOC(=O)C1CCN(Cc2cccc(NC(=O)c3cc(C)on3)c2)CC1] | High | 371.43 | −9.4 |
| MZ-TG-18 | 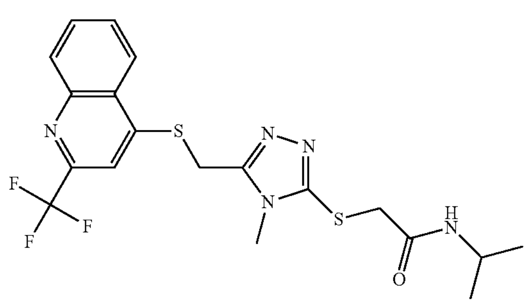 [SMILES: CC(C)NC(=O)CSc1nnc(CSc2cc(C(F)(F)F)nc3ccccc23)n1C] | Medium | 455.515 | −9.32 |

TABLE 1-continued

In Silico Binding to the TG2 Extended Conformation

| ID | Structure | Test Priority | Mol Weight | Docking Score |
|---|---|---|---|---|
| MZ-TG-19 | 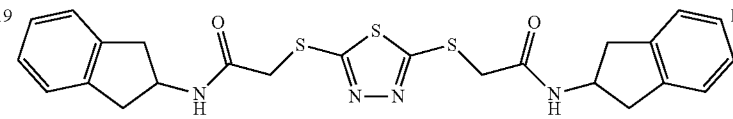 | Medium | 496.659 | −9.23 |
| MZ-TG-20 | 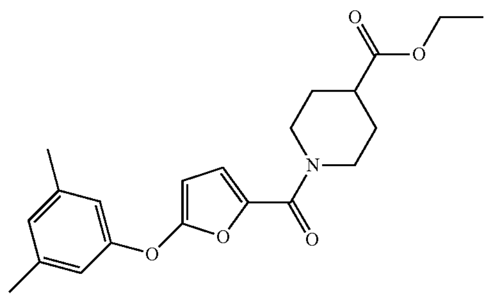 [SMILES: CCOC(=O)C1CCN(C(=O)c2ccc(Oc3cc(C)cc(C)c3)o2)CC1] | Low | 371.432 | −9.2 |
| MZ-TG-21 | 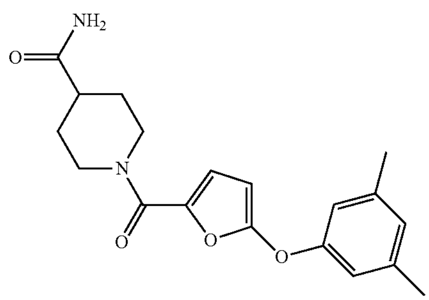 [SMILES: Cc1cc(C)cc(Oc2ccc(C(=O)N3CCC(C(N)=O)CC3)o2)c1] | High | 342.394 | −9.17 |
| MZ-TG-22 | 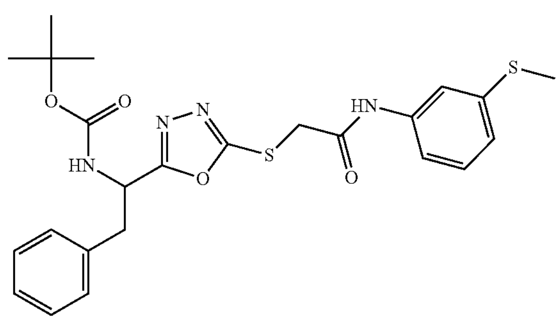 [SMILES: CSc1cccc(NC(=O)CSc2nnc(C(Cc3ccccc3)NC(=O)OC(C)(C)C)o2)c1] | High | 500.63 | −9.15 |
| MZ-TG-23 | 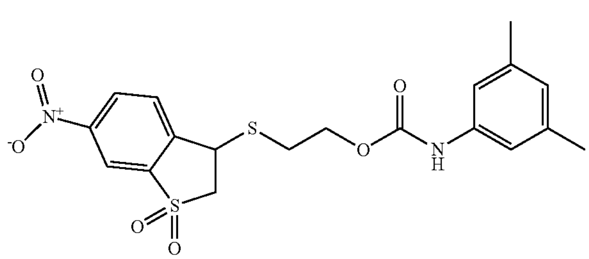 | Low | 436.497 | −9.11 |

TABLE 1-continued

In Silico Binding to the TG2 Extended Conformation

| ID | Structure | Test Priority | Mol Weight | Docking Score |
|---|---|---|---|---|
| MZ-TG-24 | 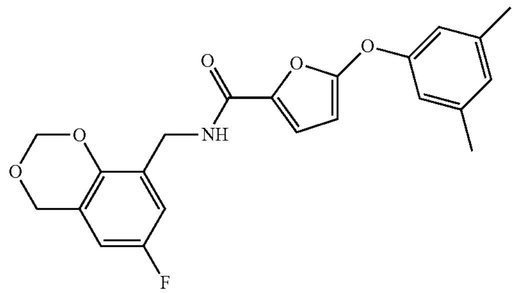 [SMILES: Cc1cc(C)cc(Oc2ccc(C(=O)NCc3cc(F)cc4c3OCOC4)o2)c1] | Low | 397.402 | −9.03 |
| MZ-TG-25 | 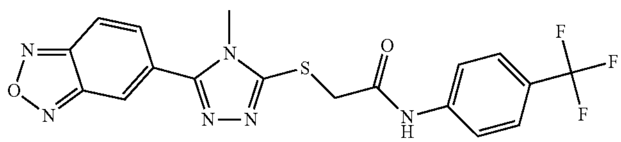 [SMILES: Cn1c(SCC(=O)Nc2ccc(C(F)(F)F)cc2)nnc1-c1ccc2nonc2c1] | Low | 434.395 | −8.99 |

TG2 is structurally and functionally a complex protein implicated in such diverse processes as inflammation, wound healing, celiac disease and cancer. Kim, D. S., et al., *Reversal of Drug Resistance in Breast Cancer Cells by Transglutaminase 2 Inhibition and Nuclear Factor-Kappab Inactivation*, Cancer Res. 66:10936-10943 (2006) Siegel, M., et al., *Transglutaminase 2 Inhibitors and their Therapeutic Role in Disease States*, Pharmacol Ther. 115: 232-245 (2007). TG2 is expressed in many different cancers found in different parts of the body including breast, brain, pancreatic, prostate, lung, ovarian, gastrointestinal tract, esophagus and skin (melanoma). Fok, J. Y., et al., *Implications oh Tissue Transglutaminase Expression in Malignant Melanoma*, Mol. Cancer. Ther. 5: 1493-1503 (2006); Verma A., et al., *Increased Expression of Tissue Transglutaminase in Pancreatic Ductal Adenocarcinoma and its Implications in Drug Resistance and Metastasis*, Cancer Res. 66: 10525-10533 (2006); Yuan, L., et al., *Tissue Transgluaminase 2 Expression in Meningiomas*, J Neurooncol. 90: 125-32 (2008); Chanbra. A., et al., *Tissue Transglutaminase Promotes or Suppresses Tumors Depending on Cell Context*, Anticancer Res. 29: 1909-1919 (2009).

Furthermore, as noted herein, TG2 expression in cancer cells is associated with increased resistance to chemotherapy, metastasis, and poor patient outcomes. Verma, A., et al. *Tissue Transglutaminase-Mediated Chemoresistance in Cancer Cells*, Drug Resist Updat. 10: 144-51 (2007); Hwang, J. Y., et al., *Clinical and Biological Significance of Tissue Transglutaminase in Ovarian Carcinoma*, Cancer Res. 68, 5849-5858 (2008); Verma, A., et al., *Therapeutic Significance of Elevated Tissue Transglutaminase Expression in Pancreatic Cancer*, Clin. Cancer Res. 14: 2476-2483 (2008).

Hence, inhibition of TG2 by small interfering RNA (siRNA), antisense RNA, or small molecule inhibitors reversed the sensitivity of cancer cells to chemotherapeutic drugs and attenuated their invasion both in vitro and in animal models. Yuan, L., et al., *Tissue Transglutaminase 2 inhibition Promotes Cell Death and Chemosensitivity in Glioblastomas*, Mol Cancer Ther. 4: 1293-1302 (2005); Verma, A., et al., *Increased Expression of Tissue Transglutaminase in Pancreatic Ductal Adenocarcinoma and its Implications in Drug Resistance and Metastasis*, Cancer Res. 66: 10525-10533 (2006); Verma, A., et al., *Therapeutic Significance of Elevated Tissue Transglutaminase Expression in Pancreatic Cancer*, Clin. Cancer Res. 14: 2476-2483 (2008); Hwang, J. Y., et al., *Clinical and Biological Significance of Tissue Transglutaminase in Ovarian Carcinoma*, Cancer Res. 68, 5849-5858 (2008).

As such, siRNA could be encapsulated into lipid-based nanoparticles (DOPC nanoliposomes), reaching effective doses in preclinical phases. DOPC nanoliposomes have demonstrated to be also effective in delivering siRNA and silencing oncoproteins, as well as, the expression of interleukin-8 in orthotopically growing tumors. The intellectual property process was initially disclosed in WO2008/063760. Such siRNA molecules are identified herein as SEQ ID NOs 35 to 86 which may be useful in the modulation and inhibition of the TG2 expression. Neutrally charged nanoliposomes could be used as gene delivery systems, to release TG2 short interfering RNA (siRNA) and therefore down-regulate TG2 expression in orthotopically growing pancreatic tumors. Also, molecular targets, not reachable by means of antibodies or other biological agents, could be inhibited through siRNA-therapeutic agents. Due to the fact that naked siRNA is unstable in plasma, an effective delivery to the target tissue is likely to require chemical modification. Nevertheless, stability methods used for increasing the bioavailability, makes naked siRNA therapeutic applications non-practical in addition to its cost and the patient safety requirements.

The EMT is a developmentally regulated process in which adherent epithelial cells lose their epithelial characteristics and acquire mesenchymal properties; including fibroid morphology, characteristic changes in the gene expression and increased invasion and resistance to chemotherapy Kalluri, R., *EMT: When Epithelial Cells Decide to Become Mesenchymal-like Cells*, J. Clin. Invest. 119:1417-9 (2009). In addition to eliciting the invasive phenotype, EMT also induces stem cell-like (CSC) traits that are considered to provide cancer cells the ability to self-renewal and colonization at metastatic site. Mani, S. A. et al., *The Epithelial-Mesenchymal Transition Generates Cell With Properties of Stem Cells*, Cell 133: 704-715 (2008). Thus, aberrant expression of EMT regulators in breast cancer cells may contribute to the disease progression and their identification could yield novel therapeutic targets for improved patient outcomes.

As noted herein, stable expression of TG2 in mammary epithelial cells is associated with mesenchymal transition (EMT) and this transition was associated with increased expression of transcription repressors like Snail1, Twist1, Zeb1, and Zeb2. The TG2-induced EMT is related to TGF-β signaling in that the cells transfected with TG2-shRiNA prior to TGF-β treatment failed to undergo EMT compared to the control shRNA-transfected cells, which showed morphologic and molecular alterations, typical of mesenchymal cells, in response to TGF-β treatment. Importantly, TG2-induced EMT was associated with enrichment of $CD44^{high}/CD24^{-/low}$ cell population, increased ability to form mammospheres and self-renewal ability, the traits that are considered to endorse the CSC phenotype. These observations revealed a novel function for TG2 and suggested that TG2-regulated pathways may play an important role in acquisition of drug resistance and metastasis by conferring the EMT/CSC phenotype in mammary epithelial cells.

TG2 is, therefore, a target to treat cancer diseases, due to its ability to hydrolyze guanosine triphosphate (GTP), serve as a signaling molecule and activate phospholipase C. TG2 can also be secreted outside the cell where it is related to cell-matrix regulation activities, associated with other cytosolic proteins. Cell surface TG2 can affect important cell functions such as attachment, spreading, motility, and survival. Increased TG2 expression was associated with an increased resistance to chemotherapeutic drugs, as well as, apoptosis-inducing agents.

In fact, earlier we found that overexpression of tissue transglutaminase (TG2) is associated with increased drug resistance and metastasis of cancer cells. However, the mechanisms responsible for promoting these functions were not determined. Using mammary epithelial cell (MEC) lines as a model system, here we show that TG2 expression promotes cell survival and invasive functions in MECs by inducing epithelial-mesenchymal transition (EMT). EMT characterized by differentiation of polarized epithelial cells into migratory mesenchymal-type cells and is linked with drug resistance and metastasis of cancer cells. Thus, TG2 expression supported anchorage-independent growth of MECs in soft-agar, disrupted the apical-basal polarity, and resulted in disorganized acini structures when grown in 3D-culture. At molecular level, TG2 expression resulted in loss of E-cadherin and increased expression of various transcriptional repressors of E-cadherin (Snail1, Zeb1, Zeb2 and Twist1). Moreover, TG2 expression induced stem cell-like traits in MECs as revealed by enrichment of $CD44^+/CD24^{-/low}$ cell populations. These results suggest a possible link between TG2 expression, EMT induction and the gain of epithelial stem cell properties. Overall our studies suggest that aberrant expression of TG2 is sufficient for induction of EMT in epithelial cells and thus establish a strong link between TG2 expression and progression of metastatic breast disease.

TG2 is a multifunctional protein implicated in diverse physiological and pathological processes. Lorand, L., et al., *Transglutaminases: Crosslinking Enzymes with Pleiotropic Functions*, Nat Rev Mol Cell Biol., 4:140-56 (2003). In addition to transamidation activity, TG2 can catalyze GTPase, protein disulfide isomerase and kinase activities. Akiyama, M., et al., *Expression of Transglutaminase I (Transglutaminase K) in Harlequin Ichthyosis*, Arch Dermatol Res. 289:116-19 (1997); Chandrashekar, R., et al., *An ERp60-like Protein from the Filarial Parasite Dirofilaria Immitis has both Transglutaminase and Protein Disulfide Isomerase Activity*, Proc Natl Acad Sci USA, 95:531-36 (1999); Mishra, S., et al., *Tissue Transglutaminase has Intrinsic Kinase Activity: Identification of Transglutaminase 2 as an Insulin-like Growth Factor-Binding Protein-3 Kinase*, J Biol. Chem., 279:23863-68 (2004). In normal tissues, TG2 expression is upregulated in response to tissue injury and other stressors; there it plays a role in cell/tissue defense and restoring normal homeostasis. Telei, D., et al., *Increased TG2 Expression can Result in induction of Transforming Growth Factor Beta1, Causing Increased Synthesis and Deposition of Matrix Proteins, Which can be Regulated by Nitric Oxide*, J Biol. Chem., 284:29547-58 (2009).

In such pathological conditions as tissue fibrosis and cancer, TG2 expression within the cell or its microenvironment promotes cell adhesion and modulates intracellular signaling. Fesus, L, et al., *Transglutaminase 2: an Enigmatic Enzyme with Diverse Functions*, Trends Biochem Sci. 27:534-39 (2002). For example, intracellular 1702 is known to activate focal adhesion kinase (FAK), protein kinase B, and Akt, cyclic AMP response-element binding protein, platelet-derived growth factor, and the nuclear factor-κB (NF-κB). Verna A, et al., Tissue Transglutaminase Regulates Focal Adhesion Kinase/AKT Activation by Modulating PTEN Expression in Pancreatic Cancer Cells, Clin Cancer Res., 14:1997-2005 (2008); Satpathy M, et al., *Tissue Transglutaminase Regulates Matrix Metalloproteinase-2 in Ovarian Cancer by Modulating cAMP-Response Element-Binding Protein Activity*, J Biol. Chem., 284:15390-99 (2009); Zemskov, E. A., et al., *Regulation of Platelet-Derived Growth Factor Receptor Function by Integrin-Associated Cell Surface Transglutaminase*, J Biol. Chem. 284:16693-703 (2009); Mann A P, et al., *Overexpression of Tissue Transglutaminase Leads to Constitutive Activation of Nuclear Factor-κβ in Cancer Cells: Delineation of a Novel Pathway*, Cancer Res. 66:8788-95 (2006). In the extracellular environment, TG2 can modify the extracellular matrix proteins and alter cell-cell (homotypic) and cell-matrix (heterotypic) interactions. Balklava, Z., et al., *Analysis of Tissue Transglutaminase Function in the Migration of Swiss 3T3 Fibroblasts: the Active-State Conformation of the Enzyme does not Affect Cell Motility But is Important for its Secretion*, J Biol. Chem. 277:16567-75 (2002).

As noted above, EMT is a complex dynamic process that occurs during embryonic development for reprogramming of epithelial cells. Downregulation of E-cadherin, which occurs during EMT, results in the loss of homotypic adhesion. Peinado, H., et al., *Snail, Zeb and bHLH Factors in Tumour Progression: an Alliance Against the Epithelial Phenotype?* Nat Rev Cancer, 7:415-28 (2007). Reactivation of EMT during adult life has been associated with various pathological conditions. Yang, J., et al., *Epithelial-Mesenchymal Transition: at the Crossroads of Development and Tumor Metastasis*, Dev Cell., 14:818-29 (2008). For example, EMT promotes the detachment of cancer cells from the primary tumor and facilitates migration through the acquisition of stern cell like properties, including loss of cellular polarity and adhesion. Thiery, J. P., et al., *Epithelial-Mesenchymal Transitions in Development and Disease*, Cell, 39:871-90 (2009).

Moreover, emerging evidence suggests a link between EMT and chemoresistance and radioresistance. Thiery, J. P., et al., *Epithelial-Mesenchymal Transitions in Development and Disease*, Cell. 39:871-90 (2009); Wang, Z., et al., *Acquisition of Epithelial-Mesenchymal Transition Phenotype of Gemcitabine-Resistant Pancreatic Cancer Cells is Linked with Activation of the Notch Signaling Pathway*, Cancer Res. 69:2400-7 (2009). Here, we demonstrate that overexpression of TG2 in mammary epithelial cells (MECs) is associated with loss of E-cadherin, cellular polarity, upregulation of mesenchymal molecular markers, such as fibronectin, vimentin, N-cadherin and transcriptional repressors of E-cadherin, such as Snail1, Zeb1, Zeb2 and Twist1. Furthermore, our data suggest that TG2 is a downstream mediator of tumor growth factor-beta (TGF-β)-induced EMT.

Example 1

TG2 Induces EMT in Mammary Epithelial Cells and Promotes Stem Cell-Like Phenotype Materials and Methods The immortalized human mammary epithelial cells (MCF10A and MCF12A) were maintained as previously described. Debnath, J., et al., *Morphogenesis and Oncogenesis of MCF-10A Mammary Epithelial Acini Grown in Three-Dimensional Basement Membrane Cultures*, Methods, 30:256-68 (2003). TG2 gene was subcloned into pCDH lentiviral vector (System Biosciences, Frederick, Md.) from pcDNA3.1-TG2 vector, kindly provided by Dr. Gail Johnson, University of Rochester, N.Y. Control ShRNA and TG2 shRINA letiviral particles were purchased from Santa Cruz Biotechnology (Santa Cruz, Calif.). MCF10A-vec and MCF10A-TG2 cells were made by retroviral infection. Retroviral infection of cells and their 3D culture were done as previously described. Debnath, J., et al., *Morphogenesis and Oncogenesis of MCF-10A Mammary Epithelial Acini Grown in Three-Dimensional Basement Membrane Cultures*, Methods, 30:256-68 (2003). Stable clones were selected against. 800 ng/ml puromycin and karyotyped to confirm their authenticity by comparing the marker chromosome with the parental cell lines (kindly performed by Dr. Sen Pathak of this institute). Multiple stable clones were used to rule out potential clonal effects. All experiments were performed between passage 5 and 25. Lentivirus production and infection, and reagents used, are described in the Supplemental Experimental Procedures. For TGF-β treatment, the MCF10A-cont-ShRNA and MCF10A-TC12 shRNA cells were cultured in MCF10A medium and treated with 2.5 ng/ml of recombinant-TGF-1 (kindly provided by Dr. Bharat Aggarwal, M. D. Anderson Cancer Center) for 12 days.

Antibodies, Western Blotting, and Immunofluorescence.

For Western blots, cells were lysed on ice in 50 mM Tris-HCl buffer, pH 7.5 containing 150 mM NaCl and 0.5% NP-40. Fifty micrograms of total protein from each sample were resolved on a 4%-12% SDS Bis-Tris-polyacrylamide gel with running buffer and transferred onto nitrocellulose membranes. The blots were then probed with various antibodies (details are given in Supplemental Experimental Procedures). Immunofluorescence staining of monolayer cell cultures and 3D culture was done as previously described. Debnath, J., et al., *Morphogenesis and Oncogenesis of MCF10A Mammary Epithelial Acini Grown in Three-Dimensional Basement Membrane Cultures*, Methods, 30:256-68 (2003).

RNA Extraction, RT-PCR, and Quantitative RT-PCR.

The detailed procedures for RNA extraction RT-PCR and primers sequences are described in the Supplemental Experimental Procedures. Quantitative RT-PCR for EMT-associated genes was done using SABiosciences (Frederick, Md.) EMT-PCR Array according to the manufacturer's protocol.

Invasion, Soft Agar Colony Formation, and NF-κB activity.

Invasion assay and NF-κB activity assay were performed as described previously. Mann A P, et al., *Overexpression of Tissue Transglutaminase Leads to Constitutive Activation of Nuclear Factor-κβ in Cancer Cells: Delineation of a Novel Pathway*, Cancer Res. 66:8788-95 (2006). Soft agar assays were performed as described previously. Cifone, M. A., et al., *Correlation of Patterns of Anchorage-Independent Growth within in vivo Behavior of Cells from a Murine Fibrosarcoma*, Proc Natl Acad Sci USA, 77:1039-43 (1980). Cultures were photographed, and the colonies with diameters larger than 500 mm were counted using Image J software (previously NIH image).

FACS Analysis.

The anti-CD44 (clone G44-26), anti-CD24 (clone ML5), and anti-CD45 (clone 2D1) antibodies used for FACS analysis were obtained from BD Biosciences (San Jose, Calif.). The anti-CD326 (clone HEA-125) was obtained from Miltenyi Biotec (Auburn, Calif.). Briefly, for each cell line, $5 \times 10^5$ cells were aliquoted into 2 tubes; tube 1 was stained with IgG isotype controls for FITC, PE, PereP, and APC; tube 2 was stained with anti-CD44-FITC, anti-CD24-PE, anti-GD45-PerCP, and anti-CD326-APC. Cells were incubated with appropriate antibodies at room temperature in dark for 30 minutes, and then washed with PBS. Cells were acquired by 4-color FACSCalibur (BD Biosciences), each sample was acquired 10,000 cells for analysis.

Results

TG2 Induces EMT in Mammary Epithelial Cells.

Figure 1A:
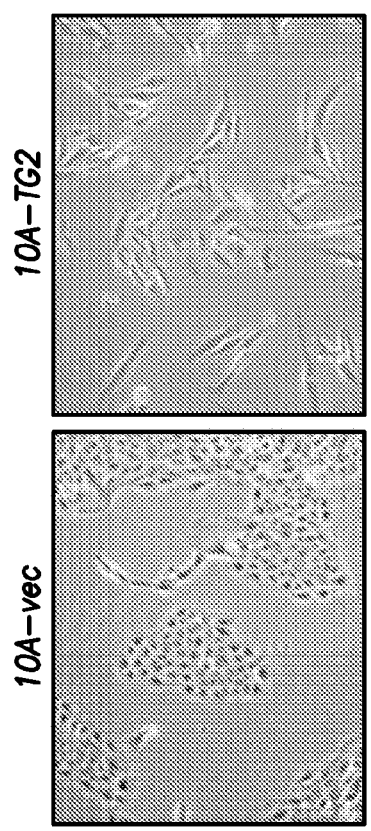
Figure 1D:
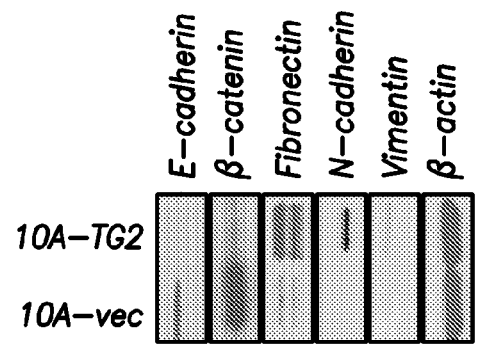
Figure 1C:
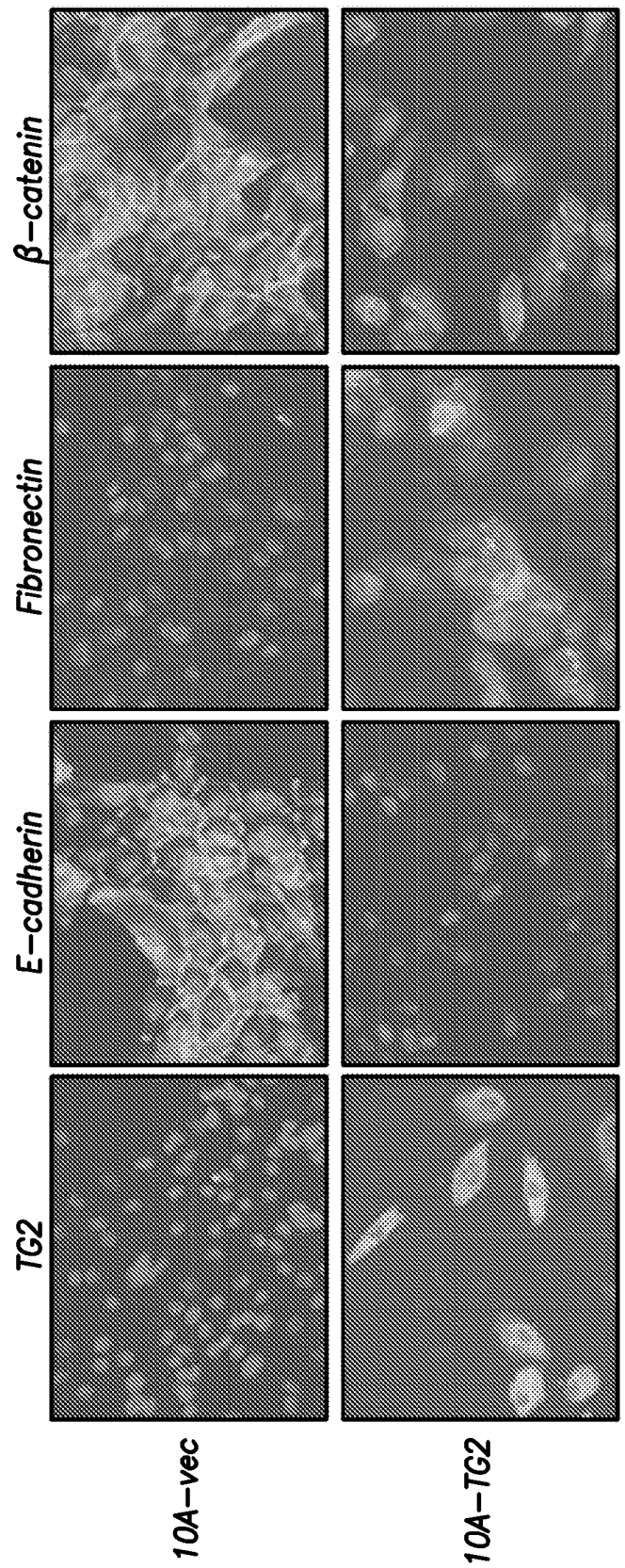

We previously reported that metastatic breast cancer cells express high basal levels of TG2 and that increased expression of TG2 in breast cancer cells contributes to their increased survival, invasion, and motility. Mehta, K., et al., *Prognostic Significance of Tissue Transglutaminase in Drug Resistant and Metastatic Breast Cancer*, Clin Cancer Res., 10:8068-76 (2004); Mangala, L. S., et al., *Tissue Transglutaminase Expression Promotes Cell Attachment, Invasion and Survival in Breast Cancer Cells*, Oncogene, 26:2459-70, (2007). To understand better the role of TG2 in metastatic transformation, we stably transfected TG2 into cells of the non-transformed human breast mammary epithelial line MCF10A. TG2-overexpressing MCF-10A cells (MCF10A-TG2) showed marked changes in their morphology compared to the vector-transfected (MCF10A.Vec) cells. As shown in FIG. 1A, MCF10A.vec cells appeared rounded with cobblestone epithelial morphology and grew as tightly connected clusters. MCF10A-TG2 cells, in contrast, displayed spindle-like shape and exhibited scattered distribution of fibroblast-like, mesenchymal appearing cells with loose cell-to-cell adhesion (FIG. 1A). Expression of 162 in these cells was confirmed by immunoblotting (FIG. 1B) and immunostaining (FIG. 1C). The mesenchymal nature of the cells was further confirmed by evidence of accumulation of stress fiber in the MCF10A-TG2 cells (FIG. 19). These results suggested that TG2 expression in epithelial cells is associated with their transition into mesenchymal cells.

The morphological changes during EMT are driven by a number of molecular alterations, including loss or decrease of epithelial cell markers (e.g., E-cadherin and □-catenin) and de novo expression of mesenchymal markers (e.g., N-cadherin, vimentin, and fibronectin). Thiery, J. P., et al., *Epithelial-Mesenchymal Transitions in Development and Disease*, Cell. 39:871-90 (2009). Indeed, MCF10A.vec cells expressed high levels of E-cadherin and β-catenin but low or undetectable levels of fibronectin, vimentin and N-cadherin. MCF10A-TG2 cells, in contrast, showed almost complete loss of E-cadherin and reduced levels of □-catenin (FIGS. 1C and D). Similarly, the expression of N-cadherin, fibronectin, and vimentin was upregulated in MCF-10A-162 cells (FIG. 1D). MCF10A-vec cells showed membranous staining of E-cadherin and β-catenin but no staining for fibronectin (FIG. 1C). In contrast, MCF10A-TG2 cells showed loss of E-cadherin staining, reduced cytoplasmic β-catenin and increased fibronectin staining (FIG. 1C). These TG2-induced alterations were not unique to the MCF10A cells, as similar changes in the morphology, E-cadherin, and Fibronectin expression became evident in another human mammary epithelial cell line (MCF-12A) in response to TG2 expression (FIG. 20). These observations clearly imply that TG2 expression resulted in loss of cell-cell adhesion by inducing EMT in mammary epithelial cells.

TG2 Expression Results in Altered Expression of Snail1, Twist1 and Zeb1.

Figure 2A:
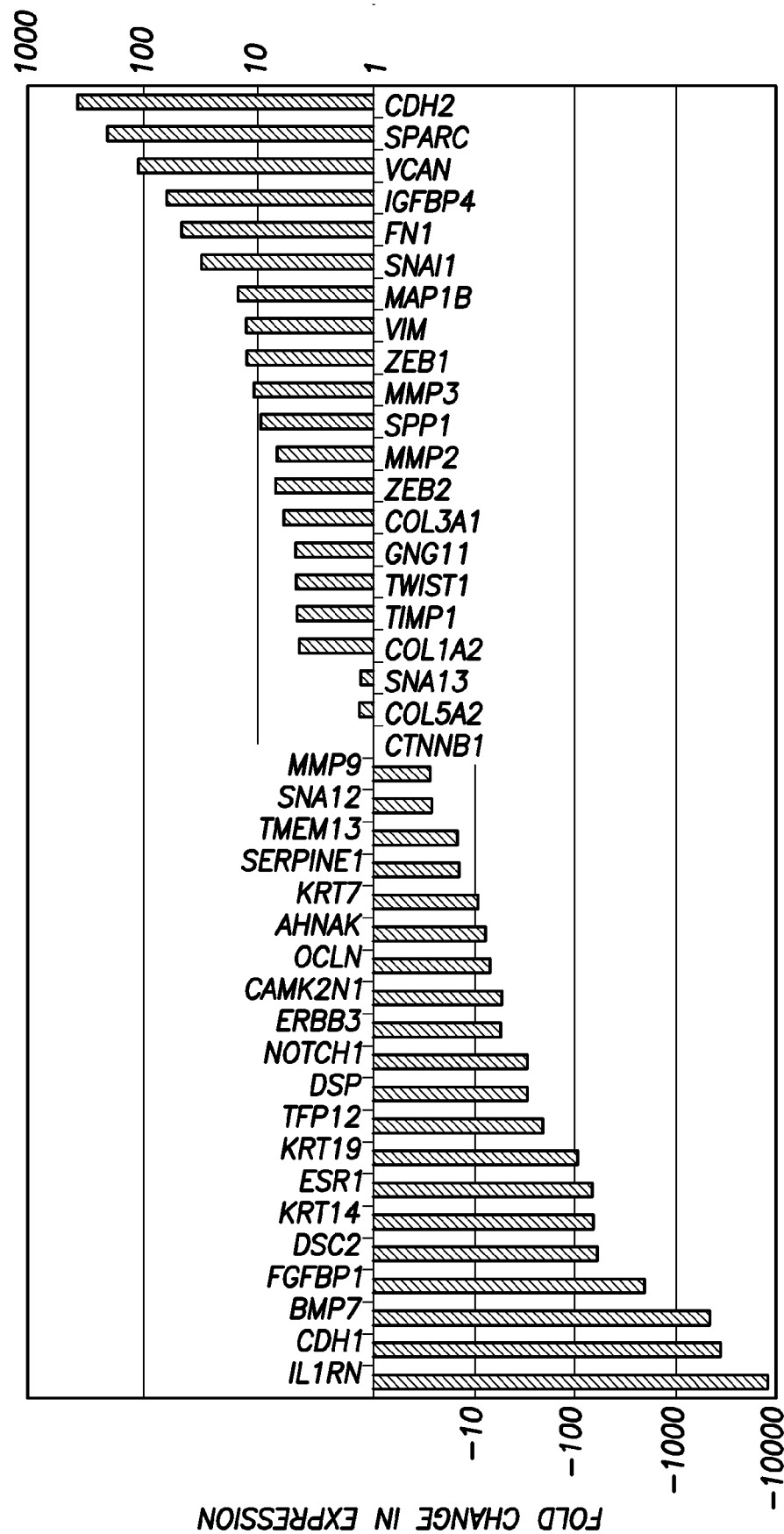
FIGS. 2A, 2B and 2C show TG2 induces upregulation of Snail1, Twist1, Zeb1 and Zeb2 and confers EMT phenotype.
Figure 2D:
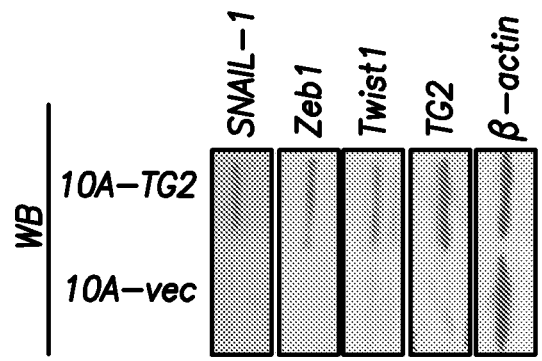
Figure 2C:
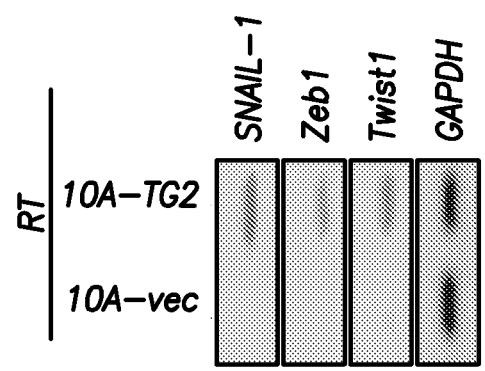
Figure 2B:
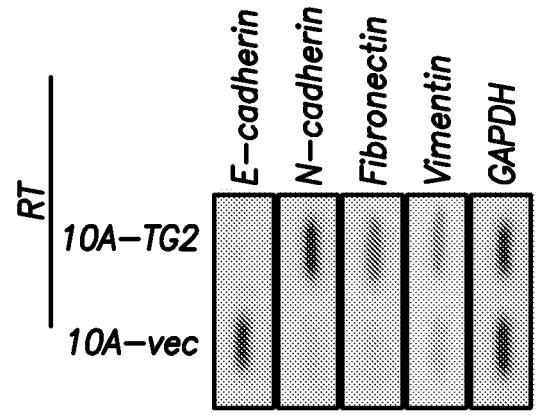

Induction of EMT is orchestrated by various transcription factors including Snail1, Slug, Twist, Zeb1, Zeb2, E12, E47. Kalluri, R., *EMT: When Epithelial Cells Decide to Become Mesenchymal-Like Cells*, J Clin invest., 119:1417-19 (2009). To which of these transcription factors are involved in TG2-induced EMT, we performed transcriptional profiling of EMT-associated genes using the SABiosciences' real-time PCR-based EMT array. FIG. 2A shows the relative expression of EMT-associated genes in MCF10A-TG2 cells with respect to MCF10A-vec cells. The epithelial markers E-cadherin (CDH1), desmocollin 2, Krt 19, Krt14, Krt7, desmoplakin and occludin were down-regulated, the mesenchymal markers N-cadherin, versican, fibronectin, Sparc, and vimentin were upregulated. These results suggest that loss of E-cadherin and upregulation of N-cadherin (CDH2), fibronectin and vimentin in MCF10A-TG2 cells was regulated at the transcriptional level. To validate these results, we performed RT-PCR for E-cadherin, N-cadherin, fibronectin and vimentin in MCF10A-vec and MCF10A-TG2 cells. The results shown in FIG. 2B further supported our conclusions that 162 expression was associated with a complete loss of E-cadherin transcript and an increase in N-cadherin, fibronectin, and vimentin transcripts. Accordingly, MCF10A-TG2 cells showed a significant increase in the transcript levels of snail1, zeb1, zeb2, and twist1 (FIG. 2A), the known transcriptional repressors of E-cadherin and inducers of N-cadherin, fibronectin, and vimentin. Similar results were obtained for snail1, zeb1 and twist1 expression by RT-PCR and western blot at bath the transcriptional (FIG. 2C, left panel) and protein levels (FIG. 2C, right panel). These results suggest that TG2 expression induced transcriptional repression of E-cadherin and transactivation of fibronectin, N-cadherin, and vimentin by altering Snail1, Zeb1, Zeb2, and Twist1 levels.

TG2-Induced EMT Confers Invasive and Tumorigenic Phenotype.

Based on the biological contexts, EMT has been classified into three subtypes: Type 1 is associated with implantation, embryo formation, and organ development and is important to generate diverse cell types that share common mesenchymal phenotypes. Type 1 EMT neither causes fibrosis nor induces invasive phenotype. Type 2 EMT is associated with wound healing, tissue regeneration, and organ fibrosis and likewise does not induce the invasive phenotype. Type 3 EMT is associated with cancer and is marked by more invasive and metastatic cells. Kalluri R, et al. The Basics of Epithelial-Mesenchymal Transition, J Clin Invest., 119:1420-28 (2009). In our experiments, TG2 expression increased the invasive ability of MCF10A-TG2 cells compared to the MCF10A-vec cells (FIG. 3A). These results suggested that 102 induced Type 3 EMT and is associated with the acquisition of invasive and metastatic potential. As a result, we next determined whether 102-induced EMT would promote the oncogenic phenotype in MCF10A cells. We measured the growth of MCF10A-vec and MCF10A-TG2 cells in soft agar an in vitro surrogate measure of tumorigenicity. Cifone, M. A., et al., *Correlation of Patterns of Anchorage-Independent Growth within vivo Behavior of Cells from a Murine Fibrosarcoma*, Proc Natl Acad Sci USA, 77:1039-43 (1980). Results shown in FIG. 3B demonstrate that while MCF10A-TG2 cells could grow and form colonies in soft agar, MCF10A-vec cells failed to survive.

Figure 3C:
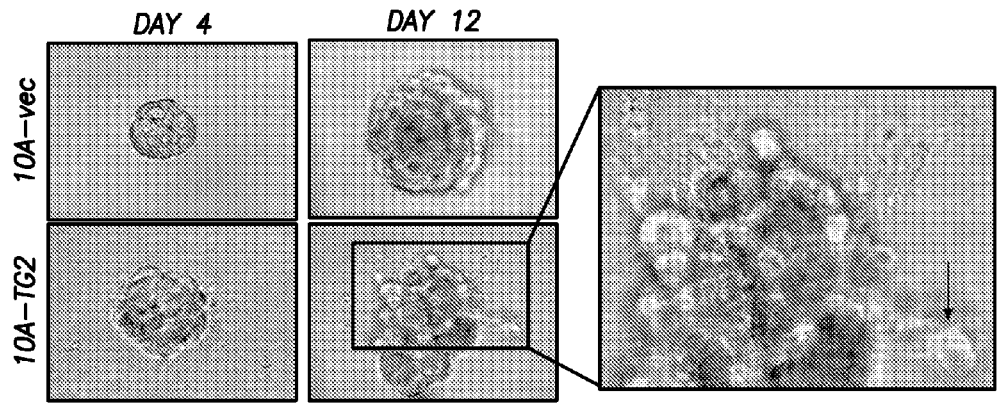
Figure 3D:
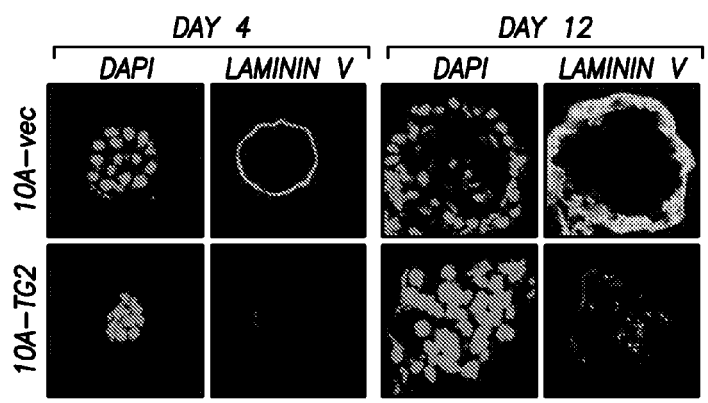
Figure 22:
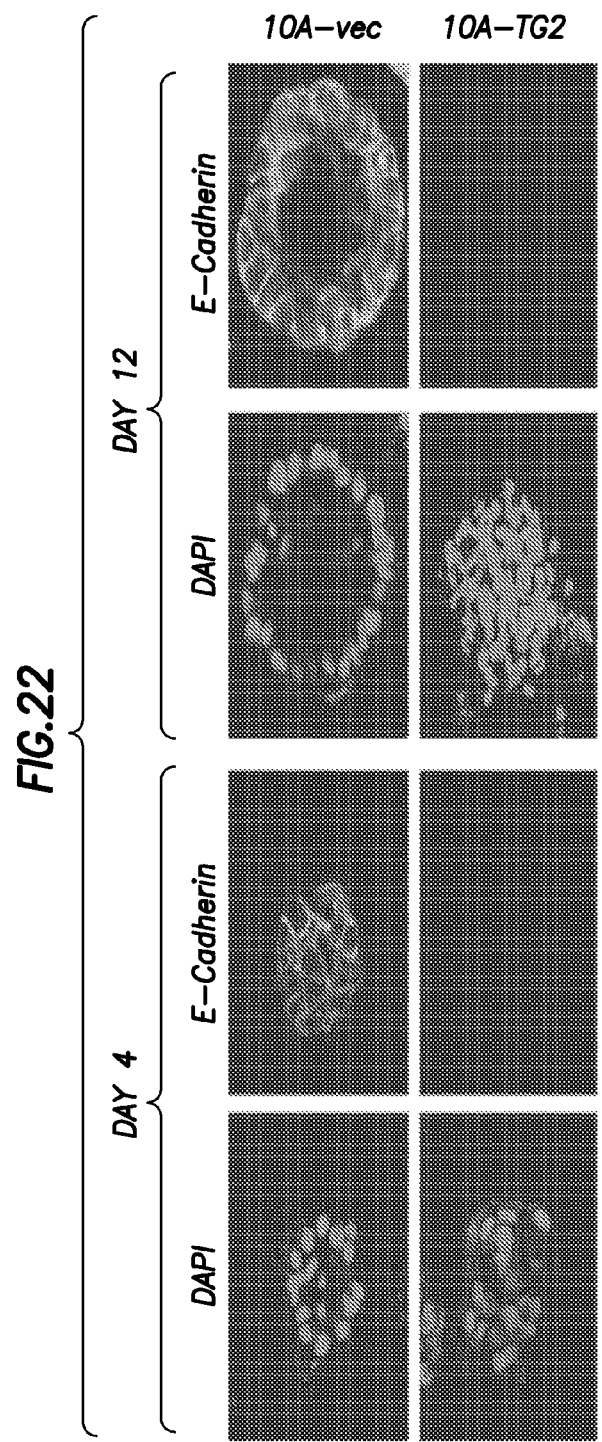
FIG. 22 shows immunostaining for E-cadherin revealed loss of E-cadherin expression/
Figure 23:
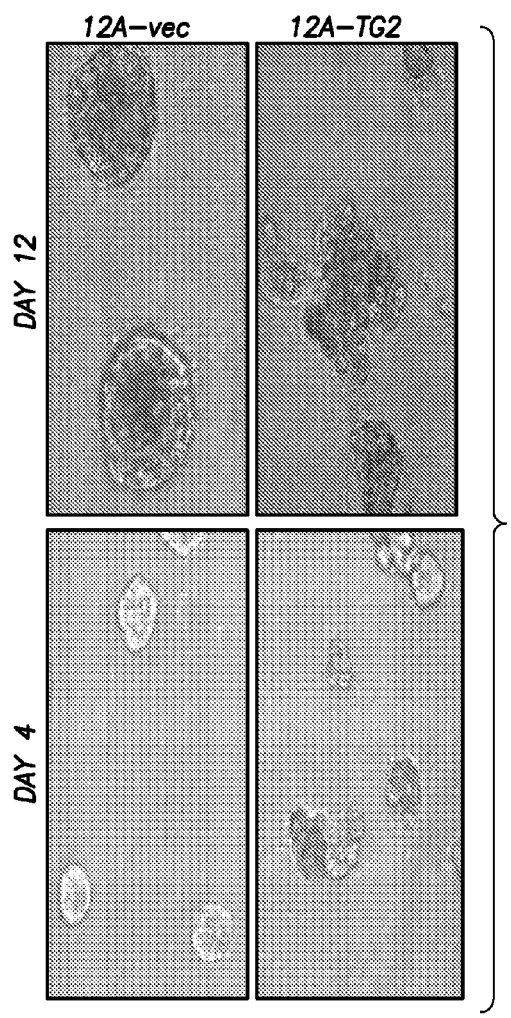
FIG. 23 shows changes similar to MCF-10A cells in the growth pattern and acinar structures of TG2-expressing MCF-12A cells are evident when grown in 3D culture.

MCF10A is a non-transformed human mammary epithelial cell line and is an excellent in vitro model to study mammary gland development and breast cancer progression in 3D cultures. These cells form well-organized acinar structures that mimic the normal mammary end bud in vivo, Debnath, J., et al., *Morphogenesis and Oncogenesis of MCF-10A Mammary Epithelial Acini Grown in Three-Dimensional Basement Membrane Cultures*, Methods, 30:256-68 (2003). We used this 3D model to determine whether TG2-induced EMT can disrupt the organization of MCF10A cells. As shown in FIG. 3, the MCF10A-vec cells grew into well-organized acinar-like structures with hollow lumens (FIGS. 3C and D, top panel). Immunostaining of spheroids with anti-laminin V antibody revealed the presence of continuous well-defined basement membrane surrounding the acini and apicobasal polarization of cells (FIG. 3D). Similarly, immunostaining of spheroids for E-cadherin suggested apico-basal polarization with cell-to-cell contact in acinar structures (FIG. 22). MCF10A-TG2 cells, in contrast, demonstrated severe disruption of acinar architecture, characterized by increased spheroid size and no lumen formation (FIGS. 3C and 3D, lower panels). A distinct feature of MCF10A-TG2 acini was the gain of invasive function; many cells escaped from the acini and invaded the surrounding matrix (FIG. 3C, inset). Similarly, immunostaining for laminin V and E-cadherin revealed diffuse basement membrane formation (FIG. 3D) and loss of E-cadherin expression (FIG. 22) in MCF10-TG2 acini. Similar changes in the growth pattern and acinar structures of TG2-expressing MCF-121 cells became evident when grown in 3D culture (FIG. 23). Overall these results suggest that TG2-induced EMT facilitated transformation of mammary epithelial cells into invasive and tumor-like phenotype.

TG2-Induces Non-Canonical TGF-β Signaling to Regulate E-Cadherin Repression.

Figure 24:
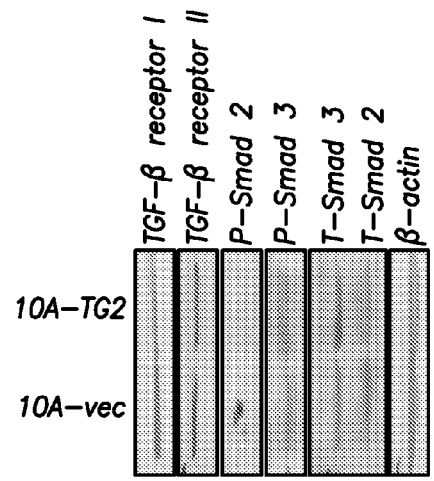
FIG. 24 shows that no changes were observed either in receptor levels or phosphorylation status of smad 2 or smad 3.

Because the EMT gene signature of MCF10A-TG2 cells (FIG. 2A) looked very similar to TGF-β-induced EMT, we next determined whether TG2-induced EMT involved TGF-β signaling pathways. Xu, J., et al., *TGF-β-Induced Epithelial to Mesenchymal Transition*, Cell Res., 19:156-72 (2009). For this purpose, we checked the expression of TGF-β receptor-1 and -2 and phospho-smad 2 and 3 in MCF10A-vec and MCF10A-TG2 cells. Interestingly, we did not observe any change either in receptor levels or phosphorylation status of smad 2 or smad 3 (FIG. 24), suggesting that TG2-induced EMT occurred independent of TGF-β signaling. The progression of the EMT program is regulated by a series of intracellular signaling molecules, such as NF-κB, MAPK, PI3K, Akt, RhoB, Ras, and c-Fos as well as by cell-surface proteins, such as β4 integrin, α5β1 integrin, and αVβ6 integrin. Tse, J. C., et al., *Mechanisms of Metastasis: Epithelial-To-Mesenchymal Transition and Contribution of Tumor Microenvironment*, J Cell Biochem, 101:816-29 (2007). Previous studies have shown that 162 expression results in constitutive activation of NF-κB. Mann A P, et al., *Overexpression of Tissue Transglutaminase Leads to Constitutive Activation of Nuclear Factor-κβ in Cancer Cells: Delineation of a Novel Pathway*, Cancer Res. 66:8788-95 (2006); Kim, D. S., et al., *Reversal of Drug Resistance in Breast Cancer Cells by Transglutaminase 2 Inhibition and Nuclear Factor-κβ Inactivation*, Cancer Res. 66:10936-43 (2006). Therefore, we next determined the status of NR-κB in MCF10A-vec and MCF10A-TG2 cells. Results shown in FIG. 4A show almost a 4-fold increase in NF-κB activity of MCF10A-TG2 cells compared with the MCF10A-vec cells. These results suggest that TG2-mediated activation of NF-κB may be responsible for transcriptional regulation of Snail1 and induction of EMT in MCF10A-TG2 cells. Indeed, TG2 was recently shown to associate with NF-κB for its recruitment to the promoter sequence of Snail and leading to its transcriptional regulation. Kim, Y., et al., *Transglutaminase II Interacts With rac1, Regulates Production of Reactive Oxygen Species, Expression of Snail, Secretion of TH2 Cytokines and Mediates in vitro and in vivo Allergic inflammation*, Mol. Immunol., 47:1010-22 (2010).

We also checked the status of pFAK and pAkt, the other known mediators of EMT, in MCF10A-TG2 cells. Sabbah, M., et al., *Molecular Signature and Therapeutic Perspective of the Epithelial-to-Mesenchymal Transitions in Epithelial Cancers*, Drug Resist Updat., 11:123-51 (2008). Results shown in FIG. 4B revealed constitutive activation of both the FAK and Akt in MCF10A-TG2 cells. These observations suggest that TG2-mediated activation of FAK, Akt and NF-κB may play a role in driving MCF10A cells into EMT by regulating snail, zeb1, and twist expression. Because TGF-β can induce TG2 expression, we next determined whether TG2 expression is required for TGF-β induce EMT. Jung, S. A., et al., *Upregulation of TGF-β-Induced Tissue Transglutaminase Expression by PI3K-Akt Pathway Activation in Human Subconjunctival Fibroblasts*, Invest Ophthalmol Vis Sci., 48:1952-58 (2007). MCF10A cells stably transfected with TG2-shRNA and treated with TGF-β for 12 days resembled untreated cells and showed minimal change in their morphology (FIG. 4C). In contrast, identically treated MCF10A-control shRNA-transfected cells underwent dramatic changes in the morphology. They appeared elongated and had a mesenchymal-like appearance (FIG. 4C). Western blot analysis for epithelial markers showed loss of E-cadherin in TGF-β treated MCF10A-control-shRNA but not in TG2shRNA-transfected cells, whereas fibronectin expression was increased in both cell types (FIG. 4D). These results clearly suggest that TG2 is a downstream mediator of TGF-β-induced EMT.

TG2-Induced EMT Promotes Stem Cell-Like Phenotype.

Figure 5A:
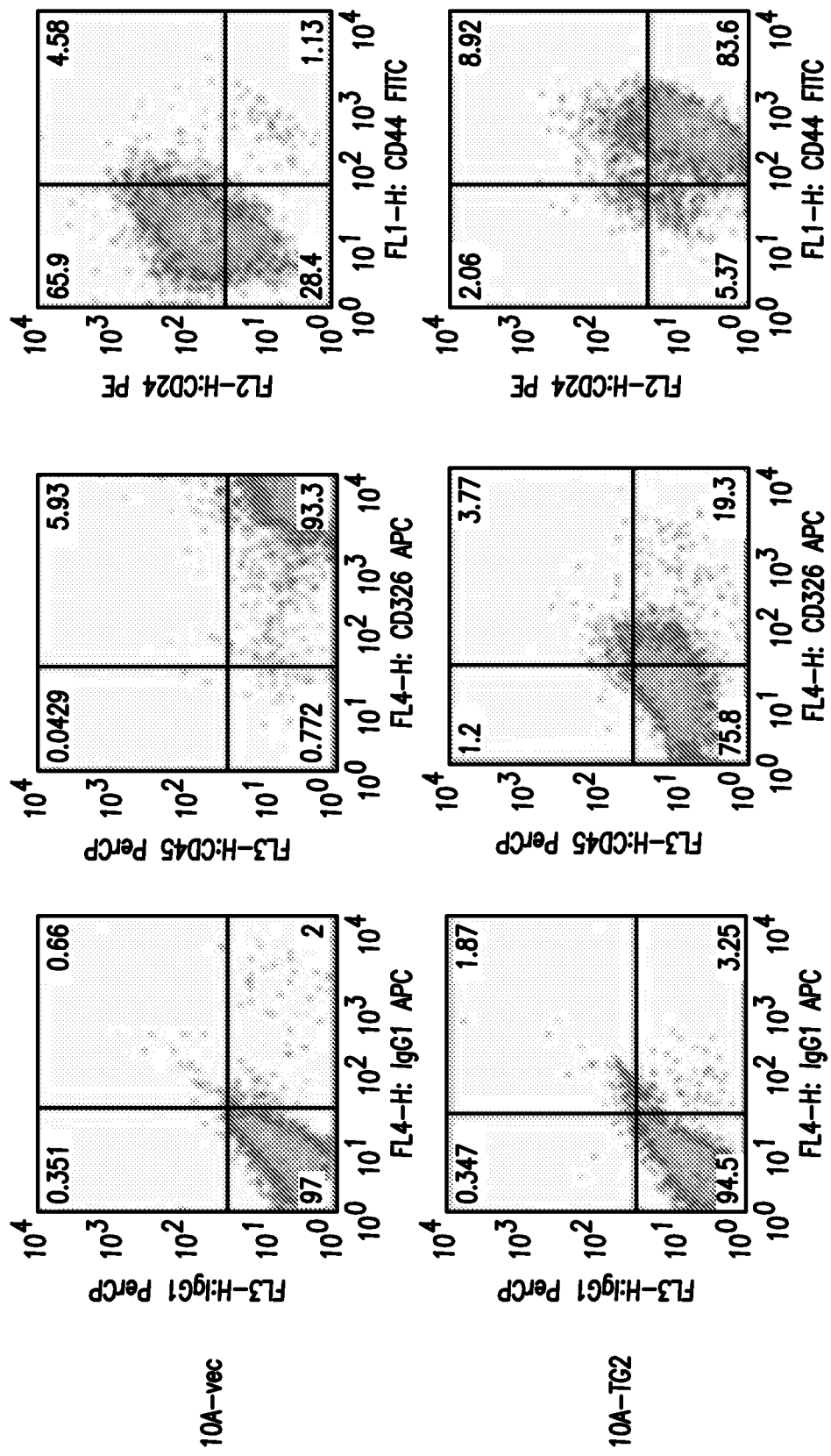
FIGS. 5A and 5B show TG2 expression induces stem cell characteristics. FACS analysis of cell surface markers CD326, CD45, CD44 and CD24 in MCF10A (A) and MCF-7 (B) breast epithelial cells, expressing exogenous (10A-TG2) or endogenous (MCF-7/RT) TG2. 10A-vec and MCF-7 cells, which lack TG2 expression, served as controls.
Figure 5B:
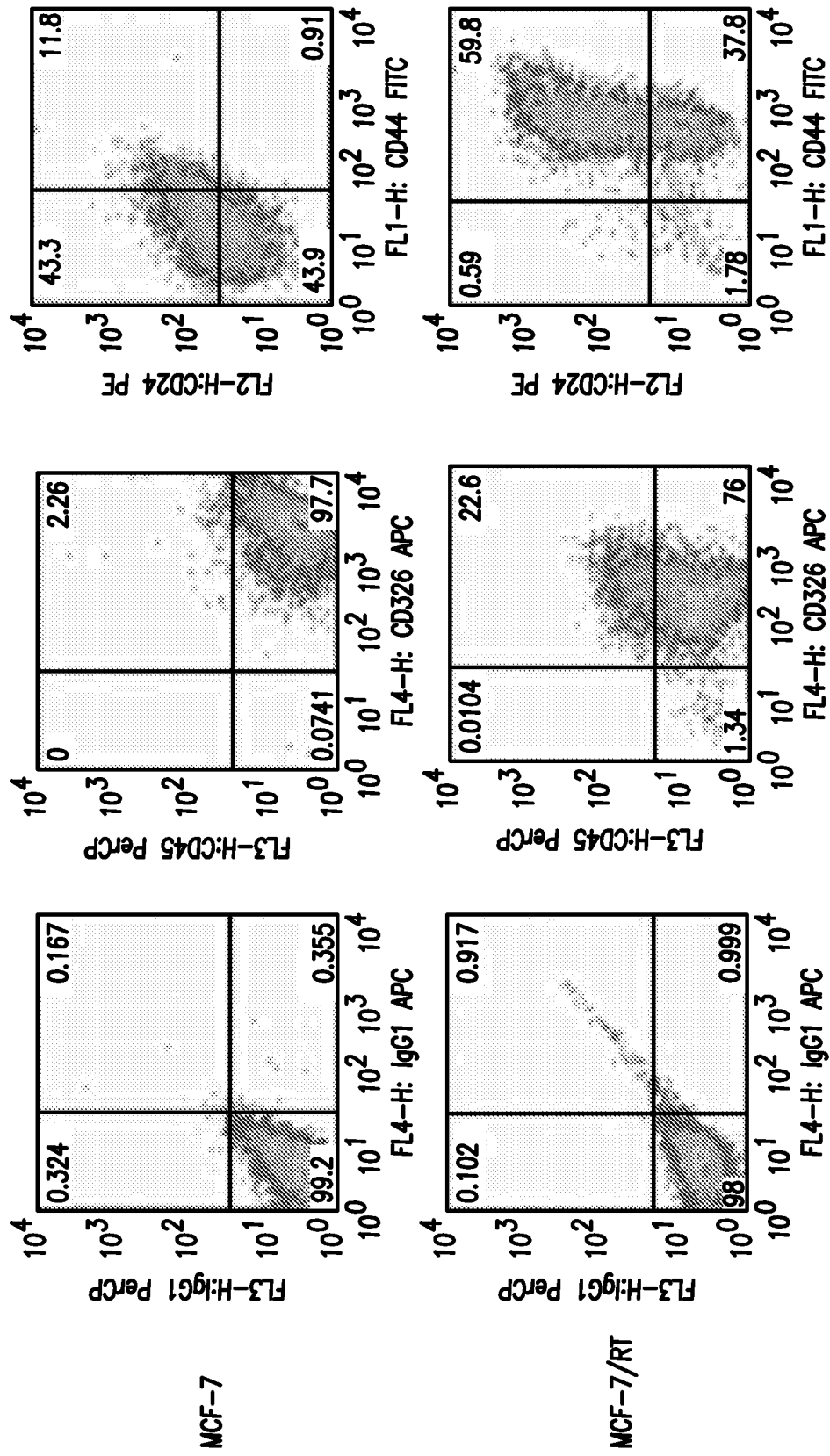
Figure 25:
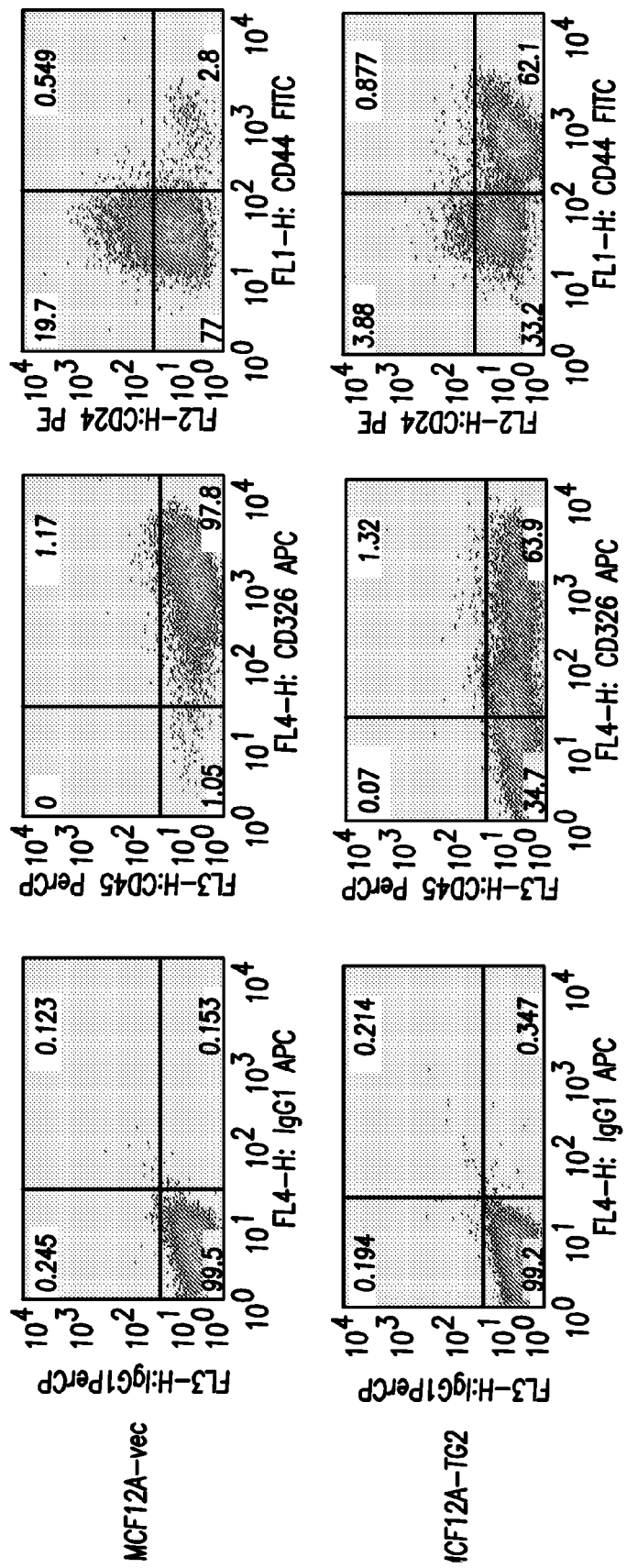
FIG. 25 shows TG2-transfected MCF12A cells having similar enrichment in $CD44^{high}/CD24^{-/low}$ expressing cells compared to the control vector-infected cells.

Based on recent reports that induction of EMT results in acquisition of stem cell-like characteristics and that EMT and stem cells have a common molecular link in breast epithelial cells, we determined whether TG2-induced EMT could induce a stem cell state in MCF10A cells. Mani, S. A., et al., *The Epithelial-Mesenchymal Transition Generates Cells with Properties of Stem Cells*, Cell. 133:704-15 (2008). We used flow cytometric analysis to determine the expression of $CD44^{high}/CD24^{-/low}$ phenotype in MCF10A-TG2 and MCF10A-vec cells. The $CD44^{high}/CD24^{-/low}$ has been used as a marker to isolate stem cells from normal and cancerous mammary epithelial cells. Liao, M. J., et al., *Enrichment of a Population of Mammary Gland Cells That Form Mammospheres and have in vivo Repopulating Activity*, Cancer Res. 67:8131-38 (2007). Results from a representative experiment shown in FIG. 5A revealed significantly more MCF10A-TG2 cells expressed $CD44^{high}/CD24^{-/low}$ stem cell markers. Consistent with this result the expression of CD326 antigen, an epithelial marker, was significantly downregulated in MCF10A-TG2 cells. To further validate these results, we next analyzed the $CD44^{high}/CD24^{-/low}$ expression in the doxorubicin-resistant MCF-7/RT breast cancer cell line. Herman. J. F., et al., *Implications of Increased Tissue Transglutaminase (TG2) Expression in Drug-Resistant Breast Cancer (MCF-7) Cells*, Oncogene, 25:3049-58 (2006). The constitutive expression of TG2 in MCF-7/RT cells was associated with a similar enrichment of $CD44^{high}/C24^{-/low}$ cell population compared to the parental drug-sensitive and TG2-deficient MCF-7 cells (FIG. 5B). Moreover, TG2-transfected MCF-12A cells showed similar enrichment in $CD44^{high}/CD24^{-/low}$ expressing cells compared to the control vector-infected cells (FIG. 25). These results suggest that aberrant expression of TG2 in epithelial cells was associated with induction of EMT and acquisition of stem cell phenotype.

Our results indicate that aberrant expression of 162 serves as an oncogenic signal in mammary epithelial cells and promotes EMT and stem cell-like phenotype. Thus, over expression of TG2 in mammary epithelial cells was associated with increased invasiveness, loss of cell polarity, increased cell survival, and anchorage-independent growth. EMT marks the conversion of polarized and immotile epithelial cells to highly motile cells during embryogenesis and wound healing. It is characterized by the loss of cell-cell adhesion, apical basal cell polarity, and increased cell motility. In tumors, the EMT is considered to play an important role during tumor progression and development of metastasis. Thiery, J. P., et al., *Epithelial-Mesenchymal Transitions in Development and Disease*. Cell. 39:871-90 (2009); Tse, J. C., et al. *Mechanisms of Metastasis: Epithelial-To-Mesenchymal Transition and Contribution of Tumor Microenvironment*, J Cell Biochem, 101:816-29 (2007).

Several lines of evidence suggest that, depending on the cellular context, TG2 can either promote or suppress tumor growth. Kotsakis. P., et al., *Tissue Transglutaminase in Tumour Progression: Friend or Foe?* Amino Acids., 33:373-84 (2007). Anti-tumorigenic properties of TG2 are mainly linked to its ability to irreversibly crosslink proteins and drive cells into apoptosis. Under physiological conditions the intracellular TG2, however, remains catalytically inactive due to high $GTP/Ca^{2+}$ ratio and serves as a pro-survival factor. Several recent reports have documented that drug-resistant and metastatic breast cancer cells express high basal levels of TG2 and that increased expression of TG2 contributes to their survival, invasiveness, and drug resistance. Mehta, K., et al., *Prognostic Significance of Tissue Transglutaminase in Drug Resistant and Metastatic Breast Cancer*, Clin Cancer Res., 10:8068-76 (2004); Mangala, L. S., et al., *Tissue Transglutaminase Expression Promotes Cell Attachment, Invasion and Survival in Breast Cancer Cells*, Oncogene, 26:2459-70, (2007); Kim, D. S., et al., *Reversal of Drug Resistance In Breast Cancer Cells by Transglutaminase 2 Inhibition and Nuclear Factor-κβ Inactivation*, Cancer Res. 66:10936-43 (2006); Antonyak, M. A., et al., *Augmentation of Tissue Transglutaminase Expression and Activation by Epidermal Growth Factor Inhibit Doxorubicin-Induced Apoptosis in Human Breast Cancer Cells*, J Biol Chem., 279:41461-67 (2004); Park, K. S., et al., *Increase in Transglutaminase 2 Expression is Associated with NF-κβ Activation in Breast Cancer Tissues*, Front Biosci., 14:1945-51 (2009). However, the TG2-regulated pathways that contribute to increased cell survival and metastatic functions have remained largely unknown.

Successful metastasis of a primary tumor involves invasion, intravasation, survival in circulation, extravasation, and colonization at distant sites. Many cancer cell types leaving the primary tumor rely on EMT program to facilitate successful execution of these steps. Thiery, J. P., et al., *Epithelial-Mesenchymal Transitions in Development and Disease*, Cell. 39:871-90 (2009). This fact indicates that successful formation of macroscopic metastasis should be an exceedingly rare event. In this connection, a link between metastasis and stem cell state has been proposed to explain the ability of tumor cells to form macroscopic metastases. For example, Mani et al, recently proposed that the EMT program could enable cancer cells to disseminate from the primary tumor and promote their self-renewal ability by inducing a stem cell state.

Mani, S. A., et al., *The Epithelial-Mesenchymal Transition Generates Cells with Properties of Stem Cells*, Cell. 133:704-15 (2008). In view of these observations and our current data, it is reasonable to conclude that induction of EMT is an important mechanism by which TG2 transforms epithelial cells into a metastatic state.

Evidence is accumulating to indicate that the EMT confers many malignant traits in epithelial cells. In order for carcinoma cells to break away from neighboring cells and to invade the adjacent cell layers, they must lose cell-cell adhesion and acquire motility. Indeed, TG2 expression induced the loss or downregulation of various epithelial markers like E-cadherin, desmocollin, desmoplakin and occludin (involved in formation of tight cell-cell junctions), thus permitting mammary epithelial cells to lose cell-cell contact. Similarly, EMT can also modulate other adhesion molecules and trigger remodeling of the actin cytoskeleton, leading to mesenchymal phenotype and increasing the scattering and motility of carcinoma cells. Thiery, J. P., *Epithelial-Mesenchymal Transitions in Tumour Progression*, Nat Rev Cancer, 2:442-54 (2002).

Acquisition of the mesenchymal phenotype has been associated with invasive cell behavior. Accordingly, TG2 expression in MCF10A cells increased their invasive potential, disrupted their organized growth in 3D culture, and conferred invasive phenotype. Our results are consistent with those of a report on metastatic ovarian cancer cells suggesting that TG2 expression is associated with induction of the EMT. Shao, M., et al, *Epithelial-to-Mesenchymal Transition and Ovarian Tumor Progression Induced by Tissue Transglutaminase*, Cancer Res. 69:9192-201 (2009). Once detached from the original niche, transformed epithelial cells must acquire autonomy from growth factors and confer survival advantage. For example, normal epithelial cells when detached from the neighboring cells die due to anoikis. However, when these cells undergo EMT they are protected from anoikis and grow in anchorage-independent manner just like their transformed counterparts. Mani, S. A., et al., *The Epithelial-Mesenchymal Transition Generates Cells with Properties of Stem Cells*, Cell. 133:704-15 (2008). Indeed, an earlier report suggests that TG2 expression could rescue normal fibroblasts from anoikis. Verderio, E. A., et al., *A Novel RGD-Independent Cell Adhesion Pathway Mediated by Fibronectin-Bound Tissue Transglutaminase Rescues Cells from Anoikis*, J Biol. Chem., 278:42604-14 (2003). This ability of TG2 may be responsible for promoting autonomy of mammary epithelial cells from growth regulatory mechanisms and supporting anchorage-independent growth.

After successful extravasation, the transformed cells must colonize in the hostile environments of foreign tissue. This process involves the growth of micrometastases into macroscopic metastases. Recently, it has been proposed that EMT can enable cancer cells not only to disseminate but also acquire the ability of self-renewal by inducing a stem cell state in the cancer cells. Kalluri, R., *EMT: When Epithelial Cells Decide to Become Mesenchymal-Like Cells*, J Clin Invest, 119:1417-19 (2009); Mani, S. A., et al., *The Epithelial-Mesenchymal Transition Generates Cells with Properties of Stem Cells*, Cell. 133:704-15 (2008). It has also been proposed that cancer stein cells are responsible for the formation of macroscopic metastases. In line with these observations, our preliminary data suggest that TG2-induced EMT in mammary epithelial cells can confer stein cell phenotype ($CD44^{high}/CD24^{-/low}$). Currently we are further characterizing the TG2-induced stein cell characteristics of MCF10A and MCF12A cells, by determining their self-renewal capacity and their ability to differentiate into multiple lineages.

Aberrant expression of TG2 in epithelial cells results in constitutive activation of FAK, Akt, and NT-κB signaling pathways. Verma A, et al., *Tissue Transglutaminase Regulates Focal Adhesion Kinase/AKT Activation by Modulating PTEN Expression in Pancreatic Cancer Cells*, Clin Cancer Res., 14:1997-2005 (2008); Mann A P, et al., *Overexpression of Tissue Transglutaminase Leads to Constitutive Activation of Nuclear Factor-κβ in Cancer Cells: Delineation of a Novel Pathway*, Cancer Res. 66:8788-95 (2006); Kim, D. S., et al., *Reversal of Drug Resistance In Breast Cancer Cells by Transglutaminase 2 Inhibition and Nuclear Factor-κβ Inactivation*, Cancer Res. 66:10936-43 (2006); Shao, M., et al., *Epithelial-to-Mesenchymal Transition and Ovarian Tumor Progression Induced by Tissue Transglutaminase*, Cancer Res. 69:9192-201 (2009). These pathways are known to be intimately involved in the EMT. Wang, Z., et al., *Acquisition of Epithelial-Mesenchymal Transition Phenotype of Gemcitabine-Resistant Pancreatic Cancer Cells is Linked with Activation of the Notch Signaling Pathway*, Cancer Res, 69:2400-7 (2009); Kalluri R, et al., The Basics of Epithelial-Mesenchymal Transition, J Clin Invest., 119:1420-28 (2009). Therefore, constitutive activation of these pathways plays a role in TG2-induced EMT. There is crosstalk between TG2 and TGF-β: TG2 activates TGF-β and TGF-β can induce TG2 expression. Telci, D., et al., *Increased TG2 Expression can Result in Induction of Transforming Growth Factor Beta1, Causing Increased Synthesis and Deposition of Matrix Proteins, Which can be Regulated by Nitric Oxide*, J. Biol. Chem., 284:29547-58 (2009); Nunes, I, et al., *Latent Transforming Growth Factor-β Binding Protein Domains Involved in Activation and Transglutaminase-Dependent Cross-Linking of Latent Transforming Growth Factor-β*, J. Cell Biol., 36:1151-63 (1997); Ritter, S. J., et al., *Identification of a Transforming Growth Factor-β1/Bone Morphogenetic Protein 4 (TGF-β/BMP4) Response Element Within the Mouse Tissue Transglutaminase Gene Promoter*, J Biol. Chem., 273:12798-806 (1998). Although TGF-β is a well-known inducer of EMT in both normal and pathological conditions, activation of TGF-β signaling in TG2-transfected MCF-10A cells does not appear. Thiery, J. P., et al., *Epithelial-Mesenchymal Transitions in Development and Disease*, Cell, 39:871-90 (2009); Xu, J., et al., *TGF-β-Induced Epithelial to Mesenchymal Transition*, Cell Res., 19:156-72 (2009). On the contrary, TGF-β failed to induce complete EMT in the absence of TG2, suggesting that TG2 is an important downstream mediator of TGF-β-induced EMT program.

Figure 6:
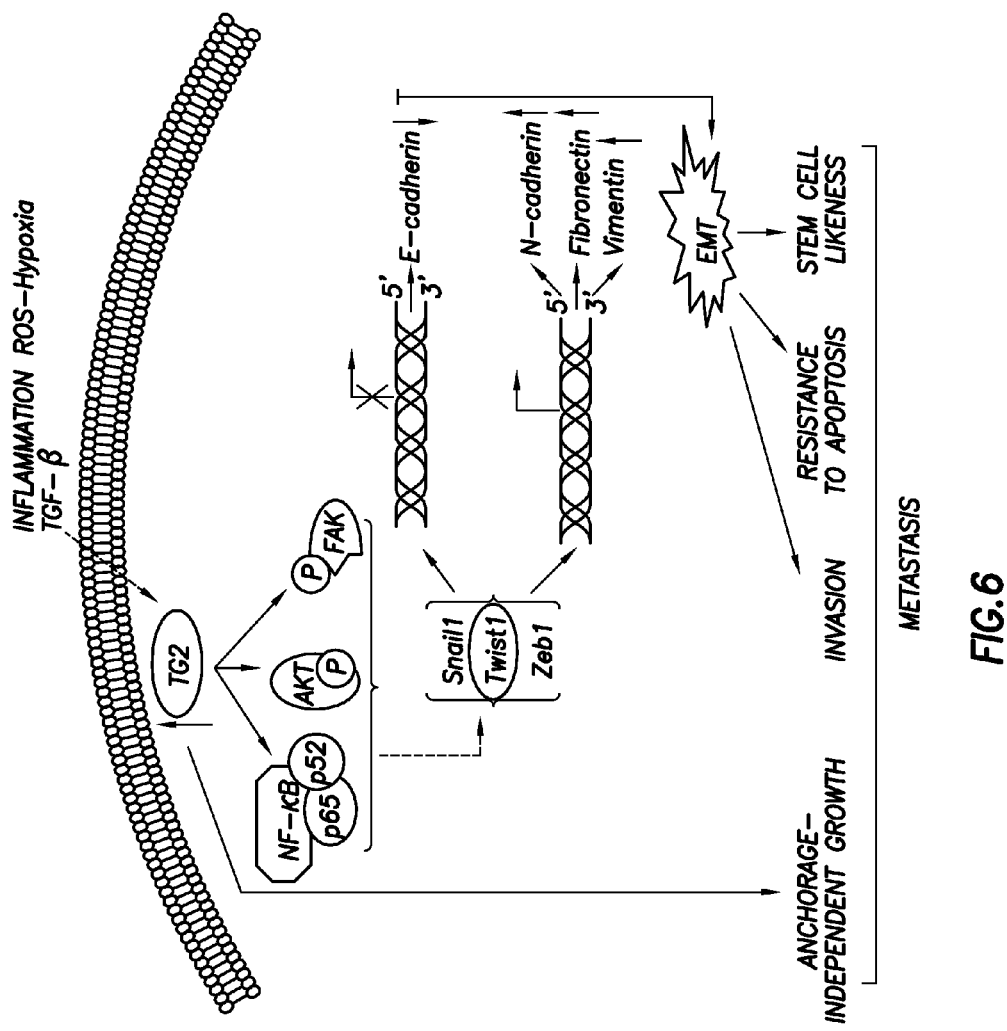
FIG. 6 is a schematic of TG2-indeed pathways involved in promoting the metastatic, phenotype. Inflammatory signals such as generation of ROS⁻, hypoxia, or TGF-β induce the expression of TG2 in epithelial cells. Induction of TG2 results in constitutive activation of AKT, FAK and NF-κB, which can lead to the transcriptional regulation of Snail1, Zeb1, and Twist. Expression of these transcription factors represses the E-cadherin and induces the expression of fibronectin, N-cadherin and vimentin. These changes result in transformation of immotile epithelial cells to motile mesenchymal cells resulting in altered cell-cell (homotypic) and cell-ECM (heterotypic) interactions and hence offers metastatic niche to the cells in terms of increased invasiveness, survival and self-renewing capacity by conferring stein cell-like phenotype. TG2 expression also promotes anchorage-independent growth.
Figure 7A:
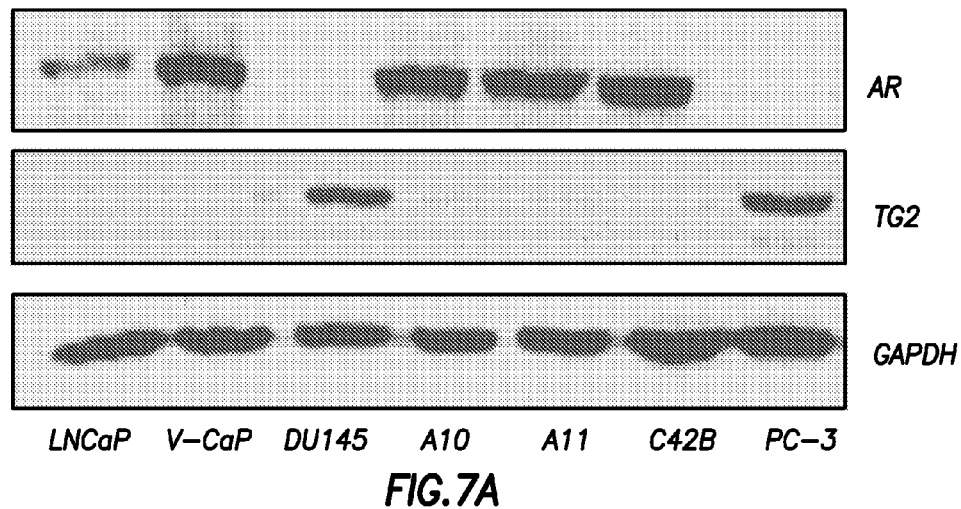
FIGS. 7A and 7B show androgen-receptor negative cells express high basal levels of TG2 protein.
Figure 7B:
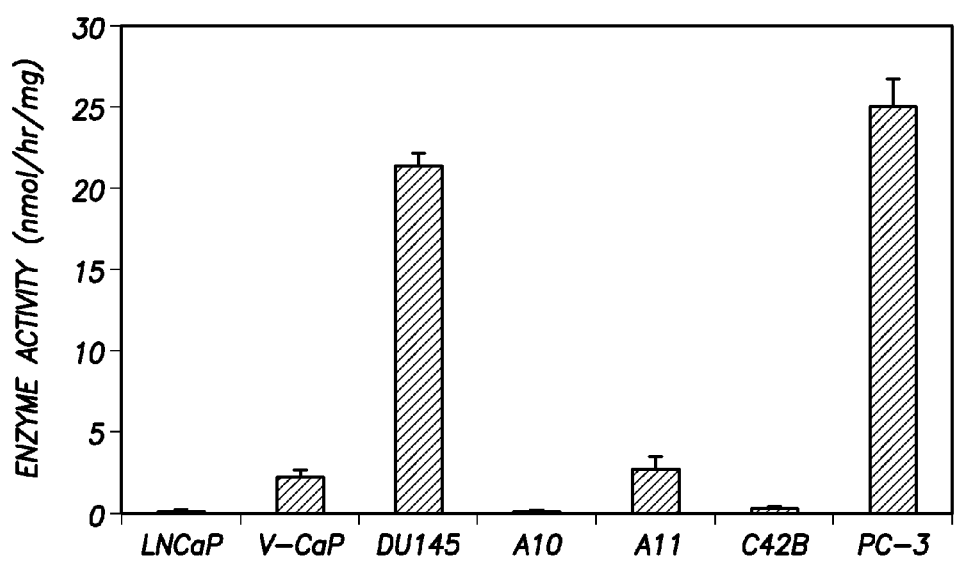
Figure 9B:
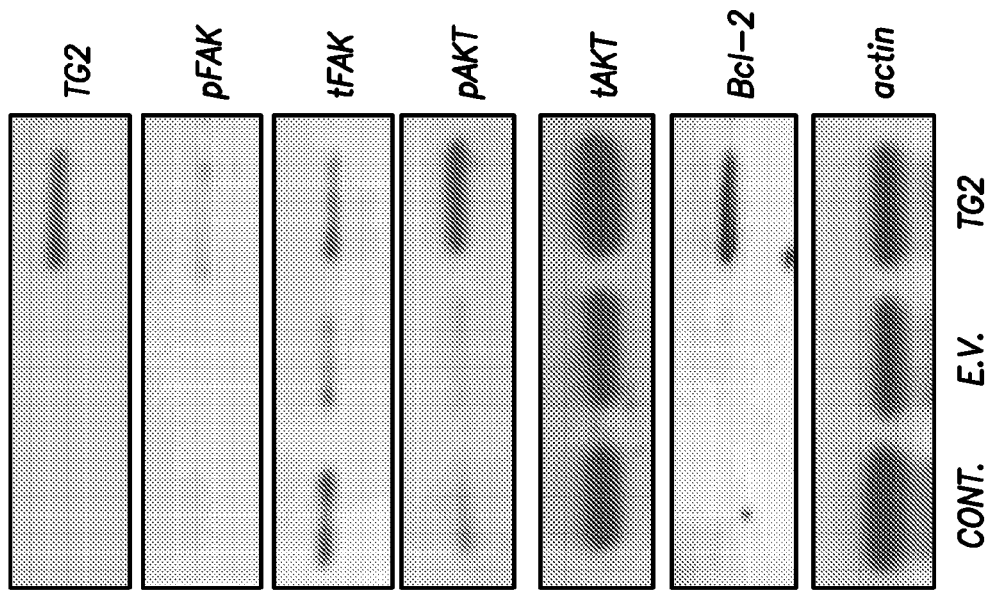
FIGS. 9A and 9B show TG2 expression promotes invasion and induce cell survival signaling in LNCaP cells.
Figure 9A:
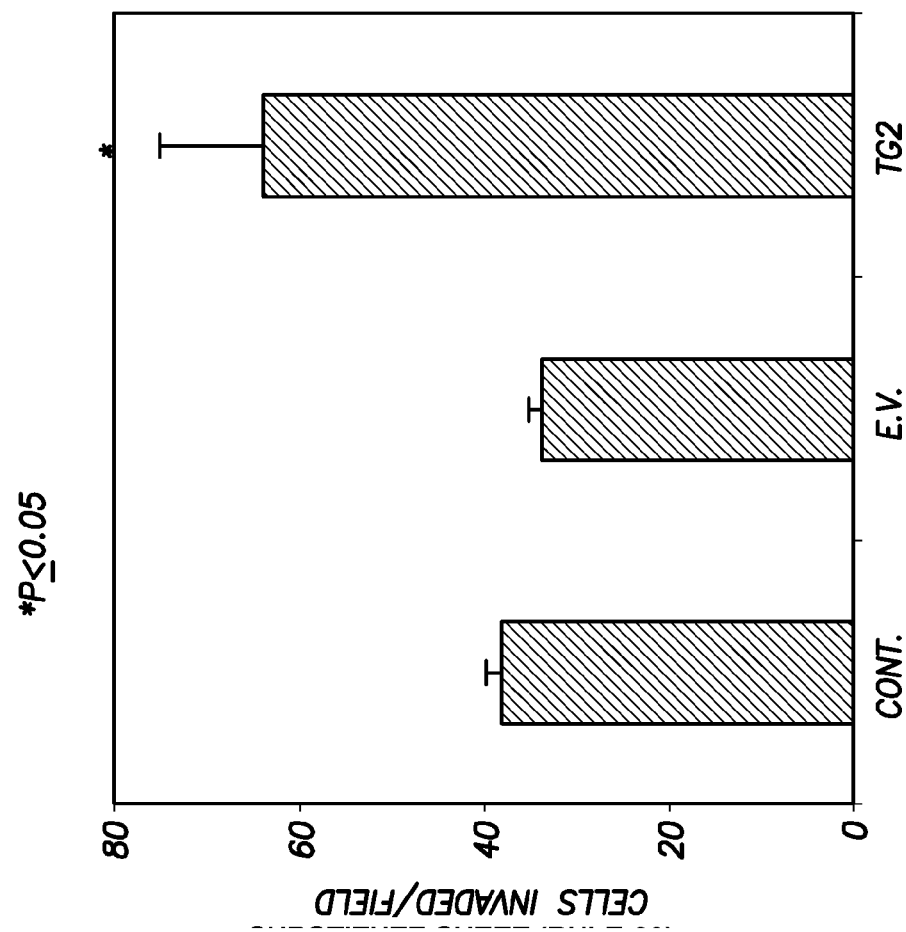
Figure 10B:
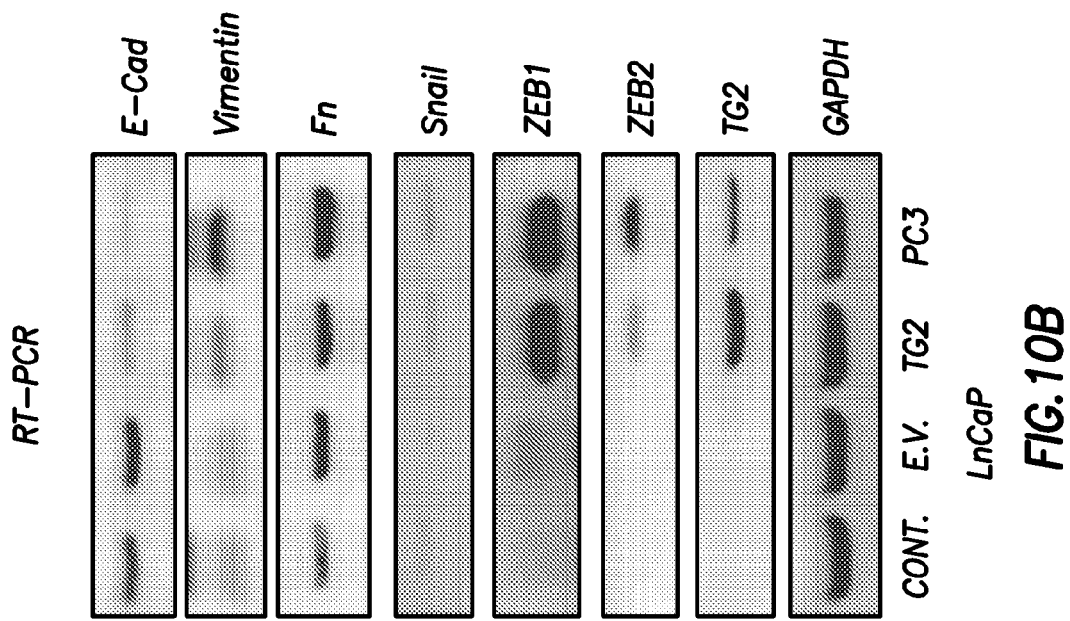
Figure 10A:
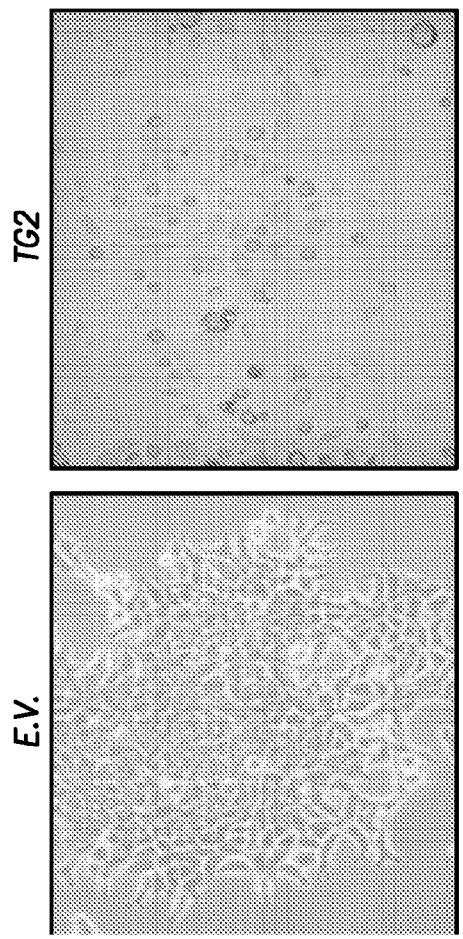
Figure 14:
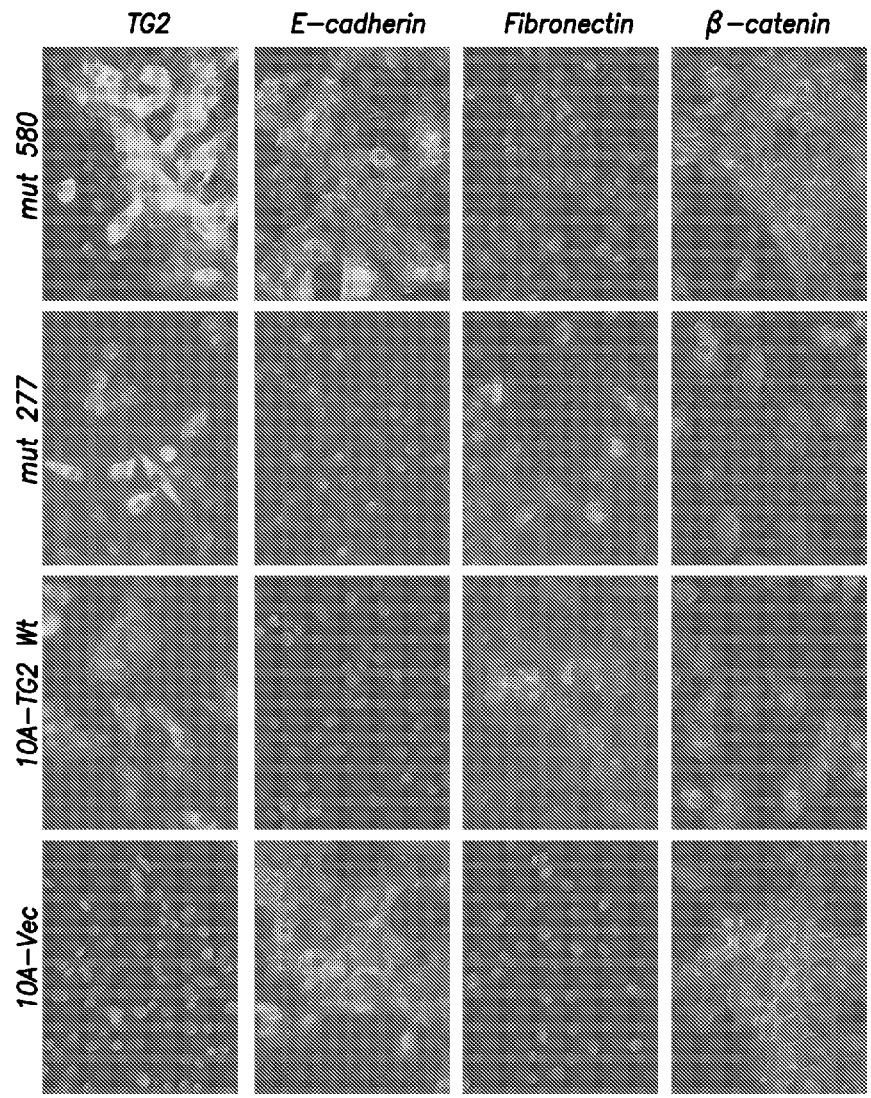
FIG. 14 also shows R580K mutant of TG2 failed) induce EMT functions in MCF10A cells.
Figure 15:
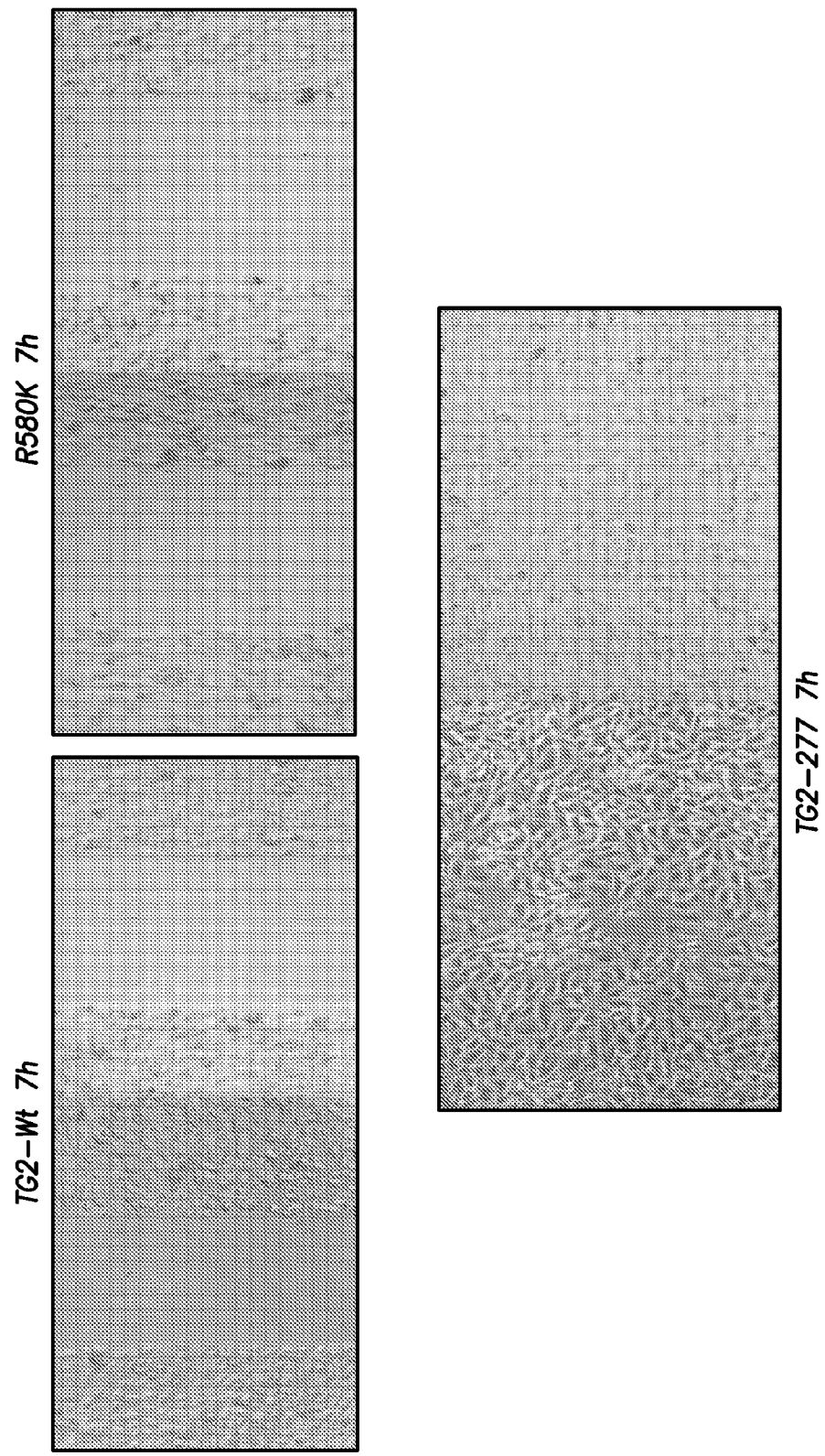
FIG. 15 shows catalytically inactive mutant, of TC12 promotes cell motility in MCF10A cells.
Figure 16:
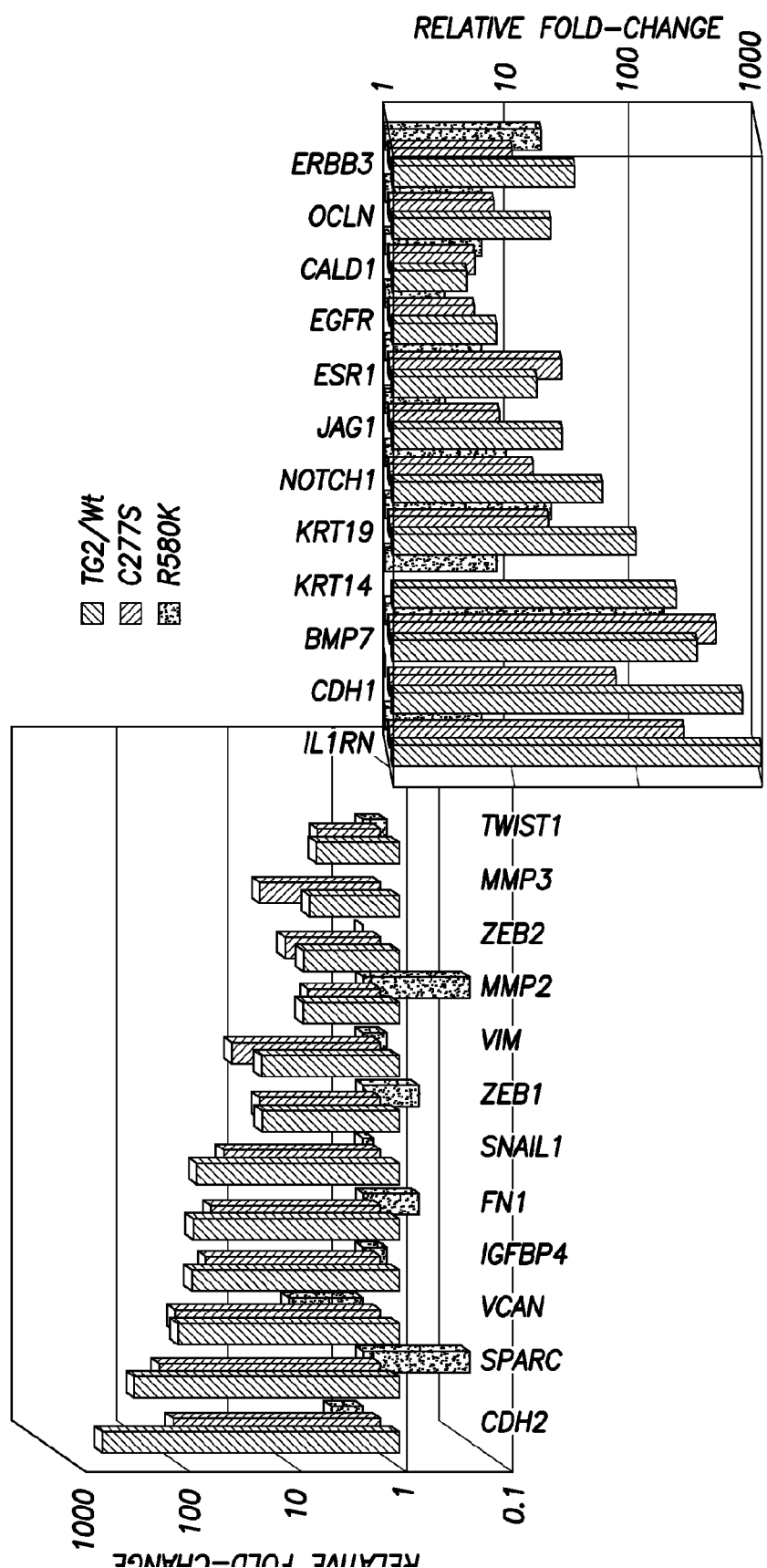
FIG. 16 provides charts that show the relative EMT gene profile of MCF10A cells expressing TG2 wt or TG2/C277S or TG2/R580K mutant.
Figure 17A:
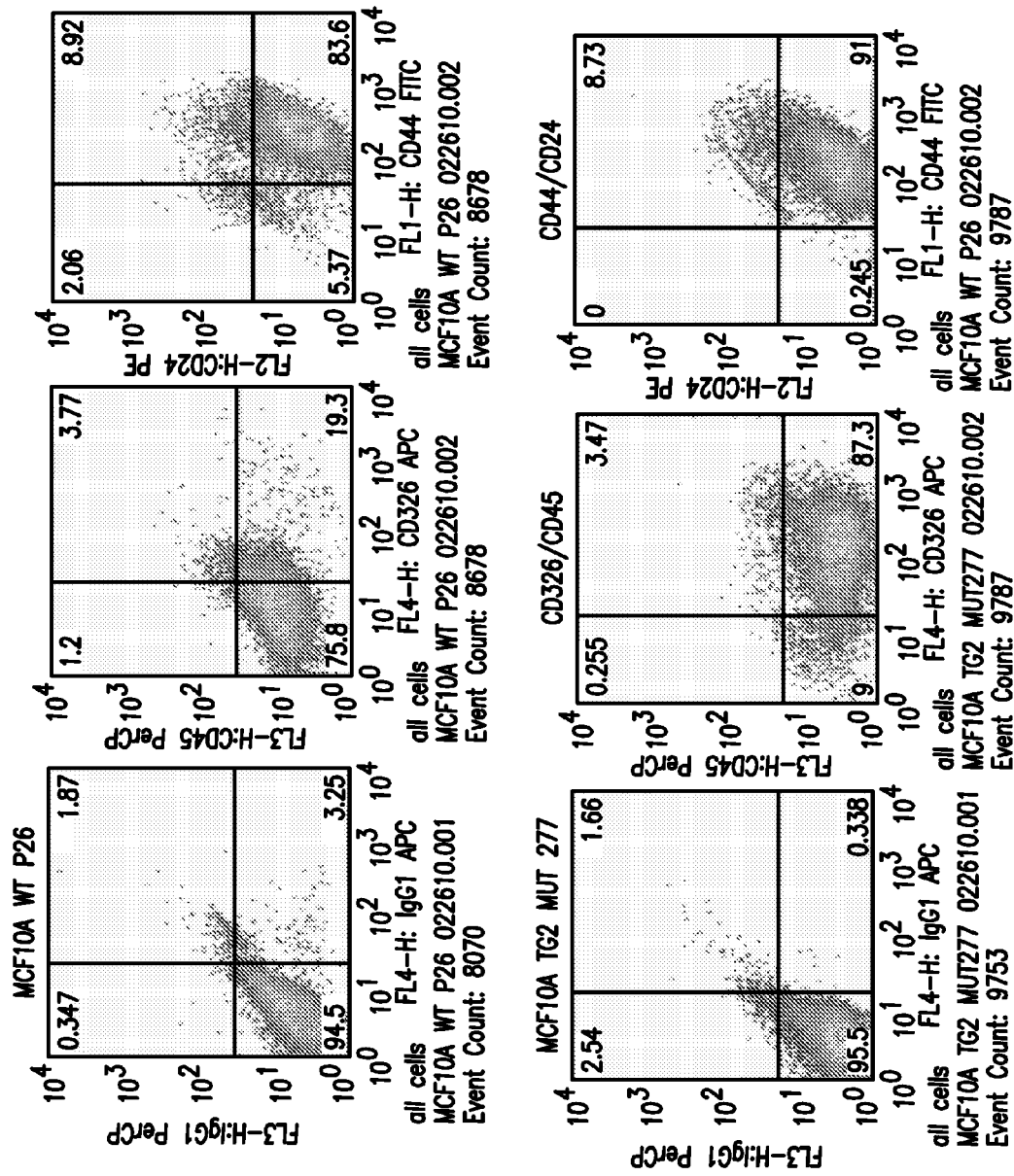
FIG. 17 provides data that shows that TG2/wt and TG2/C277S mutant induce stem cell phenotype, but R580K mutant is unable to do so in MCF10A cells.
Figure 17B:
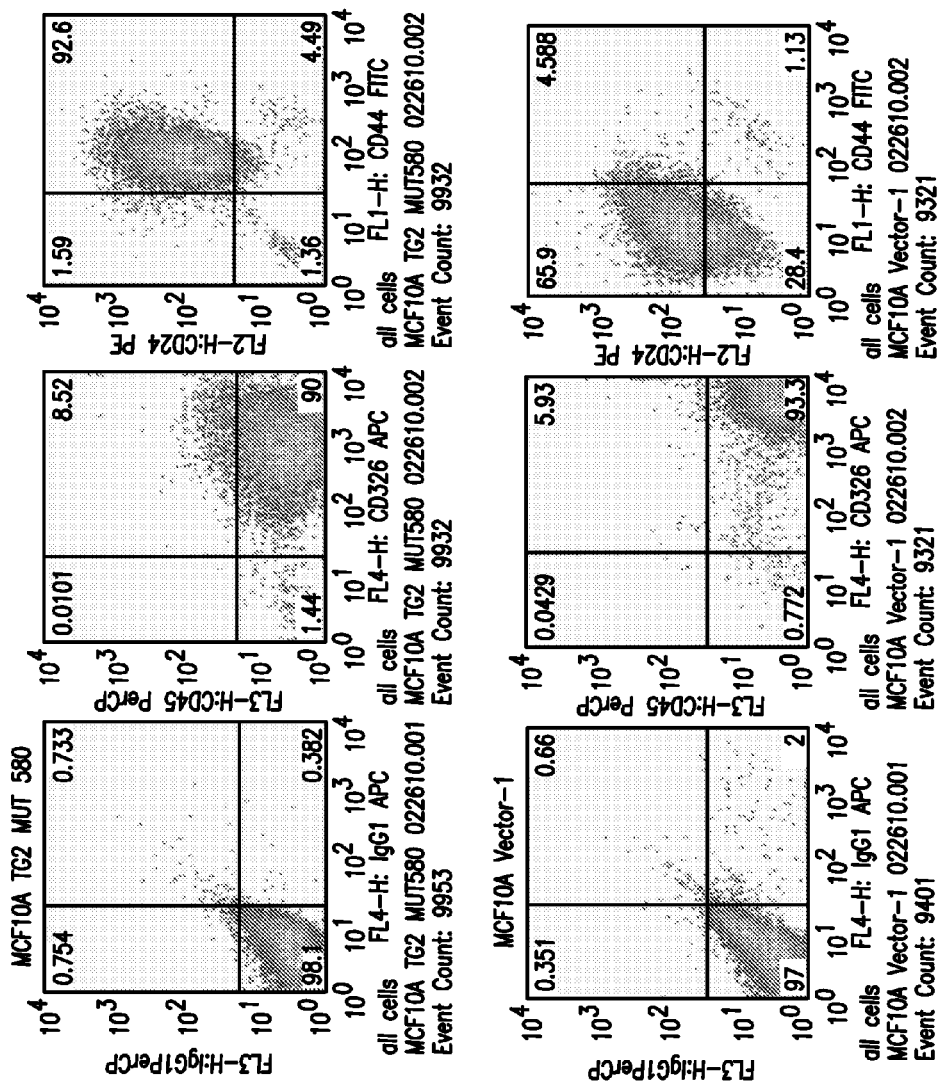
Figure 18B:
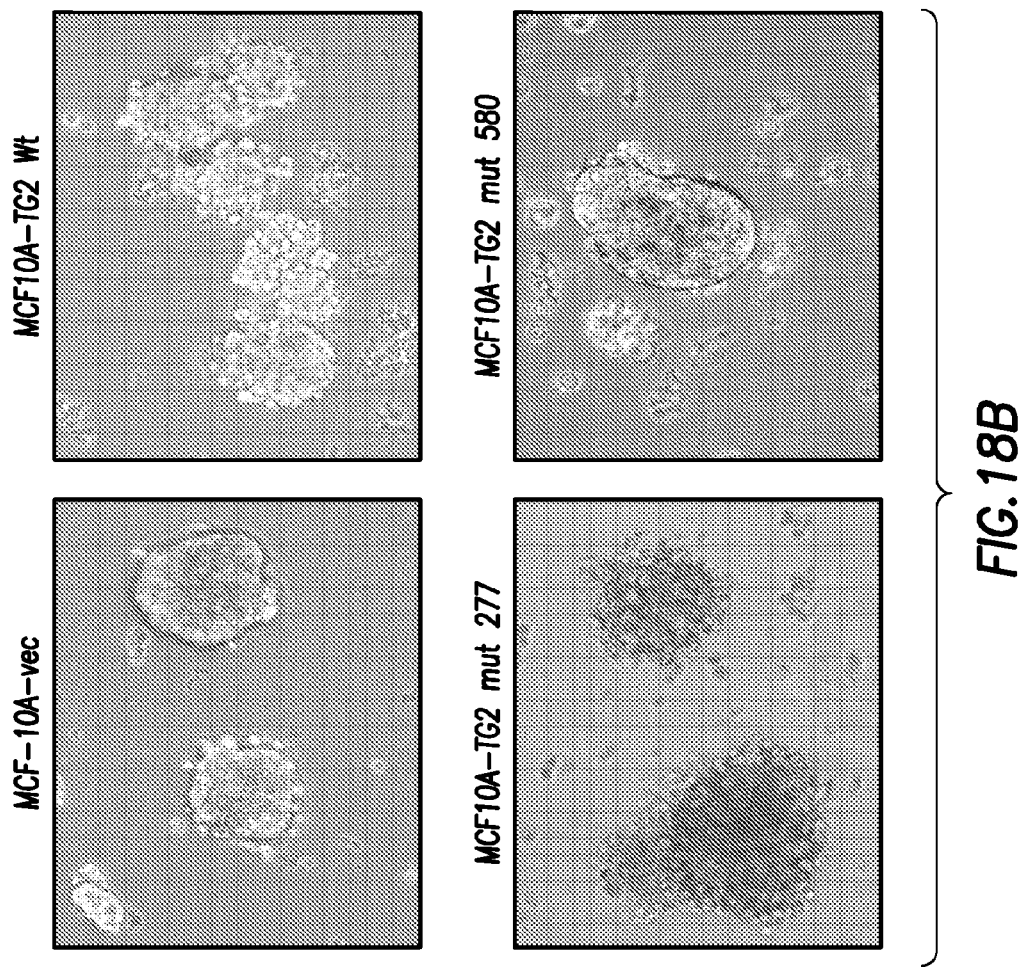
Figure 18A:
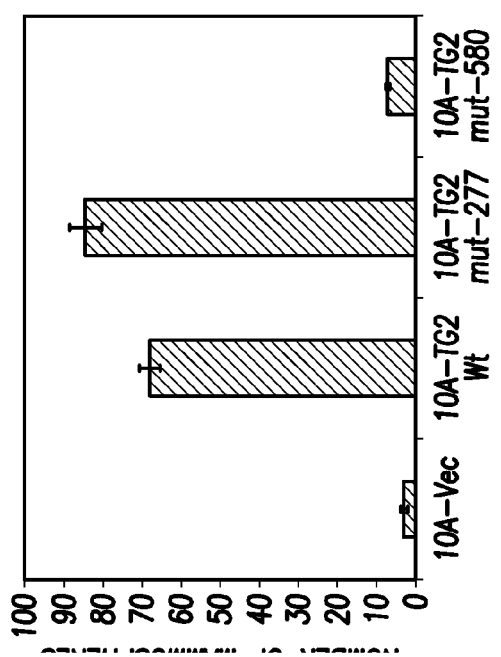
Figure 21:
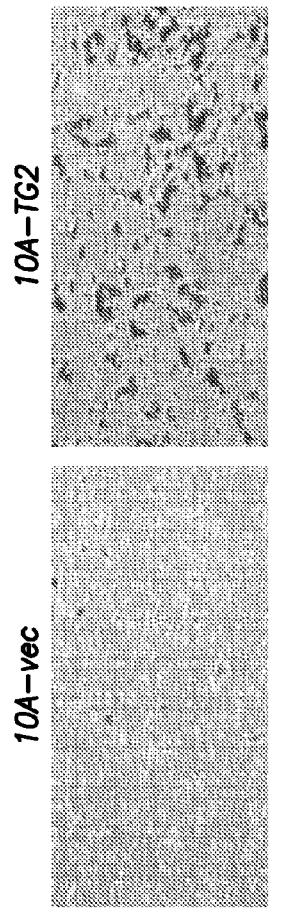
FIG. 21 shows the MCF10A-vec cells grew into well-organized acinar-like structures.

Furthermore, we observed that TG2-induced EMT in mammary epithelial cells could promote anchorage-independent growth and tumorigenic potential. Our in vitro data clearly support that over expression of TG2 in mammary epithelial cells is sufficient to induce malignant phenotype. Aberrant expression of TG2 contributes to the transformation of primary breast cancer to metastatic capabilities (FIG. 6) and TG2 is a promising therapeutic target for drug-resistant and metastatic breast cancer.

Example II

GTP Binding Function is Essential for Mesenchymal Transition

Materials and Methods
Materials.

The immortalized human mammary epithelial cells (MCF10A) were maintained as previously described (Kumar et al., 2010). Wild-type (WT) and mutant TG2 constructs (C277S, W241A and TG2-R580A) were stably expressed in MCF10A cells by retroviral transfection and selection against puromycin as previously described. Kumar, A., et al., *Tissue Transglutaminase Promotes Drug Resistance and Invasion by Inducing Mesenchymal Transition in Mammary Epithelial Cells*, PLoS One 5: e13390 (2010). Multiple stable clones were used to rule out potential clonal effects.

In Situ Transglutaminase Activity and GTP-Agarose Pull-Down Assay.

In situ transglutaminase activity of different TG2 constructs was determined by 5'-(biotinamido) pentylamine (BPA; Pierce, Rockford. IL) conjugation to cellular proteins as previously described. Fok et al., 2006. Briefly, cells were plated in 6-well-plates and incubated with 1 mM BPA overnight, followed by 8 h treatment with A23187 calcium ionophore (4 μM) to induce cytosolic calcium and TG2 activation. At the end of incubation period, cells were lysed and equal amounts of proteins fractionated by SDS-PAGE. Proteins were transferred onto nitrocellulose membrane and probed with HRP-conjugated streptavidin (GE Healthcare, CA). The membranes were stripped and reprobed with anti-TG2 moAb (CUB7401; Neomarkers, Fremont, Calif.) or α-actin antibodies to establish TG2 expression or even protein loading, respectively.

GTP-agarose pull-down assay was performed to check the GTP-binding ability of different TG2 constructs according to the procedure described by Gundemir et al. (2009). Briefly, cells were rinsed in ice-cold PBS and collected in GTP-binding buffer (20 mM Tris-HCl, pH 7.5, 5 mM MgCl2, 2 mM PMSF, 20 mg/mL leupeptin, 20 mg/mL pepstatin, 10 mg/mL aprotinin, 300 mM NaCl and 0.5% Triton-X). Samples were sonicated for 15 s and centrifuged (13,000 g for 10 min) at 4° C. The supernatants were collected and 100 μg of lysate protein were incubated with 100 μL GTP-agarose beads (Sigma-Aldrich, St Louis, Mo.) for 30 min at 4° C. in 500 μL total volume of GTP-binding buffer. The beads were centrifuged at 10,000 g for 2 min and the supernatant was retained. The beads were washed three times with 1 ml of GTP-binding buffer and the retained supernatant was incubated with the beads for overnight at 4° C. The beads were washed again as described above and bound proteins were eluted by boiling the beads in 50 μL of 2× reducing sample buffer. The GTP-agarose-bound TG2 was visualized by immunoblotting of the eluted proteins.

Western Blotting, and Immunofluorescence.

For Western blots, cells were lysed on ice in 50 mM Tris-HCl buffer, pH 7.5 containing 150 mM NaCl and 0.5% NP-40. Fifty micrograms of total protein from each sample were resolved on a 4%-12% SDS Bis-Tris-polyacrylamide gel with running buffer and transferred onto nitrocellulose membranes. The membranes were then probed with various antibodies. Immunofluorescence staining of cells in monolayer and 3D cultures was done as previously described. Kumar, A., et al., *Tissue Transglutaminase Promotes Drug Resistance and Invasion by Inducing Mesenchymal Transition in Mammary Epithelial Cells*, PLoS One 5: e13390 (2010).

RT-PCR and NF-κB Knockdown.

Quantitative RT-PCR for EMT-associated genes was done using SABiosciences (Frederick, Md.) EMT-PCR Array according to the manufacturer's protocol. Expression of p65 subunit of NF-κB was knocked down using two different p65 siRNA sequences (Cell Signaling Technology, Danvers, Mass.) as previously described. Mangala, L. S., et al., *Tissue Transglutaminase Expression Promotes Cell Attachment, Invasion and Survival in Breast Cancer Cells*, Oncogene 26: 2459-2470 (2007).

Cell Migration, Invasion, Colony Formation, Cell Viability and NF-κB Activity.

Cell migration, invasion, cell viability, and NE-KB activity were assayed were as previously described. Mangala, L. S., et al., *Tissue Transglutaminase Expression Promotes Cell Attachment, Invasion and Survival in Breast Cancer Cells*, Oncogene 26: 2459-2470 (2007); Herman, J. F., et al., *Implications of Increased Tissue Transglutaminase (TG2) Expression in Drug-Resistant Breast Cancer (MCF-7) Cells*, Oncogene 18:25:3049-3058 (2006); Mann, A. P., et al., *Overexpression of Tissue Transglutaminase Leads to Constitutive Activation of Nuclear Factor-Kappab in Cancer Cells: Delineation of a Novel Pathway*, Cancer Res. 66: 8788-8795 (2006). Soft agar assay was performed as described Kumar, A., et al., *Tissue Transglutaminase Promotes Drug Resistance and Invasion by Inducing Mesenchymal Transition in Mammary Epithelial Cells*, PLoS One 5: e13390 (2010). Cultures were photographed and the colonies with diameters larger than 500 mm were counted.

Mammosphere Culture and Differentiation

Mammosphere culture and their differentiation were done as described by Dontu, G., et al., *Stem Cells in Normal Breast Development and Breast Cancer*, Cell Prolif 36: 59-72 (2003). Briefly, after 7-10 days of culture in mammocult medium (Stem Cell Technology, Vancouver, Canada), the mammospheres generated with diameter >75 μm were counted. For serial passages, matrimospheres were collected by gentle centrifugation (800 rpm) and dissociated enzymatically (10 min in 0.05% trypsin containing 0.53 mM EDTA) and mechanically, using a fire-polished Pasteur pipette as described. Kumar, A., et al. *Evidence that Aberrant Expression of Tissue Transglutaminase Promotes Stem Cell Characterstics in Mammary Epithelial Cells*, PLoS One 6: e20701 (2011). For differentiation, individual mammaospheres were grown for 10-12 days in 3D Matrigel culture in the presence of prolactin (2 μg/ml).

Results

TG2 Expression in MCF10A Cells.

Figure 26D:
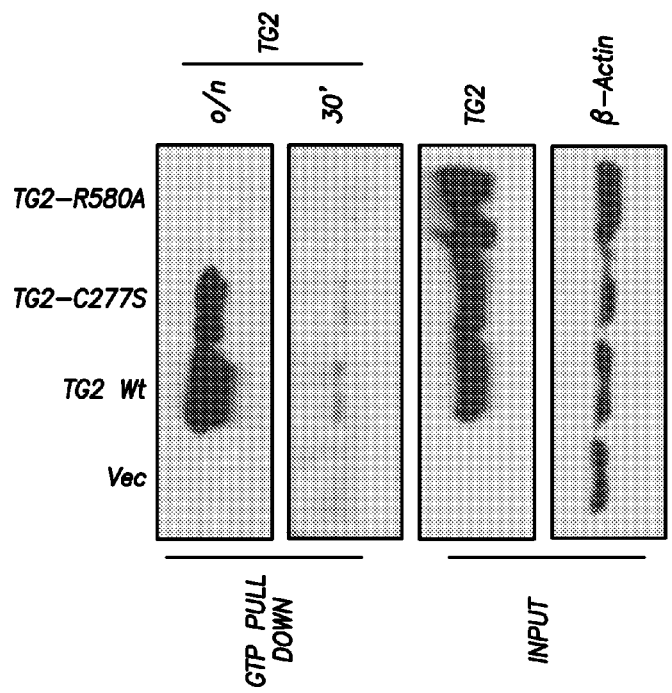
Figure 26C:
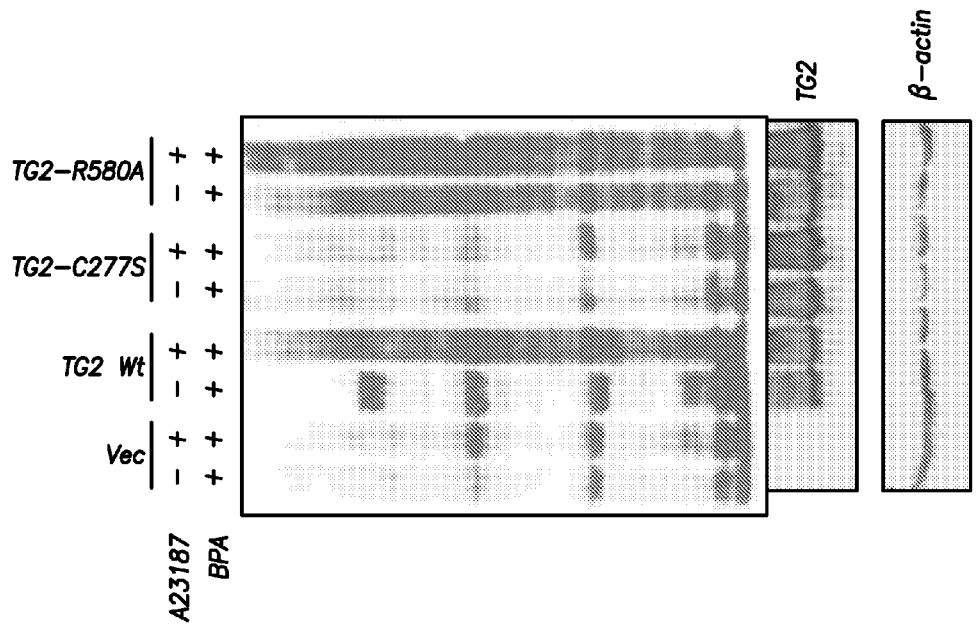

The expression of various TG2 constructs in MCF10A cells was determined by immunoblotting (FIG. 26A). MCF10A cells transfected with wt-TG2 (10ATG2-WT) served as positive control. All the three TG2 proteins, the TG2-WT as well as mutant TG2 lacking the transamidation activity TG2-C277S and TG2-W241A) or the GIMP-binding activity (TG2-R580A) migrated as a single 78 kDa size band. The level of TG2 expression was slightly higher in 102-R580A transfected MCF10A cells (10ATG2-580) compared to the TG2-C277S (10ATG2-277) and TG2-WT transfected cells (10ATG2-WT). No detectable expression of TG2 was observed in vector-transfected cells (10A-Vec). Expression of TG2 in these cells was further confirmed by immunostaining, which revealed that all three forms of TG2 are predominantly localized in the cytosolic compartment (FIG. 26B). To determine transglutaminase activity of different TG2 constructs, in situ transamidation activity was performed by studying the conjugation of 5-(biotinamido) pentylamine (BPA) to cellular proteins. Calcium ionophore, A23187 was used to induce intracellular $Ca^{2+}$ and activation of TG2. As expected, no BPA conjugation was evident in cells lacking the TG2 expression (10A-vec) or harboring catalytically inactive mutant protein (10ATC2-277), while 10ATG2-WT and 10ATG2-580 cells showed significant conjugation of BPA to multiple cellular proteins. Both, the basal as well as A23187-induced conjugation of BPA were much higher in 10ATG2-580 cells (FIG. 26C). These results suggested that 10ATG2-580 cells have constitutive active transglutaminase activity due to lack of GTP-binding function while 10ATG2-277 cells are deficient in transglutamination activity even in presence calcium ionophore. In order to determine the GTP-binding ability of different TG2 constructs, GTP agarose pull-down assay was performed. Results shown in FIG. 26D confirmed that only TG2-WT and C277S-TG2 bind to the GTP-agarose. The extent of GTP binding to C277S-TG2 was relatively less than the TG2-WT, as previously reported Gundemir, S., et al. *Intracellular Localization and Conformational State of Transglutaminase 2: Implications for Cell Death*, PLoS One, 4:e6123 (2009). The R580ATG2 failed to bind GTP agarose even after overnight incubation. The GTP-binding ability of TG2 proteins is TG2-WT>TG2-277>TG2-580 in that order.
GTP-Binding Function of TG2 is Essential for Inducing Mesenchymal Transition.

We previously found that neoexpression of TG2 results in induction of the EMT in not stormed MCF10A and MCF12A mammary epithelial cells. Kumar, A., et al., *Tissue Transglutaminase Promotes Drug Resistance and Invasion by Inducing Mesenchymal Transition in Mammary Epithelial Cells*, PLoS One 5: e13390 (2010). Similar to the 10ATG2-WT cells, 10ATG2-C277S and 10ATG2-W241A cells acquired spindle shaped morphology and exhibited scattered distribution with fibroblast-like appearance (FIG. 27A). The 10ATG2-R580A cells in contrast, appeared similar to the control vector-transfected 10A-vec cells with cobblestone-like epithelial appearance and tight cell-to-cell junctions (FIG. 27A). GTP-binding activity of TG2 is essential for inducing the EMT in MCF10A cells.

Various EMT-related molecular alterations in TG2 transfected cells were studied. Results are shown in FIG. 28A and demonstrate that similar to the 10A-Vec cells, 10ATG2-R580A cells expressed high levels epithelial maker proteins (E-cadherin and β-catenin) while minimal or undetectable levels of mesenchymal marker proteins (fibronectin, vimentin, and N-cadherin). The 10ATG2-WT, 10ATG2-C277S and 10ATG2-W241A cells, in contrast, showed almost complete loss of E-cadherin, decrease in β-catenin, and increased expression of mesenchymal markers (N-cadherin, fibronectin and vimentin; FIG. 27B). The changes were further confirmed by immunofluorescent staining. 10A-vec and 10ATG2-580 cells showed distinct membranous staining for E-cadherin and diminished staining for fibronectin.

Figure 27C:
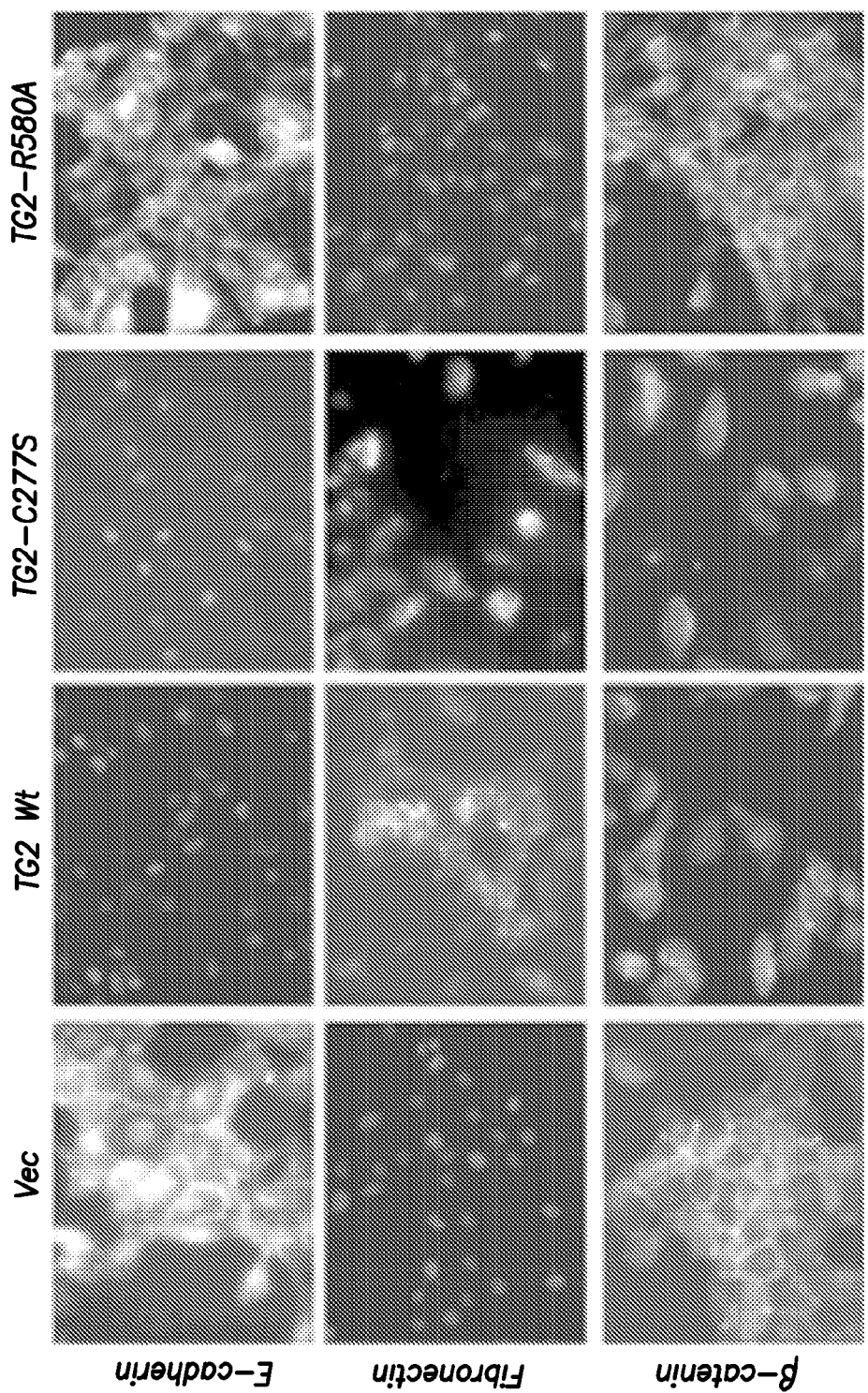
Figure 28A:
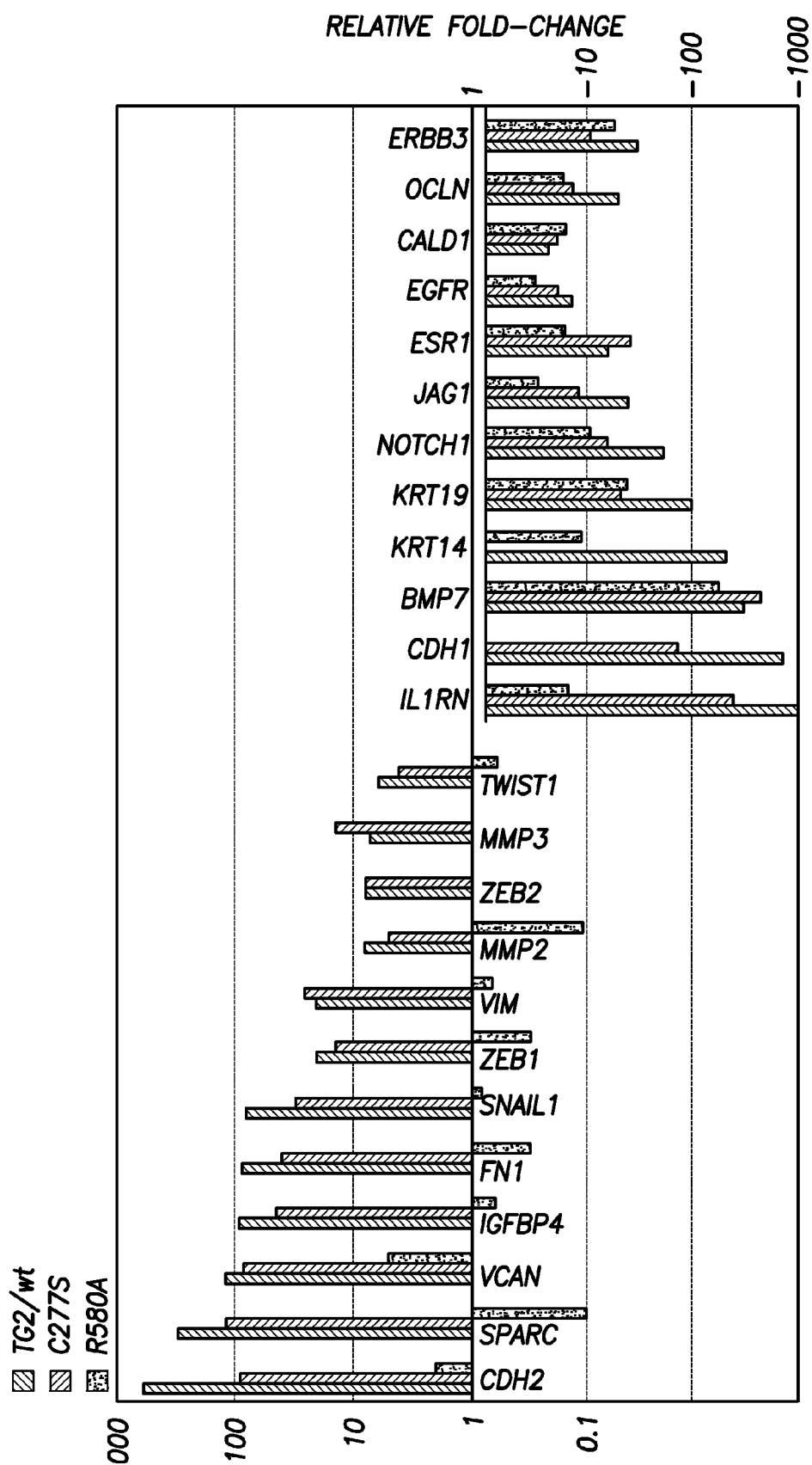
FIGS. 28A, 28B and 28C show GTP-binding inactive TG2 is unable to induce the EMT transcription repressors. Specifically, real time RT-PCR array showing changes in the expression of EMT-related genes in MCF10A sublines expressing WT or mutant constructs of TG2 relative to changes observed in control vector-transfected MCF10A cells. Y-axis denotes the fold-change in transcript levels, blue bars denote the gene expression in TG2-WT cells, red bars denote gene expression in TG2-C277S, and green bars denote gene expression in TG2-R580A cells. The expression of GAPDH, β-actin and 18S ribosomal RNA was used to normalize variable template loading.

In contrast, 10ATG2-WT and 10ATG2-C277S cells showed no E-cadherin staining and increased fibronectin staining (FIG. 27C). Overall, these results show that aberrant expression of WT or catalytically inactive (C277S and W241A) TG2 mutant is effective in promoting the EMT phenotype and that GTP-binding function of TG2 is critical to this effect.
GTP-Binding Activity of TG2 is Essential for Snail, Twist, and Zeb Expression Induction of EMT involves complex molecular alterations primarily choreographed by transcription factors, such as Snail1, Slug, Twist, Zeb1, Zeb2, E12, E47 (Kalluri, 2009; Kalluri and Weinberg, 2009). To determine the effect of TG2 mutants on transcriptional regulation of EMT associated genes, we performed the transcriptional profile of EMT-associated genes using SABiosystem real-time PCR-based EMT array. Results shown in FIG. 28A demonstrate the fold-change relative to the control MCF10A-vec cells in EMT-associated genes in MCF10A cells transfected with different TG2 constructs.

The results obtained revealed several-fold decrease in the expression of epithelial marker genes such as, CDH1 (E-cadherin) KRT19 (keratin19), KRT7 (keratin 7), and OCLN (occludin) with concomitant increase in mesenchymal marker genes such as, CDT-12 (N-cadherin), VCAN (versican), (fibronectin), and VIM (vimentin) in 10ATG2-C277S and 10ATG2-WT cells. In 10ATG2-R580A cells, though slight downregulation in epithelial marker genes (KRT19, KRT7, CALD1, and OCLN) was observed but no change in CDH1 gene transcript was evident. The expression of mesenchymal marker genes such as, CDH2, VCAN, FN1, SPARC, and VIM was either unaltered or even the basal expression of these genes was downregulated in 10ATG1-R580A cells (FIG. 28A).

Figure 28C:
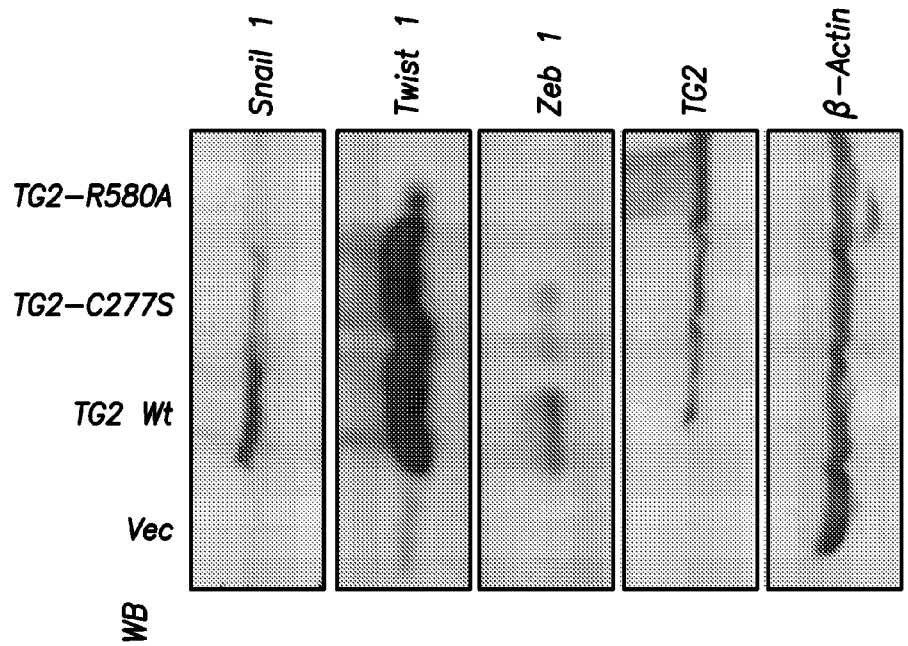
Figure 28B:
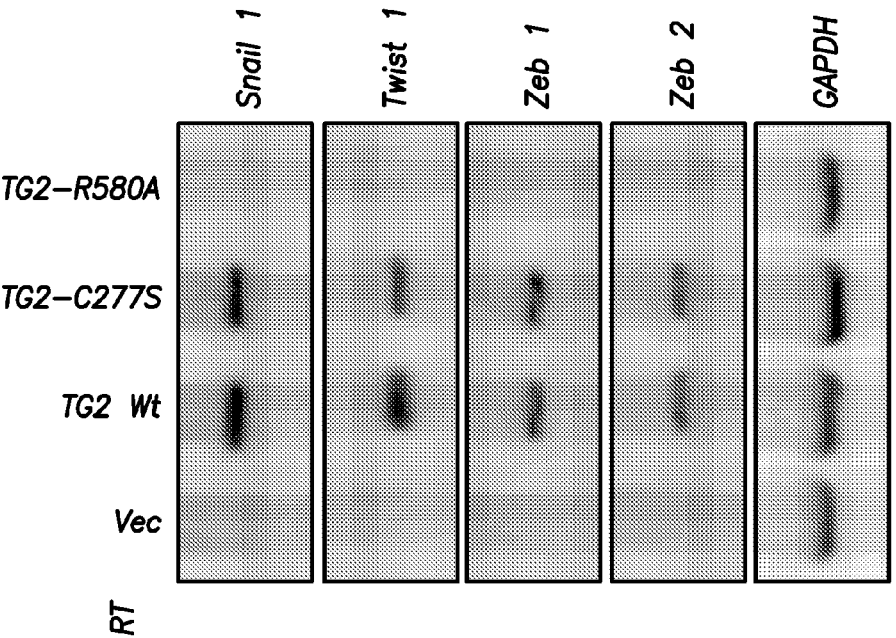

Overall, these results show that 10ATG2-WT and 10ATG2-C277S cells undergo mesenchymal transition whereas 10ATG2-R580.A cells continue to exhibit epithelial phenotype. Moreover, the expression of transcription repressors Snail1, Zeb1, Zeb2, and Twist1 in 10ATG2-WT and 10ATG2-C277S cells was upregulated while these transcription facots were downregulated iii 10ATG2-R580A cells. Altered expression of snail1, zeb1 and twist1 in response to WT and mutant TG2 expression was further validated by RT-PCR (FIG. 28B) and western blot (FIG. 28C) analysis. Transcriptional repression of E-cadherin and upregulation of fibronectin, N-cadherin and vimentin in MCF10A cells in response to TG2 expression entails intact GTP-binding activity while the transamidation activity is not essential for inducing these changes.
GTP-Binding Activity of TG2 is Essential for Promoting Invasiveness and Drug Resistance Metastasis is a multistep process and involves increased migration, protease secretion, and altered adhesion of cancer cells to allow their dissemination from primary tumor sites. Liotta, L. A., et al., *Tumor invasion and Metastasis: An imbalance of Positive and Negative Regulation*, Cancer Res. 51: 5054s-5059s (1991). In this context, our finding of stable expression of TG2-WT or TG2-C277S in MCF10A cells is associated with increased expression of metalloproteases MMP2 and MMP3 (FIG. 28A) and transition into mesenchymal cells (FIG. 27A) while TG2-R580A expression resulted in decreased MMP2 levels (FIG. 28A) without any change in the cellular morphology, is of interest. Moreover, the 10ATG2-C277S cells showed increased motility in wound-healing assay, whereas 10ATG2-WT and 10ATG12-R580A cells showed low motility, similar to the 10A-Vec cells.

To further evaluate the invasive potential, we performed Matrigel invasion assay and found that the number of cells invaded through Matrigel was significantly higher in 10ATG2-WT and 10ATG2-C277S cells compared to the 10A-vec and 10ATG2-R580A cells (FIG. 29A). These results further supported that catalytic inactive TG2 (C277S) is as effective as the WT-TG2 in inducing the EMT and promoting invasive phenotype in epithelial cells, while GTP-defective (R580A) TG2 lacked this ability.

Next we determined the effect of different TG2s in conferring resistance to doxorubicin. Results shown in FIG. 29B revealed that TG2-C277S and TG2-WT expressing cells are relatively more resistant to doxorubicin-induced killing. When compared to TG2-R580A or vector-transfected cells. Next we determined the oncogenic potential of three TG2 constructs by studying anchorage-independent growth of cells in soft-agar, an in vitro surrogate measure for the tumorigenicity. Cifone, M. A., et al., *Correlation of Patterns of Anchorage-Independent Growth with in Vivo Behavior of Cells from a Murine Fibrosarcoma*, Proc Natl Acad Sci USA. 77:1039-1043 (1980). Indeed, the catalytically inactive TG2 expressing MCF10A-C277S cells showed high frequency of colonies formation similar to the MCF10A-WT cells whereas, GTP-binding defective MCF10A-R580A cells, similar to the control MCF10A-Vec cells, failed to survive and form colonies under these conditions (FIG. 29C).

Figure 29D:
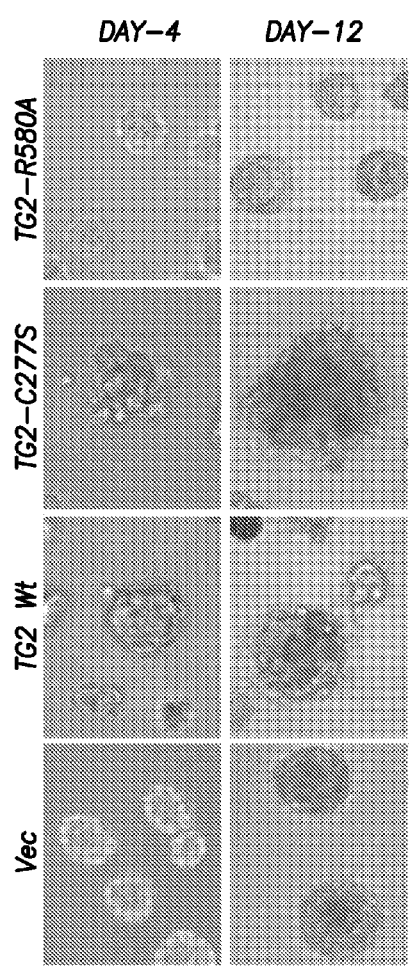
Figure 29E:
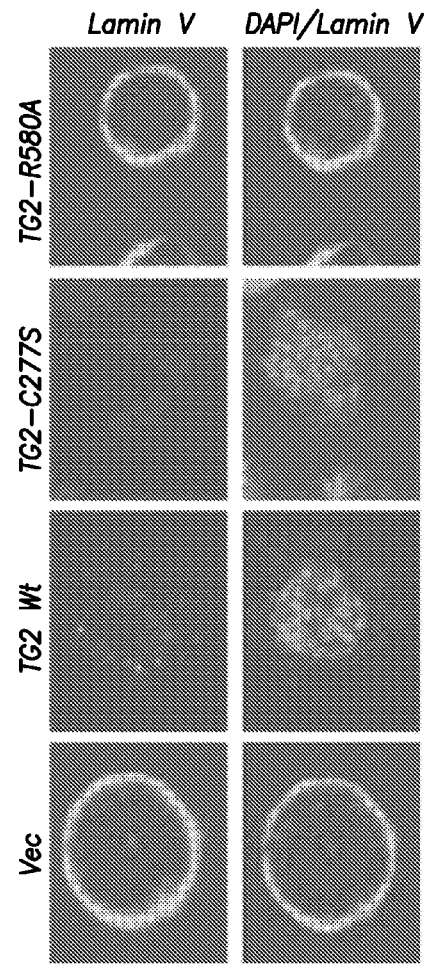

Earlier we observed that TG2 expression in MCF10A cells disrupted their normal organization into acinar structures when grown in 3D culture. Kumar, A., et al., *Tissue Transglutaminase Promotes Drug Resistance and Invasion by Inducing Mesenchymal Transition in Mammary Epithelial Cells*, PLoS One 5: e13390 (2010). Therefore, we next determined whether catalytic inactive (TG2-C277S) or GTP-binding null (R580A) TG2 mutants would have similar affect on acinar organization. Results shown in FIG. 29D demonstrated that 10ATG2-R580A cells, similar to 10A-vec cells, formed well-organized acini structures. These acinar structures contained hollow lumen with laminin V staining all around the basement layer, conferring apicobasal polarization to the cells (FIG. 29E), in addition, 10A-vec and 10ATG2-R580A generated acinar spheroids revealed strong E-cadherin expression in cells adjacent to the basal layer. In contrast, 10ATG2-C277S and 10ATG2-WT cells produced acinar spheroids with disrupted architecture they were relatively larger in size without the lumen (FIG. 29D). Moreover, these structures showed diffused laminin staining in the basement membrane (FIG. 29E) and the cells lacked E-cadherin expression. Hence, we determined that the GTP-binding function of TG2 is critical for promoting the cell motility, invasiveness, and anchorage-independent growth in mammary epithelial cells.

GTP-Binding Site of TG2 is Essential for NF-κB Activation

TG2 expression in normal and transformed cells is associated with constitutive activation of NF-κB, the transcription factor that is implicated to play a role in the DAT. Mann, A. P., et al., *Overexpression of Tissue Transglutaminase Leads to Constitutive Activation of Nuclear Factor-Kappab in Cancer Cells: Delineation of a Novel Pathway*, Cancer Res. 66: 8788-8795 (2006); Kim, D. S., et al., *Reversal of Drug Resistance in Breast Cancer Cells by Transglutaminase 2 inhibition and Nuclear Factor-Kappab Inactivation*, Cancer Res. 66:10936-10943 (2006); Thiery, J. P., *Epithelial-Mesenchymal Transitions in Tumour Progression*, Nat Rev Cancer. 2: 442-454 (2002); Shao, M., et al., *Epithelial-to-Mesenchymal Transition and Ovarian Tumor Progression Induced by Tissue Transglutaminase*, Cancer Res. 69: 9192-201 (2009).

Therefore, we next determined whether failure of TG2-R580A mutant to induce EMT is related to its NF-κB regulatory function. Results shown in FIG. 30A confirmed earlier observations that TG2-WT expression is associated with constitutive NF-κB activity in MCF10A cells. Importantly, the catalytically inactive TG2-C277S was as effective as the TG2-WT in inducing NF-κB activation whereas GTP-binding null TG2-R580A mutant was considerably less active in this regard. To determine the significance of TG2-induced NF-κB activity in the EMT process, we knockdown p65 expression in TG2 expressing MCF10A cells and determined various epithelial and mesenchymal markers.

The results obtained revealed that down regulation of p65 expression in TG2-WT cells could dramatically reverse the EMT phenotype (MET) without affecting the TG2 levels (FIG. 30B). Hence, knockdown of p65 subunit reversed the expression of Snail1, increased the expression of epithelial marker E-cadherin and reduced the expression of mesenchymal marker fibronectin without affecting TG2 expression (FIG. 30B). These results established that NF-κB activation is an important downstream mediator in TG2-induced EMT. Similarly, other mediators like activated Akt and FAK which are known to support the transition of epithelial cells to mesenchymal state, were also found activated in TG2 expressing cells, albeit the Akt activation was selectively observed in TG2-WT and TG2-C277S cells, whereas, FAK activation was evident in all three types of TG2 expressing cells (FIG. 30C).

GTP-Binding Activity and Stem Cellness

Figures 31A, 31B:
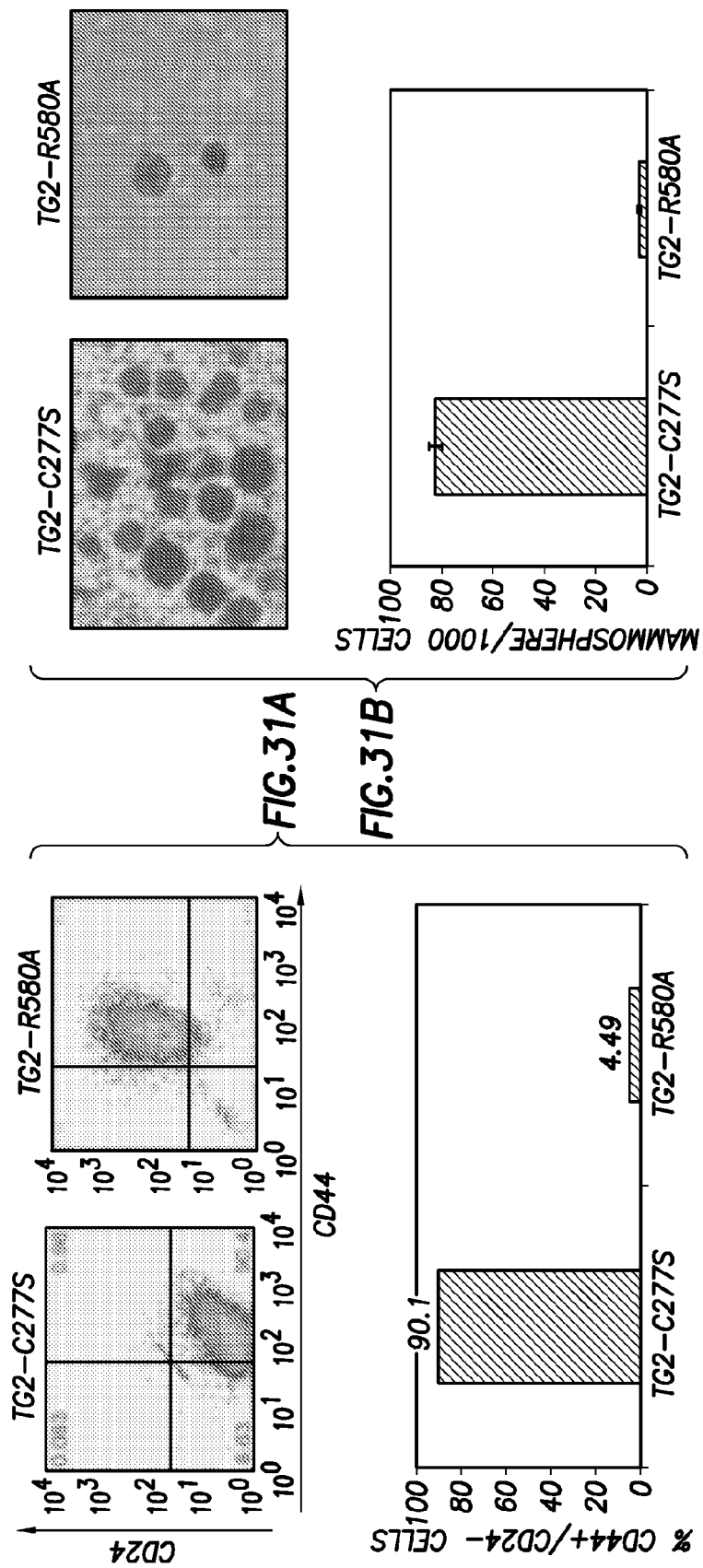

Earlier we found that TG2-induced EMT not only augments the invasive and drug resistance phenotype in mammary epithelial cells but also enhanced their plasticity by shifting dynamic equilibrium from non-stem cells to stem cells Kumar, A., et al., *Evidence that Aberrant Expression of Tissue Transglutaminase Promotes Stem Cell Characterstics in Mammary Epithelial Cells*, PLoS One 6: e20701 (2011). Therefore, we next determined whether GTP-binding function of TG2, which appears to be critical for inducting EMI, will also have impact on the acquisition of stem cell phenotype. Analysis of antigenic mammary stem cell surface markers CD44 and CD24 and the ability to form mammaospheres revealed that though TG2-WT and its catalytic inactive TG2-C277S mutant resulted in enrichment of $CD44^{high}/CD24^{low}$ cell subpopulation (FIG. 31A) and increased the number of mammosphere formed (FIG. 31B), the GTP-defective TG2-R580A mutant failed to do so (FIG. 31).

Similarly, we tested the self-renewal capability of cells using an in vitro assay that relies on assessing the sphere-initiation efficiency of serially passaged cells cultured as mammospheres. Once again, it became evident that WT-TG2 and TG2-C277S are equally efficient in promoting self-renewal ability of MCF10A mammospheres (FIG. 31C). In contrast, the TG2-R580A expressing cells showed progressive decrease in the number of mammosphere-forming cells with each passage (FIG. 31D). Another important feature of stem cells is their ability to differentiate into multiple lineages. In order to determine how TG2 mutations could affect the ability of stem cells to differentiate into secondary strictures, we transferred individual mammospheres into Matrigel cultures. Under these culture conditions, the mammospheres derived from either TG2-C277S or TG2-R580A expressing cells differentiated and formed complex secondary structures representing mammary gland-like organotypic outgrowths (FIG. 31E). Immunostaining of these secondary structures revealed the presence of both Mud (luminal marker) and CD49f/integrin α6 (basal marker)-positive cells in both the TG2-C277S and TG2-R580A transfected MCF10A secondary structure (FIG. 31F). These results further supported that R580A mutation though inhibits the TG2 ability to induce EMT and to promote sternness in mammary epithelial cells but do not interfere with their ability to terminally differentiate.

We claim:

1. A compound of the formula:

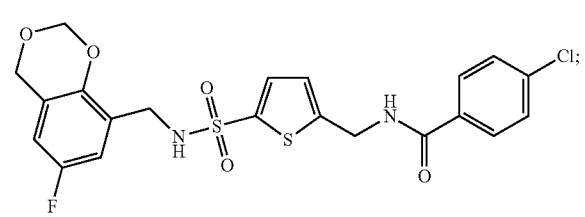 [SMILES: O=C(NCc1ccc(S(=O)(=O)NCc2cc(F)cc3c2OCOC3)s1)c1ccc(Cl)cc1]

or

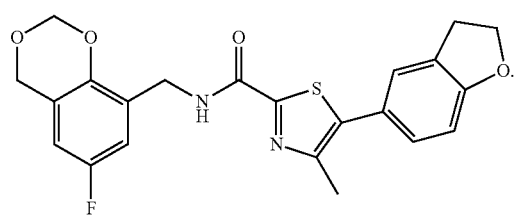 [SMILES: Cc1nc(C(=O)NCc2cc(F)cc3c2OCOC3)sc1-c1ccc2c(c1)CCO2]

2. The compound of claim 1, having the formula:

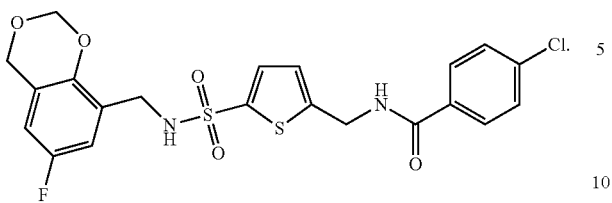

3. A pharmaceutical composition comprising a compound in accordance with claim 2.

4. A method of treating cancer drug resistance in a subject having cancer comprising administering to the subject a therapeutic amount of a compound of claim 2.

5. The method of claim 4, wherein the cancer is ovarian, prostate, melanoma, breast, pancreatic, brain, lung, colorectal, esophageal or neuroblastoma.

6. The compound of claim 1, having the formula:

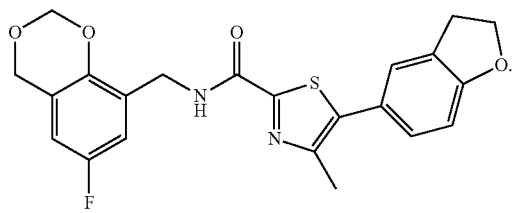

7. A pharmaceutical composition comprising a compound in accordance with claim 6.

8. A method of treating cancer drug resistance in a subject having cancer comprising administering to the subject a therapeutic amount of a compound of claim 6.

9. The method of claim 8 wherein the cancer is ovarian, prostate, melanoma, breast, pancreatic, brain, lung, colorectal, esophageal or neuroblastoma.

\* \* \* \* \*

SEQUENCE LISTING

```
<160> NUMBER OF SEQ ID NOS: 86

<210> SEQ ID NO 1
<211> LENGTH: 31
<212> TYPE: PRT
<213> ORGANISM: Homo sapiens
```

```
<400> SEQUENCE: 1

Ala Leu Leu Val Glu Pro Val Ile Asn Ser Tyr Leu Leu Ala Glu Arg
1               5                   10                  15

Asp Leu Tyr Leu Glu Asn Pro Glu Ile Lys Ile Arg Ile Leu Gly
            20                  25                  30

<210> SEQ ID NO 2
<211> LENGTH: 29
<212> TYPE: PRT
<213> ORGANISM: Homo sapiens

<400> SEQUENCE: 2

Leu Leu Val Glu Pro Val Ile Asn Ser Tyr Leu Leu Ala Glu Arg Asp
1               5                   10                  15

Leu Tyr Leu Glu Asn Pro Glu Ile Lys Ile Arg Ile Leu
            20                  25

<210> SEQ ID NO 3
<211> LENGTH: 27
<212> TYPE: PRT
<213> ORGANISM: Homo sapiens

<400> SEQUENCE: 3

Leu Val Glu Pro Val Ile Asn Ser Tyr Leu Leu Ala Glu Arg Asp Leu
1               5                   10                  15

Tyr Leu Glu Asn Pro Glu Ile Lys Ile Arg Ile
            20                  25

<210> SEQ ID NO 4
<211> LENGTH: 25
<212> TYPE: PRT
<213> ORGANISM: Homo sapiens

<400> SEQUENCE: 4

Val Glu Pro Val Ile Asn Ser Tyr Leu Leu Ala Glu Arg Asp Leu Tyr
1               5                   10                  15

Leu Glu Asn Pro Glu Ile Lys Ile Arg
            20                  25

<210> SEQ ID NO 5
<211> LENGTH: 23
<212> TYPE: PRT
<213> ORGANISM: Homo sapiens

<400> SEQUENCE: 5

Glu Pro Val Ile Asn Ser Tyr Leu Leu Ala Glu Arg Asp Leu Tyr Leu
1               5                   10                  15

Glu Asn Pro Glu Ile Lys Ile
            20

<210> SEQ ID NO 6
<211> LENGTH: 21
<212> TYPE: PRT
<213> ORGANISM: Homo sapiens

<400> SEQUENCE: 6

Pro Val Ile Asn Ser Tyr Leu Leu Ala Glu Arg Asp Leu Tyr Leu Glu
1               5                   10                  15

Asn Pro Glu Ile Lys
            20
```

```
<210> SEQ ID NO 7
<211> LENGTH: 19
<212> TYPE: PRT
<213> ORGANISM: Homo sapiens

<400> SEQUENCE: 7

Val Ile Asn Ser Tyr Leu Leu Ala Glu Arg Asp Leu Tyr Leu Glu Asn
1               5                   10                  15

Pro Glu Ile

<210> SEQ ID NO 8
<211> LENGTH: 17
<212> TYPE: PRT
<213> ORGANISM: Homo sapiens

<400> SEQUENCE: 8

Ile Asn Ser Tyr Leu Leu Ala Glu Arg Asp Leu Tyr Leu Glu Asn Pro
1               5                   10                  15

Glu

<210> SEQ ID NO 9
<211> LENGTH: 15
<212> TYPE: PRT
<213> ORGANISM: Homo sapiens

<400> SEQUENCE: 9

Asn Ser Tyr Leu Leu Ala Glu Arg Asp Leu Tyr Leu Glu Asn Pro
1               5                   10                  15

<210> SEQ ID NO 10
<211> LENGTH: 13
<212> TYPE: PRT
<213> ORGANISM: Homo sapiens

<400> SEQUENCE: 10

Ser Tyr Leu Leu Ala Glu Arg Asp Leu Tyr Leu Glu Asn
1               5                   10

<210> SEQ ID NO 11
<211> LENGTH: 11
<212> TYPE: PRT
<213> ORGANISM: Homo sapiens

<400> SEQUENCE: 11

Tyr Leu Leu Ala Glu Arg Asp Leu Tyr Leu Glu
1               5                   10

<210> SEQ ID NO 12
<211> LENGTH: 31
<212> TYPE: PRT
<213> ORGANISM: Homo sapiens

<400> SEQUENCE: 12

His Leu Asn Lys Leu Ala Glu Lys Glu Glu Thr Gly Met Ala Met Arg
1               5                   10                  15

Ile Arg Val Gly Gln Ser Met Asn Met Gly Ser Asp Phe Asp Val
            20                  25                  30

<210> SEQ ID NO 13
<211> LENGTH: 29
<212> TYPE: PRT
<213> ORGANISM: Homo sapiens

<400> SEQUENCE: 13
```

Leu Asn Lys Leu Ala Glu Lys Glu Glu Thr Gly Met Ala Met Arg Ile
1               5                   10                  15

Arg Val Gly Gln Ser Met Asn Met Gly Ser Asp Phe Asp
            20                  25

<210> SEQ ID NO 14
<211> LENGTH: 27
<212> TYPE: PRT
<213> ORGANISM: Homo sapiens

<400> SEQUENCE: 14

Asn Lys Leu Ala Glu Lys Glu Glu Thr Gly Met Ala Met Arg Ile Arg
1               5                   10                  15

Val Gly Gln Ser Met Asn Met Gly Ser Asp Phe
            20                  25

<210> SEQ ID NO 15
<211> LENGTH: 25
<212> TYPE: PRT
<213> ORGANISM: Homo sapiens

<400> SEQUENCE: 15

Lys Leu Ala Glu Lys Glu Glu Thr Gly Met Ala Met Arg Ile Arg Val
1               5                   10                  15

Gly Gln Ser Met Asn Met Gly Ser Asp
            20                  25

<210> SEQ ID NO 16
<211> LENGTH: 23
<212> TYPE: PRT
<213> ORGANISM: Homo sapiens

<400> SEQUENCE: 16

Leu Ala Glu Lys Glu Glu Thr Gly Met Ala Met Arg Ile Arg Val Gly
1               5                   10                  15

Gln Ser Met Asn Met Gly Ser
            20

<210> SEQ ID NO 17
<211> LENGTH: 21
<212> TYPE: PRT
<213> ORGANISM: Homo sapiens

<400> SEQUENCE: 17

Ala Glu Lys Glu Glu Thr Gly Met Ala Met Arg Ile Arg Val Gly Gln
1               5                   10                  15

Ser Met Asn Met Gly
            20

<210> SEQ ID NO 18
<211> LENGTH: 19
<212> TYPE: PRT
<213> ORGANISM: Homo sapiens

<400> SEQUENCE: 18

Glu Lys Glu Glu Thr Gly Met Ala Met Arg Ile Arg Val Gly Gln Ser
1               5                   10                  15

Met Asn Met

<210> SEQ ID NO 19
<211> LENGTH: 17

```
<212> TYPE: PRT
<213> ORGANISM: Homo sapiens

<400> SEQUENCE: 19

Lys Glu Glu Thr Gly Met Ala Met Arg Ile Arg Val Gly Gln Ser Met
1               5                   10                  15

Asn

<210> SEQ ID NO 20
<211> LENGTH: 15
<212> TYPE: PRT
<213> ORGANISM: Homo sapiens

<400> SEQUENCE: 20

Glu Glu Thr Gly Met Ala Met Arg Ile Arg Val Gly Gln Ser Met
1               5                   10                  15

<210> SEQ ID NO 21
<211> LENGTH: 13
<212> TYPE: PRT
<213> ORGANISM: Homo sapiens

<400> SEQUENCE: 21

Glu Thr Gly Met Ala Met Arg Ile Arg Val Gly Gln Ser
1               5                   10

<210> SEQ ID NO 22
<211> LENGTH: 11
<212> TYPE: PRT
<213> ORGANISM: Homo sapiens

<400> SEQUENCE: 22

Thr Gly Met Ala Met Arg Ile Arg Val Gly Gln
1               5                   10

<210> SEQ ID NO 23
<211> LENGTH: 31
<212> TYPE: PRT
<213> ORGANISM: Homo sapiens

<400> SEQUENCE: 23

Asn Lys Leu Ala Glu Lys Glu Glu Thr Gly Met Ala Met Arg Ile Arg
1               5                   10                  15

Val Gly Gln Ser Met Asn Met Gly Ser Asp Phe Asp Val Phe Ala
                20                  25                  30

<210> SEQ ID NO 24
<211> LENGTH: 29
<212> TYPE: PRT
<213> ORGANISM: Homo sapiens

<400> SEQUENCE: 24

Lys Leu Ala Glu Lys Glu Glu Thr Gly Met Ala Met Arg Ile Arg Val
1               5                   10                  15

Gly Gln Ser Met Asn Met Gly Ser Asp Phe Asp Val Phe
                20                  25

<210> SEQ ID NO 25
<211> LENGTH: 27
<212> TYPE: PRT
<213> ORGANISM: Homo sapiens

<400> SEQUENCE: 25
```

```
Leu Ala Glu Lys Glu Thr Gly Met Ala Met Arg Ile Arg Val Gly
1               5                   10                  15

Gln Ser Met Asn Met Gly Ser Asp Phe Asp Val
            20                  25

<210> SEQ ID NO 26
<211> LENGTH: 25
<212> TYPE: PRT
<213> ORGANISM: Homo sapiens

<400> SEQUENCE: 26

Ala Glu Lys Glu Thr Gly Met Ala Met Arg Ile Arg Val Gly Gln
1               5                   10                  15

Ser Met Asn Met Gly Ser Asp Phe Asp
            20                  25

<210> SEQ ID NO 27
<211> LENGTH: 23
<212> TYPE: PRT
<213> ORGANISM: Homo sapiens

<400> SEQUENCE: 27

Glu Lys Glu Thr Gly Met Ala Met Arg Ile Arg Val Gly Gln Ser
1               5                   10                  15

Met Asn Met Gly Ser Asp Phe
            20

<210> SEQ ID NO 28
<211> LENGTH: 21
<212> TYPE: PRT
<213> ORGANISM: Homo sapiens

<400> SEQUENCE: 28

Lys Glu Glu Thr Gly Met Ala Met Arg Ile Arg Val Gly Gln Ser Met
1               5                   10                  15

Asn Met Gly Ser Asp
            20

<210> SEQ ID NO 29
<211> LENGTH: 19
<212> TYPE: PRT
<213> ORGANISM: Homo sapiens

<400> SEQUENCE: 29

Glu Glu Thr Gly Met Ala Met Arg Ile Arg Val Gly Gln Ser Met Asn
1               5                   10                  15

Met Gly Ser

<210> SEQ ID NO 30
<211> LENGTH: 17
<212> TYPE: PRT
<213> ORGANISM: Homo sapiens

<400> SEQUENCE: 30

Glu Thr Gly Met Ala Met Arg Ile Arg Val Gly Gln Ser Met Asn Met
1               5                   10                  15

Gly

<210> SEQ ID NO 31
<211> LENGTH: 15
<212> TYPE: PRT
<213> ORGANISM: Homo sapiens
```

<400> SEQUENCE: 31

Thr Gly Met Ala Met Arg Ile Arg Val Gly Gln Ser Met Asn Met
1               5                   10                  15

<210> SEQ ID NO 32
<211> LENGTH: 13
<212> TYPE: PRT
<213> ORGANISM: Homo sapiens

<400> SEQUENCE: 32

Gly Met Ala Met Arg Ile Arg Val Gly Gln Ser Met Asn
1               5                   10

<210> SEQ ID NO 33
<211> LENGTH: 11
<212> TYPE: PRT
<213> ORGANISM: Homo sapiens

<400> SEQUENCE: 33

Met Ala Met Arg Ile Arg Val Gly Gln Ser Met
1               5                   10

<210> SEQ ID NO 34
<211> LENGTH: 687
<212> TYPE: PRT
<213> ORGANISM: Homo sapiens

<400> SEQUENCE: 34

Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
                20                  25                  30

Val Arg Arg Gly Gln Pro Phe Trp Leu Thr Leu His Phe Glu Gly Arg
            35                  40                  45

Asn Tyr Glu Ala Ser Val Asp Ser Leu Thr Phe Ser Val Val Thr Gly
        50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln
                85                  90                  95

Asp Cys Thr Leu Ser Leu Gln Leu Thr Thr Pro Ala Asn Ala Pro Ile
            100                 105                 110

Gly Leu Tyr Arg Leu Ser Leu Glu Ala Ser Thr Gly Tyr Gln Gly Ser
        115                 120                 125

Ser Phe Val Leu Gly His Phe Ile Leu Leu Phe Asn Ala Trp Cys Pro
    130                 135                 140

Ala Asp Ala Val Tyr Leu Asp Ser Glu Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Glu Asp Gly Ile Leu Asp Ile
            180                 185                 190

Cys Leu Ile Leu Leu Asp Val Asn Pro Lys Phe Leu Lys Asn Ala Gly
        195                 200                 205

Arg Asp Cys Ser Arg Arg Ser Ser Pro Val Tyr Val Gly Arg Val Val
    210                 215                 220

Ser Gly Met Val Asn Cys Asn Asp Asp Gln Gly Val Leu Leu Gly Arg

```
              225                 230                 235                 240
Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
                260                 265                 270

Lys Tyr Gly Gln Cys Trp Val Phe Ala Ala Val Ala Cys Thr Val Leu
                275                 280                 285

Arg Cys Leu Gly Ile Pro Thr Arg Val Val Thr Asn Tyr Asn Ser Ala
        290                 295                 300

His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
                340                 345                 350

Gly Trp Gln Ala Leu Asp Pro Thr Pro Gln Glu Lys Ser Glu Gly Thr
                355                 360                 365

Tyr Cys Cys Gly Pro Val Pro Val Arg Ala Ile Lys Glu Gly Asp Leu
        370                 375                 380

Ser Thr Lys Tyr Asp Ala Pro Phe Val Phe Ala Glu Val Asn Ala Asp
385                 390                 395                 400

Val Val Asp Trp Ile Gln Gln Asp Gly Ser Val His Lys Ser Ile
                405                 410                 415

Asn Arg Ser Leu Ile Val Gly Leu Lys Ile Ser Thr Lys Ser Val Gly
                420                 425                 430

Arg Asp Glu Arg Glu Asp Ile Thr His Thr Tyr Lys Tyr Pro Glu Gly
                435                 440                 445

Ser Ser Glu Glu Arg Glu Ala Phe Thr Arg Ala Asn His Leu Asn Lys
        450                 455                 460

Leu Ala Glu Lys Glu Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Leu Cys Ala Arg
                500                 505                 510

Thr Val Ser Tyr Asn Gly Ile Leu Gly Pro Glu Cys Gly Thr Lys Tyr
                515                 520                 525

Leu Leu Asn Leu Asn Leu Glu Pro Phe Ser Glu Lys Ser Val Pro Leu
        530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
                580                 585                 590

Ile Leu Gly Glu Pro Lys Gln Lys Arg Lys Leu Val Ala Glu Val Ser
                595                 600                 605

Leu Gln Asn Pro Leu Pro Val Ala Leu Glu Gly Cys Thr Phe Thr Val
        610                 615                 620

Glu Gly Ala Gly Leu Thr Glu Glu Gln Lys Thr Val Glu Ile Pro Asp
625                 630                 635                 640

Pro Val Glu Ala Gly Glu Glu Val Lys Val Arg Met Asp Leu Leu Pro
                645                 650                 655
```

```
Leu His Met Gly Leu His Lys Leu Val Val Asn Phe Glu Ser Asp Lys
                660             665             670

Leu Lys Ala Val Lys Gly Phe Arg Asn Val Ile Ile Gly Pro Ala
            675             680             685
```

<210> SEQ ID NO 35
<211> LENGTH: 19
<212> TYPE: DNA
<213> ORGANISM: Homo sapiens

<400> SEQUENCE: 35
gaacatgggc agtgactt                                                19

<210> SEQ ID NO 36
<211> LENGTH: 19
<212> TYPE: DNA
<213> ORGANISM: Homo sapiens

<400> SEQUENCE: 36
gggcgaacca cctgaacaa                                               19

<210> SEQ ID NO 37
<211> LENGTH: 19
<212> TYPE: DNA
<213> ORGANISM: Homo sapiens

<400> SEQUENCE: 37
ggtcaatgcc gacgtggta                                               19

<210> SEQ ID NO 38
<211> LENGTH: 19
<212> TYPE: DNA
<213> ORGANISM: Homo sapiens

<400> SEQUENCE: 38
tgaacaaact ggccgagaa                                               19

<210> SEQ ID NO 39
<211> LENGTH: 19
<212> TYPE: DNA
<213> ORGANISM: Homo sapiens

<400> SEQUENCE: 39
gcaccaagta cctgctcaa                                               19

<210> SEQ ID NO 40
<211> LENGTH: 19
<212> TYPE: DNA
<213> ORGANISM: Homo sapiens

<400> SEQUENCE: 40
aagaggagcg gcaggagta                                               19

<210> SEQ ID NO 41
<211> LENGTH: 19
<212> TYPE: DNA
<213> ORGANISM: Homo sapiens

<400> SEQUENCE: 41
aagaacatac cttggaatt                                               19

<210> SEQ ID NO 42

```
<211> LENGTH: 19
<212> TYPE: DNA
<213> ORGANISM: Homo sapiens

<400> SEQUENCE: 42
ccgaggagct ggtcttaga                                                 19

<210> SEQ ID NO 43
<211> LENGTH: 19
<212> TYPE: DNA
<213> ORGANISM: Homo sapiens

<400> SEQUENCE: 43
acaaactggc cgagaagga                                                 19

<210> SEQ ID NO 44
<211> LENGTH: 19
<212> TYPE: DNA
<213> ORGANISM: Homo sapiens

<400> SEQUENCE: 44
atctggagct ggagaccaa                                                 19

<210> SEQ ID NO 45
<211> LENGTH: 19
<212> TYPE: DNA
<213> ORGANISM: Homo sapiens

<400> SEQUENCE: 45
gcaacgatga ccagggtgt                                                 19

<210> SEQ ID NO 46
<211> LENGTH: 19
<212> TYPE: DNA
<213> ORGANISM: Homo sapiens

<400> SEQUENCE: 46
tgggtggagt cgtggatga                                                 19

<210> SEQ ID NO 47
<211> LENGTH: 19
<212> TYPE: DNA
<213> ORGANISM: Homo sapiens

<400> SEQUENCE: 47
acaacaccgc tgaggagta                                                 19

<210> SEQ ID NO 48
<211> LENGTH: 19
<212> TYPE: DNA
<213> ORGANISM: Homo sapiens

<400> SEQUENCE: 48
taagagatgc tgtggagga                                                 19

<210> SEQ ID NO 49
<211> LENGTH: 19
<212> TYPE: DNA
<213> ORGANISM: Homo sapiens

<400> SEQUENCE: 49
ggaggagggt gactggaca                                                 19
```

-continued

```
<210> SEQ ID NO 50
<211> LENGTH: 19
<212> TYPE: DNA
<213> ORGANISM: Homo sapiens

<400> SEQUENCE: 50
acgatgggtc tgtgcacaa                                                  19

<210> SEQ ID NO 51
<211> LENGTH: 19
<212> TYPE: DNA
<213> ORGANISM: Homo sapiens

<400> SEQUENCE: 51
cagaggagag ggaggcctt                                                  19

<210> SEQ ID NO 52
<211> LENGTH: 19
<212> TYPE: DNA
<213> ORGANISM: Homo sapiens

<400> SEQUENCE: 52
gaacaaactg gccgagaag                                                  19

<210> SEQ ID NO 53
<211> LENGTH: 19
<212> TYPE: DNA
<213> ORGANISM: Homo sapiens

<400> SEQUENCE: 53
atgctgtgga ggagggtga                                                  19

<210> SEQ ID NO 54
<211> LENGTH: 19
<212> TYPE: DNA
<213> ORGANISM: Homo sapiens

<400> SEQUENCE: 54
cgtgtgggcc agagcatga                                                  19

<210> SEQ ID NO 55
<211> LENGTH: 19
<212> TYPE: DNA
<213> ORGANISM: Homo sapiens

<400> SEQUENCE: 55
ggtgtgatct ggagctgga                                                  19

<210> SEQ ID NO 56
<211> LENGTH: 19
<212> TYPE: DNA
<213> ORGANISM: Homo sapiens

<400> SEQUENCE: 56
gagggtgact ggacagcca                                                  19

<210> SEQ ID NO 57
<211> LENGTH: 19
<212> TYPE: DNA
<213> ORGANISM: Homo sapiens

<400> SEQUENCE: 57
agaacatacc ttggaattt                                                  19
```

<210> SEQ ID NO 58
<211> LENGTH: 19
<212> TYPE: DNA
<213> ORGANISM: Homo sapiens

<400> SEQUENCE: 58
gaagatggga tcctagaca                                                19

<210> SEQ ID NO 59
<211> LENGTH: 19
<212> TYPE: DNA
<213> ORGANISM: Homo sapiens

<400> SEQUENCE: 59
gtggcatggt caactgcaa                                                19

<210> SEQ ID NO 60
<211> LENGTH: 19
<212> TYPE: DNA
<213> ORGANISM: Homo sapiens

<400> SEQUENCE: 60
ggagaagagc gaagggacg                                                19

<210> SEQ ID NO 61
<211> LENGTH: 19
<212> TYPE: DNA
<213> ORGANISM: Homo sapiens

<400> SEQUENCE: 61
gcagtgactt tgacgtctt                                                19

<210> SEQ ID NO 62
<211> LENGTH: 19
<212> TYPE: DNA
<213> ORGANISM: Homo sapiens

<400> SEQUENCE: 62
actcggaaga ggagcggca                                                19

<210> SEQ ID NO 63
<211> LENGTH: 19
<212> TYPE: DNA
<213> ORGANISM: Homo sapiens

<400> SEQUENCE: 63
gtacttccgc aatgagttt                                                19

<210> SEQ ID NO 64
<211> LENGTH: 19
<212> TYPE: DNA
<213> ORGANISM: Homo sapiens

<400> SEQUENCE: 64
tcacccacac ctacaaata                                                19

<210> SEQ ID NO 65
<211> LENGTH: 19
<212> TYPE: DNA
<213> ORGANISM: Homo sapiens

<400> SEQUENCE: 65
gaagaggagc ggcaggagt                                                19

<210> SEQ ID NO 66
<211> LENGTH: 19
<212> TYPE: DNA
<213> ORGANISM: Homo sapiens

<400> SEQUENCE: 66
ggatcggcag cgtggacat                                                    19

<210> SEQ ID NO 67
<211> LENGTH: 19
<212> TYPE: DNA
<213> ORGANISM: Homo sapiens

<400> SEQUENCE: 67
ctacccgcgt cgtgaccaa                                                    19

<210> SEQ ID NO 68
<211> LENGTH: 19
<212> TYPE: DNA
<213> ORGANISM: Homo sapiens

<400> SEQUENCE: 68
cccatgacca gaacagcaa                                                    19

<210> SEQ ID NO 69
<211> LENGTH: 19
<212> TYPE: DNA
<213> ORGANISM: Homo sapiens

<400> SEQUENCE: 69
gcaatgagtt tggggagat                                                    19

<210> SEQ ID NO 70
<211> LENGTH: 19
<212> TYPE: DNA
<213> ORGANISM: Homo sapiens

<400> SEQUENCE: 70
gtggagtcgt ggatgacca                                                    19

<210> SEQ ID NO 71
<211> LENGTH: 19
<212> TYPE: DNA
<213> ORGANISM: Homo sapiens

<400> SEQUENCE: 71
gtgccatcaa ggagggcga                                                    19

<210> SEQ ID NO 72
<211> LENGTH: 19
<212> TYPE: DNA
<213> ORGANISM: Homo sapiens

<400> SEQUENCE: 72
ccgagaagga ggagacagg                                                    19

<210> SEQ ID NO 73
<211> LENGTH: 19
<212> TYPE: DNA
<213> ORGANISM: Homo sapiens

<400> SEQUENCE: 73

```
actaagagat gctgtggag                                                19

<210> SEQ ID NO 74
<211> LENGTH: 19
<212> TYPE: DNA
<213> ORGANISM: Homo sapiens

<400> SEQUENCE: 74
cagcaagact gcaccctct                                                19

<210> SEQ ID NO 75
<211> LENGTH: 19
<212> TYPE: DNA
<213> ORGANISM: Homo sapiens

<400> SEQUENCE: 75
cgaaccacct gaacaaact                                                19

<210> SEQ ID NO 76
<211> LENGTH: 19
<212> TYPE: DNA
<213> ORGANISM: Homo sapiens

<400> SEQUENCE: 76
agaaggagga gacagggat                                                19

<210> SEQ ID NO 77
<211> LENGTH: 19
<212> TYPE: DNA
<213> ORGANISM: Homo sapiens

<400> SEQUENCE: 77
gaggagacag ggatggcca                                                19

<210> SEQ ID NO 78
<211> LENGTH: 19
<212> TYPE: DNA
<213> ORGANISM: Homo sapiens

<400> SEQUENCE: 78
aagatgggat cctagacat                                                19

<210> SEQ ID NO 79
<211> LENGTH: 19
<212> TYPE: DNA
<213> ORGANISM: Homo sapiens

<400> SEQUENCE: 79
accccaagtt cctgaagaa                                                19

<210> SEQ ID NO 80
<211> LENGTH: 19
<212> TYPE: DNA
<213> ORGANISM: Homo sapiens

<400> SEQUENCE: 80
gcaaccttct catcgagta                                                19

<210> SEQ ID NO 81
<211> LENGTH: 19
<212> TYPE: DNA
<213> ORGANISM: Homo sapiens

<400> SEQUENCE: 81
```

```
tcatcgagta cttccgcaa                                                19

<210> SEQ ID NO 82
<211> LENGTH: 19
<212> TYPE: DNA
<213> ORGANISM: Homo sapiens

<400> SEQUENCE: 82
gaccaatggc cgagaccac                                                19

<210> SEQ ID NO 83
<211> LENGTH: 19
<212> TYPE: DNA
<213> ORGANISM: Homo sapiens

<400> SEQUENCE: 83
ccaagtacct gctcaacct                                                19

<210> SEQ ID NO 84
<211> LENGTH: 19
<212> TYPE: DNA
<213> ORGANISM: Homo sapiens

<400> SEQUENCE: 84
gcagtttgaa gatgggatc                                                19

<210> SEQ ID NO 85
<211> LENGTH: 21
<212> TYPE: DNA
<213> ORGANISM: Homo sapiens

<400> SEQUENCE: 85
aaggcccgtt ttccactaag a                                             21

<210> SEQ ID NO 86
<211> LENGTH: 21
<212> TYPE: DNA
<213> ORGANISM: Homo sapiens

<400> SEQUENCE: 86
aagggcgaac cacctgaaca a                                             21
```